US010543294B2

(12) United States Patent
Voor et al.

(10) Patent No.: US 10,543,294 B2
(45) Date of Patent: *Jan. 28, 2020

(54) COMPOSITIONS AND METHODS FOR TREATING BONE DEFECTS

(71) Applicant: University of Louisville Research Foundation, Inc., Louisville, KY (US)

(72) Inventors: Michael J. Voor, Louisville, KY (US); Robert L. Burden, Jr., Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/742,342

(22) Filed: Jun. 17, 2015

(65) Prior Publication Data

US 2015/0283292 A1 Oct. 8, 2015

Related U.S. Application Data

(63) Continuation of application No. 13/219,376, filed on Aug. 26, 2011, now Pat. No. 9,072,720.

(60) Provisional application No. 61/337,262, filed on Aug. 26, 2010.

(51) Int. Cl.
| | | |
|---|---|---|
| *A61L 24/00* | (2006.01) | |
| *A61K 35/32* | (2015.01) | |
| *A61L 27/42* | (2006.01) | |
| *A61L 27/50* | (2006.01) | |
| *A61L 27/54* | (2006.01) | |
| *A61L 27/36* | (2006.01) | |
| *A61L 27/58* | (2006.01) | |
| *A61F 2/28* | (2006.01) | |
| *A61F 2/30* | (2006.01) | |

(52) U.S. Cl.
CPC .......... *A61L 24/0063* (2013.01); *A61K 35/32* (2013.01); *A61L 24/001* (2013.01); *A61L 24/0015* (2013.01); *A61L 24/0042* (2013.01); *A61L 24/0068* (2013.01); *A61L 27/365* (2013.01); *A61L 27/3608* (2013.01); *A61L 27/425* (2013.01); *A61L 27/427* (2013.01); *A61L 27/50* (2013.01); *A61L 27/54* (2013.01); *A61L 27/58* (2013.01); *A61F 2/28* (2013.01); *A61F 2002/30166* (2013.01); *A61F 2002/30199* (2013.01); *A61F 2310/00359* (2013.01); *A61L 2300/406* (2013.01); *A61L 2300/412* (2013.01); *A61L 2430/02* (2013.01)

(58) Field of Classification Search
None
See application file for complete search history.

(56) References Cited

U.S. PATENT DOCUMENTS

| | | |
|---|---|---|
| 3,686,377 A | 8/1972 | Hays |
| 4,880,610 A | 11/1989 | Constantz |
| 5,047,031 A | 9/1991 | Constantz |
| 5,129,905 A | 7/1992 | Constantz |
| 5,336,264 A | 8/1994 | Constantz |
| 5,507,813 A | 4/1996 | Dowd et al. |
| 5,559,022 A | 9/1996 | Naughton et al. |
| 5,672,346 A | 9/1997 | Srour et al. |
| 5,827,735 A | 10/1998 | Young et al. |
| 5,952,010 A | 9/1999 | Constantz |
| 5,962,028 A | 10/1999 | Constantz |
| 6,201,039 B1 | 3/2001 | Brown et al. |
| 6,294,187 B1 * | 9/2001 | Boyce ....................... A61F 2/28 424/422 |
| 6,432,436 B1 | 8/2002 | Gertzman et al. |
| 6,548,080 B1 | 4/2003 | Gertzman et al. |
| 6,599,516 B1 | 7/2003 | Knaack |
| 6,911,212 B2 | 6/2005 | Gertzman et al. |
| 7,163,691 B2 | 1/2007 | Knaack et al. |
| RE39,857 E | 9/2007 | Shimomura et al. |
| 7,270,813 B2 | 9/2007 | Shimp et al. |
| 7,291,345 B2 | 11/2007 | Winterbottom et al. |
| 7,494,950 B2 | 2/2009 | Armitage et al. |
| 7,628,851 B2 | 12/2009 | Armitage et al. |
| 2003/0009235 A1* | 1/2003 | Manrique ............... A61F 2/446 623/23.63 |

(Continued)

FOREIGN PATENT DOCUMENTS

| | | | |
|---|---|---|---|
| WO | WO 96/26237 | * | 8/1996 |
| WO | 199941440 A1 | | 8/1999 |

(Continued)

OTHER PUBLICATIONS

Bohner et al., "Injectability of Calcium Phosphate Pastes," Biomaterials, 2005, vol. 26, pp. 1553-1563.

(Continued)

*Primary Examiner* — Dennis J Parad
*Assistant Examiner* — Lyndsey M Beckhardt
(74) *Attorney, Agent, or Firm* — Jenkins, Wilson, Taylor & Hunt, P.A.

(57) ABSTRACT

A bone graft composition includes a biologically-resorbable cement and a plurality of processed bone particles, where each of the bone particles have a shape configured to interconnect with adjacent bone particles. A method for treating a bone defect using the bone graft compositions includes providing the bone graft composition and administering an effective amount of the bone graft composition to a site of a bone defect in a subject. Kits including a biologically-resorbable cement powder and a plurality of processed bone particles are also provided.

19 Claims, 47 Drawing Sheets

(56) References Cited

U.S. PATENT DOCUMENTS

| | | | |
|---|---|---|---|
| 2003/0055511 A1* | 3/2003 | Schryver | A61F 2/28 623/23.5 |
| 2003/0055512 A1* | 3/2003 | Genin | A61K 6/033 623/23.56 |
| 2003/0167093 A1 | 9/2003 | Xu et al. | |
| 2003/0185903 A1 | 10/2003 | Cole et al. | |
| 2003/0206937 A1 | 11/2003 | Gertzman et al. | |
| 2004/0146543 A1 | 7/2004 | Shimp et al. | |
| 2005/0084542 A1 | 4/2005 | Rosenberg et al. | |
| 2005/0249773 A1 | 11/2005 | Maspero et al. | |
| 2006/0015184 A1* | 1/2006 | Winterbottom | A61F 2/44 623/18.11 |
| 2006/0030948 A1 | 2/2006 | Manrique et al. | |
| 2007/0191963 A1 | 8/2007 | Winterbottom et al. | |
| 2008/0033572 A1 | 2/2008 | D'Antonio et al. | |
| 2008/0145392 A1 | 6/2008 | Knaack et al. | |
| 2008/0188946 A1 | 8/2008 | Rosenberg et al. | |
| 2010/0166879 A1 | 7/2010 | Shim et al. | |
| 2010/0173846 A1 | 7/2010 | Zimmermann | |
| 2010/0197636 A1 | 8/2010 | Bouler et al. | |
| 2012/0053692 A1 | 3/2012 | Voor et al. | |

FOREIGN PATENT DOCUMENTS

| | | |
|---|---|---|
| WO | 200166044 A2 | 9/2001 |
| WO | 2002083194 A1 | 10/2002 |
| WO | 2004110308 A2 | 12/2004 |

OTHER PUBLICATIONS

Brown et al., "A new Calcium Phosphate Water Setting Cement," pp. 352-357 in Cements research progress, 1986, American Ceramic Society, Westerville, OH, 1986.
Burguera et al., "Injectable and Rapid-setting Calcium Phosphate Bone Cement with Dicalcium Phosphate Dihydrate," J Biomed Mater Res, 2006, vol. 77B, pp. 126-134.
Burguera et al., "High Early Strength Calcium Phosphate Bone Cement: Effects of Dicalcium Phosphate Dihydrate and Absorbable Fibers," J Biomed Mater Res A, Dec. 5, 2005, vol. 75(4), pp. 966-975.
Chow LC, "Calcium Phosphate Cements: Chemistry, Properties, and Applications," Mater Res Symp Proc, 2000, vol. 599, pp. 27-37.
Fernandez et al., "Modulation of Porosity in Apatitic Cements by the use of α-Tricalcium Phosphate—Calcium Sulphate Dehydrate Mixtures," Biomaterials, 2005, vol. 26, pp. 3395-3404.
Genin D. "Percolation: Theory and Applications." NIST, 2007.
Tamai et al., "Novel Hydroxyapatite Ceramics with an Interconnective Porous Structure Exhibit Superior Osteoconduction in vivo," J Biomed Mater Res, 2002, vol. 59A, pp. 110-117.
Verron et al., "Calcium Phosphate Biomaterials as Bone Drug Delivery Systems: A Review," Drug Discovery Today, 2010, vol. 15(13-14), pp. 547-552.
Xu et al., "Strong, macroporous, and in situ-setting calcium phosphate cement-layered structures," Biomaterials, 2007, vol. 28(26), pp. 3786-3796.
Xu et al., "Injectable and Macroporous Calcium Phosphate Cement Scaffold," Biomaterials, 2006, vol. 27, pp. 4279-4287.
Xu et al., "Fast Setting Calcium Phosphate—chitosan Scaffold: Mechanical Properties and Biocompatibility," Biomaterials, 2005, vol. 26, pp. 1337-1348.
Xu et al., "Self-hardening Calcium Phosphate Composite Scaffold for bone Tissue Engineering," J Orthop Res, 2004, vol. 22, pp. 535-543.
Xu et al., "Fast-setting calcium phosphate scaffolds with tailored macropore formation rates for bone regeneration," J Biomed Mater Res A, 2004, vol. 68A:4, pp. 725-734.
Yokoyama et al., "Development of calcium phosphate cement using chitosan and citric acid for bone substitute materials," Biomaterials, 2002, vol. 23, pp. 1091-1101.

Zhang et al., "In-situ hardening hydroxyapatite-based scaffold for bone repair," J Mater Sci: Mater Med, 2006, vol. 7, pp. 437-445.
Zhang et al., "Effects of synergistic reinforcement and absorbable fiber strength on hydroxyapatite bone cement," J Biomed Mater Res, 2005, vol. 75A, pp. 832-840.
Xu et al., "Whisker-reinforced bioactive composites containing calcium phosphate cement fillers: effects of filler ratio and surface treatments on mechanical properties," J Biomed Mater Res, 2001, vol. 57(2), pp. 165-174.
Xu et al., "Strong and macroporous calcium phosphate cement: Effects of porosity and fiber reinforcement on mechanical properties," J Biomed Mater Res, 2001, vol. 57(3), pp. 457-466.
ISA/KR, International Search Report and Written Opinion issued in corresponding international application No. PCT/US2011/049425, dated Mar. 26, 2012.
European Patent Office, Supplementary European Search Report and Opinion, from Corresponding European Application No. 11820752.1, dated Feb. 13, 2014.
Speirs et al., "Calcium phosphate cement composites in revision hip arthroplasty," Biomaterials, 2002, vol. 26, pp. 7310-7318.
IP Australia, Patent Examination Report No. 1, issued in corresponding Application No. 2011293202, dated Jan. 18, 2016.
Canadian Intellectual Property Office, Examiner's Report issued in corresponding Application No. 2,809,606, dated Aug. 10, 2017.
Almirall A, et al. 2004. Fabrication of Low Temperature Macroporous Hydroxyapatite Scaffolds by Foaming and Hydrolysis of an a-TCP Paste. Biomaterials. 25:3671-80. [PubMed: 15020142].
Ambard AJ and Mueninghoff L. (2006) "Calcium phosphate cement: review of mechanical and biological properties". Journal of Prosthodontics. 15(5): 321-328.
Bohner M, et al. 2005. "Technological Issues for the Development of More Efficient Calcium Phosphate Bone Cements: a Critical Assessment." Biomaterials 26:6423-9. [PubMed: 15964620].
Bohner M. 2001. "Calcium phosphate emulsions: possible applications." Key Eng. Mater. 192-195:765-.
Burguera EF, et al. 2008. "Injectable Calcium Phosphate Cement: Effects of Powderto-Liquid Ratio and Needle Size." J Biomed Mater Res B Appl Biomater. Feb.;84(2):493-502.
Costantino PD, et al. 1992. "Experimental Hydroxyapatite Cement Cranioplasty." Plast. Reconstr. Surg. 90:174-91. [PubMed: 1321453].
Ducheyne P, et al. 1999. "Bioactive Ceramics: the Effect of Surface Reactivity on Bone Formation and Bone Cell Function." Biomaterials 20:2287-303. [PubMed: 10614935].
Durucan C, et al. 2000. "Low Temperature Formation of Calcium-Deficient Hydroxyapatite-PLA/PLGA Composites." J Biomed Mater Res 51A:717-25. [PubMed: 10880121].
Edwards et al. (1998). "Osteoinduction of Human Demineralized Bone: Characterization in a Rate Model." Clinical Orthopaedics and Related Research. No. 357:219-228.
Fernandez E, et al. 2005. "High-strength Apatitic Cement by Modification with Superplasticizers." Biomaterials. 26:2289-96. [PubMed: 15585231].
Friedman CD, et al. (1998) "BoneSourceTM Hydroxyapatite Cement: a Novel Biomaterial for Craniofacial Skeletal Tissue Engineering and Reconstruction." J Biomed Mater Res (Appl Biomater) 438:428-32.
Gan L, et al. 2004. Calcium Phosphate sol-gel-Derived Thin Films on Porous-surfaced Implants for Enhanced Osteoconductivity. Part I: Synthesis and Characterization. Biomaterials 25:5303-12. [PubMed: 15110481].
Gbureck U, et al. 2004. Ionic Modification of Calcium Phosphate Cement Viscosity: Part I: Hypodermic Injection and Strength Improvement of Apatite Cement. Biomaterials 25:2187-95. [PubMed: 14741634].
Gbureck U, et al. 2005. Factors Influencing Calcium Phosphate Cement Shelflife. Biomaterials 26:3691-7. [PubMed: 15621259].
Ginebra MP, et al. 1997. Setting Reaction and Hardening of an Apatite Calcium Phosphate Cement. J Dent Res 76:905-12. [PubMed: 9126187].
Grover LM, et al. 2003 In vitro ageing of Brushite Calcium Phosphate Cement. Biomaterials 24:4133-41. [PubMed: 12853243].

(56) References Cited

OTHER PUBLICATIONS

Guo H, et al. 2003. Laminated and Functionally Graded Hydroxyapatite/yttria Stabilized Tetragonal Zirconia Composites Fabricated by Spark Plasma Sintering. Biomaterials 24:667-75. [PubMed: 12437961].
Hench LL. 1998. "Bioceramics." J Am Ceram Soc 81:1705-28.
Hing KA, et al. 1999. "Characterization of Porous Hydroxyapatite." J Mater Sci: Mater Med 10:135-45. [PubMed: 15348161].
Ishikawa K, et al. 1997. "Non-decay type fast-setting calcium phosphate cement: Hydroxyapatite Putty Containing an Increased Amount of Sodium Alginate." J Biomed Mater Res 36A:393-9. [PubMed: 9260110].
Laurencin CT, et al. 1999. Tissue Engineering: Orthopedic Applications. Ann Rev Biomed Eng 1:19-46. [PubMed: 11701481].
Lee, Singh R. et al. 2010. "Hierarchically Structured Titanium Foams for Tissue Scaffold Applications." Acta Biomater. Dec. 6(12):4596-604.
Link DP, et al. 2006. "Mechanical Evaluation of Implanted Calcium Phosphate Cement Incorporated with PLGA Microparticles." Biomaterials 27:4941-7. [PubMed: 16759694].
Livingston T, et al. 2002. In vivo Evaluation of a Bioactive Scaffold for Bone Tissue Engineering. J Biomed Mater Res 62A:1-13. [PubMed: 12124781].
Martin RB, et al. 1989. "Effects of Bone Ingrowth on the Strength and Non-invasive Assessment of a Coralline Hydroxyapatite Material." Biomaterials 10:481-8. [PubMed: 2804236].
Notice of Allowance corresponding to U.S. Appl. No. 13/219,376 dated Mar. 2, 2015.
Pilliar RM, et al. 2001. "Porous Calcium Polyphosphate Scaffolds for Bone Substitute Applications-in vitro Characterization." Biomaterials 22:963-72. [PubMed: 113110 15].
Pittinger et al. 1999. "Multilineage potential of adult human mesenchymal stem cells." Science, Apr. 2,;284(5411):143-7.
Ryu HS, et al. 2004. "Fabrication of 1-Dimensional Porous Hydroxyapatite and Evaluation of its Osteoconductivity." J Mater Sci Mater Med. Mar.;15(3):267-7.
Saadeh PB, et al. 2001. "Repair of a Critical Size Defect in the Rat Mandible Using Allogenic Type I Collagen." J Craniofac Surg. Nov.;12(6):573-9.
Simske SJ, et al. 1997. "Porous materials for bone engineering." Mater Sci Forum 250:151-82.
Suchanek W, et al. 1998. Processing and Properties of Hydroxyapatite-based Biomaterials for use as hard tissue Replacement Implants. J Mater Res 13:94-117.
Thomson RC, et al. 1998. Hydroxyapatite Fiber Reinforced poly(a-hydroxyester) foams for Bone Regeneration. Biomaterials 19:1935-43. [PubMed: 9863527].
Ueyama Y, et al. 2001. Initial Tissue Response to anti-washout Apatite Cement in the rat Palatal Region: Comparison with Conventional Apatite Cement. J Biomed Mater Res 55A:652-60. [PubMed: 1128809].
Weisman et al. Annu. Rev. Cell. Dev. Biol. 17:387-403.
Xu HHK, et al. 2002. Calcium Phosphate Cement Containing Resorbable Fibers for Short-term Reinforcement and macroporosity. Biomaterials 23:193-202. [PubMed:11763861].
Xu HHK, et al. 2002. "Processing and Properties of Strong and Non-rigid Calcium Phosphate Cement." J Dent Res. 81(3):219-24. [Pub~ed: 11881631].
Xu HHK, et al. 2006. "Development of a Nonrigid, Durable Calcium Phosphate Cement for use in Periodontal Bone Repair." JADA, Aug. 137:1131-38.
Zuk et al. (2001) Tissue Engineering. 7:211-228.
ASTM D 790-03. Standard test methods for flexural properties of unreinforced and reinforced plastic and electrical insulating materials. West Conshohocken, PA: ASTM International; 2004.
Fukase Y, et al. 1990. "Setting Reactions and Compressive Strengths of Calcium Phosphate Cements." J Dent Res Dec.;69(12):1852-1856.
Interview Summary corresponding to U.S. Appl. No. 13/219,376 dated Aug. 12, 2014.
Interview Summary corresponding to U.S. Appl. No. 13/219,376 dated Mar. 11, 2014.
Jackson et al., 1999. "Hematopoietic Potential of Stem Cells Isolated from Murine Skeletal Muscle." PNAS 96(25):14482-86.
Julien M, et al. 2007. Physico-chemical-mechanical and in vitro Biological Properties of Calcium Phosphate Cements with Doped Amorphous Calcium Phosphates. Biomaterials 28:956-65. [PubMed: 17123598].

\* cited by examiner

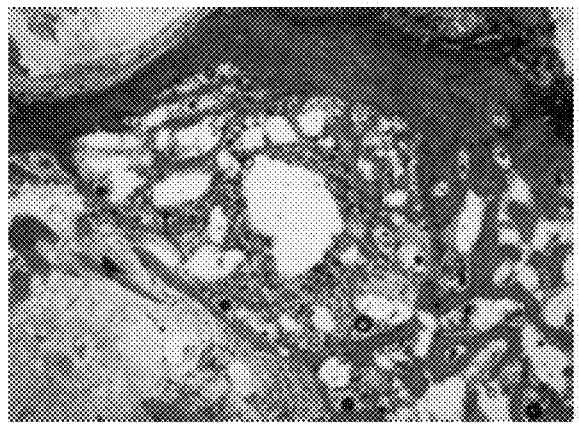 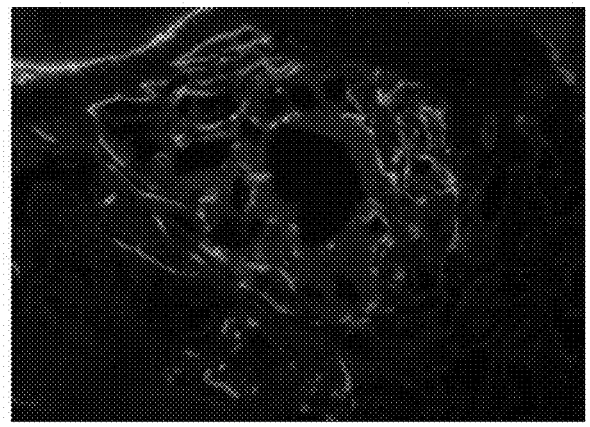
FIG. 26A  FIG. 26B
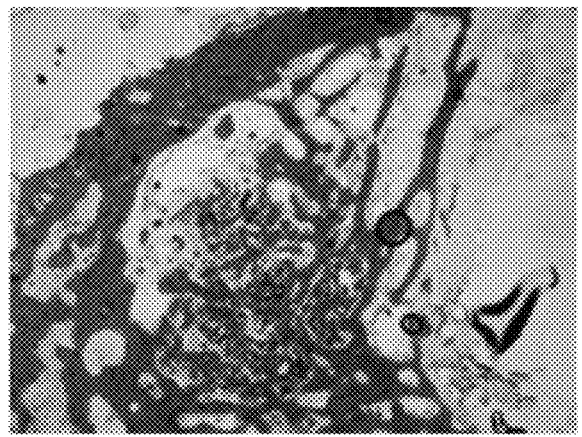 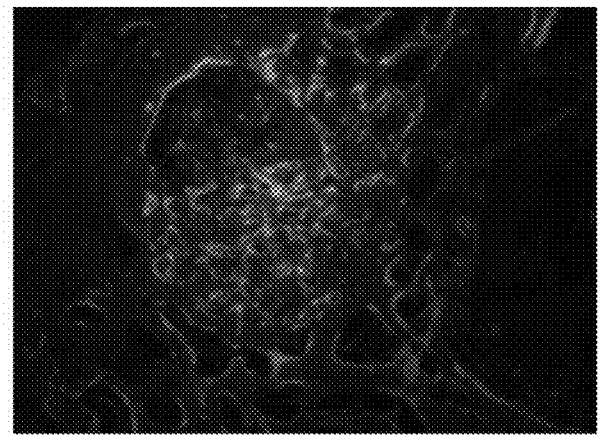
FIG. 26C  FIG. 26D

COMPOSITIONS AND METHODS FOR TREATING BONE DEFECTS

RELATED APPLICATIONS

This application is a continuation application of U.S. patent application Ser. No. 13/219,376, filed Aug. 21, 2011, which claims priority from U.S. Provisional Application Ser. No. 61/377,262, filed Aug. 26, 2010, the entire disclosures of which are incorporated herein by this reference.

TECHNICAL FIELD

The presently-disclosed subject matter relates to compositions and methods for treating bone defects and, more particularly, to bone graft compositions where the mechanical properties, incorporation, and remodeling of a biologically-resorbable cement are improved by augmenting the cement with processed bone particles.

BACKGROUND

Over 500,000 bone graft procedures are performed annually in the United States, and approximately 2.2 million are performed worldwide with an annual cost of nearly $2.5 billion. These bone graft procedures are routinely performed to not only treat bone fractures and other bone defects, but are also routinely performed to strengthen existing bone that may be deteriorating. Typically, the bone material used for these bone graft procedures is either autograft, which is derived from the patient's own body, or allograft, which is derived from a genetically dissimilar member of the same species. In some cases though, the graft material can even be xenograft, which is taken from another species.

From a biological standpoint, autograft is the preferred type of graft material and the type of material that is most commonly used in many of the orthopedic, maxillofacial, podiatric, and dental surgeries that require bone graft procedures to be performed. Autograft bone materials also exhibit many of the preferred properties for treating a bone defect, including the ability to produce new bone from transplanted living cells and the ability to integrate with the bone tissue at the graft site. Despite these advantages, however, an autograft procedure usually requires that additional surgery be performed on a subject to acquire the graft material, which can lead to complications, such as inflammation or infection. In addition, during these surgeries, only a very limited amount of bone can be collected. As such, allograft and xenograft materials have been developed that provide benefits in terms of the quantity of materials that can be obtained, but those materials still frequently have their own complications, such as disease transmission and graft failure, thus leaving researchers looking for better alternatives.

To that end, many additional types of bone graft compositions have been recently developed, including allograft-based, ceramic-based, and polymer-based compositions. For example, U.S. Pat. No. 7,494,950 describes implantable compositions containing a calcium salt-containing component, optionally demineralized bone, and a plurality of discrete fibers. For another example, U.S. Pat. No. 6,548,080 describes an application for a bone defect site that includes a partially demineralized cortical bone structure. As yet another example, U.S. Pat. No. 6,599,516 describes the inclusion of materials within a moldable ceramic compound capable of hardening, with the specific goal of allowing cellular access to the interior of the implanted material.

Nevertheless, despite the many alternative bone graft compositions available today, the currently-available alternative bone graft compositions generally do not possess sufficient strength and are not rapidly or completely incorporated, remodeled, or resorbed by the body of a subject. Thus, they can not be considered as viable alternatives to prior autograft-, allograft-, or xenograft-based bone graft materials. Furthermore, currently-available bone graft compositions do not sufficiently address how certain concentrations or shapes of the bone particles can be incorporated into a bone graft composition in a manner that changes the properties of the composition itself and increases the strength, resorption rate, and rate of incorporation and remodeling of the implanted materials.

SUMMARY

This Summary describes several embodiments of the presently-disclosed subject matter, and, in many cases, lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes bone graft compositions, methods of using the bone graft compositions to treat a bone defect, and kits comprising the components of the bone graft compositions. In particular, the presently-disclosed subject matter provides bone graft compositions, methods of using those compositions, and kits comprising the components of the bone graft compositions, where the mechanical properties and incorporation of a biologically-resorbable cement is increased by augmenting the cement with processed bone particles having an interconnecting shape.

In some embodiments of the presently-disclosed subject matter, a bone graft composition is provided that comprises a biologically-resorbable cement and a plurality of processed bone particles. In these compositions, each of the bone particles has an interconnecting shape (e.g., a dumbbell shape), such that each bone particle is capable of interconnecting with adjacent bone particles when it is included in the bone graft composition. In some embodiments, the interconnecting of the shaped bone particles increases the mechanical properties of the biologically-resorbable cement. In some embodiments, the bone particles are also configured to interlock with adjacent bone particles and/or configured to interdigitate with the surrounding cement such that the interlocking and/or interdigitating of the bone particles further increases the mechanical properties of the biologically-resorbable cement. In some embodiments, a cross-section of a portion of the processed bone particles is substantially round, elliptical, square, rectangular, or triangular in shape, such that the cement is further improved in compression, shear, tension, and bending loading modes as compared to a cement composition that does not include bone particles or one that includes randomly-shaped or randomly-oriented particles.

With respect to the biologically-resorbable cements utilized in accordance with the presently-disclosed bone graft compositions, in some embodiments, the biologically-resorbable cements are comprised of a calcium-based cement.

In some embodiments, the calcium-based cement is a calcium phosphate cement. In certain embodiments, the calcium-based cement is a hydroxyapatite cement. In other embodiments, the calcium-based cement is a calcium sulfate cement.

The processed bone particles of the presently-disclosed bone graft compositions are typically combined with the cement at a concentration of about 1 percent to about 50 percent by volume of the bone graft composition or, in some embodiments, at a concentration of about 1 to about 15 percent by volume of the bone graft composition. In some embodiments of the presently-disclosed bone graft compositions, the processed bone particles are about 5 percent to about 90 percent demineralized. In such embodiments, the processed bone particles are typically comprised of cortical bone particles. In other embodiments of the presently-disclosed bone graft compositions, the bone particles are comprised of cancellous bone particles. In further embodiments, the bone particles include both cortical and cancellous bone.

Further, the processed bone particles of the presently-disclosed bone graft compositions can, in some embodiments, be selected from autograft bone particles, allograft bone particles, xenograft bone particles, and combinations thereof. In some embodiments, the bone graft compositions can further include an antibiotic, an osteoinductive material, an osteogenic material, or both an osteoinductive and an osteogenic material.

Still further provided, in some embodiments of the presently-disclosed subject matter, are methods for treating a bone defect that make use of the bone graft compositions described herein. In some embodiments, a method for treating a bone defect is provided that comprises the steps of providing a bone graft composition of the presently-disclosed subject matter and administering an effective amount of the bone graft composition to a site of a bone defect in a subject. In some embodiments, the bone defect is a bone void, a fracture, or the site of an intended bone fusion. Each of these bone defects are treated, in some embodiments, by filling the bone defect with a bone graft composition of the presently-disclosed subject matter.

In yet further embodiments of the presently-disclosed subject matter, kits are provided. In some embodiments, a kit is provided that includes a biologically-resorbable cement powder and a plurality of processed bone particles, where each of the processed bone particles has a shape configured to interconnect with adjacent bone particles. In some embodiments of the kits, the biologically-resorbable cement and the processed bone particles are packed in separate vessels or are packaged together in a single vessel. In some embodiments, the bone particles are lyophilized. In this regard, in some embodiments, the kit further includes water or another aqueous vehicle for adding to the cement powder, the bone particles, or both the cement powder and the bone particles. In some embodiments, the kit further comprises instructions for mixing the cement powder and the bone particles, and then combining that mixture with an aqueous vehicle such that a desired bone graft composition is produced.

Further advantages of the presently-disclosed subject matter will become evident to those of ordinary skill in the art after a study of the description, Figures, and non-limiting Examples in this document.

DESCRIPTION OF THE DRAWINGS

FIGS. 26A-26D include light and fluorescent microscopy images of cancellous bone defects in the lateral femoral condyles of rabbits that were filled with allograft cancellous bone obtained from other rabbits or xenograft cancellous bone from young pigs, including images of the allograft-treated bone defects after 10 weeks with hematoxylin/eosin staining (FIG. 26A) and with calcein labeling (FIG. 26B) to show the addition of new bone, and images of xenograft-treated bone defects after 10 weeks with hematoxylin/eosin staining (FIG. 26C) and with calcein labeling to show the addition of new bone (FIG. 26D);

DESCRIPTION OF EXEMPLARY EMBODIMENTS

Figure 1A:
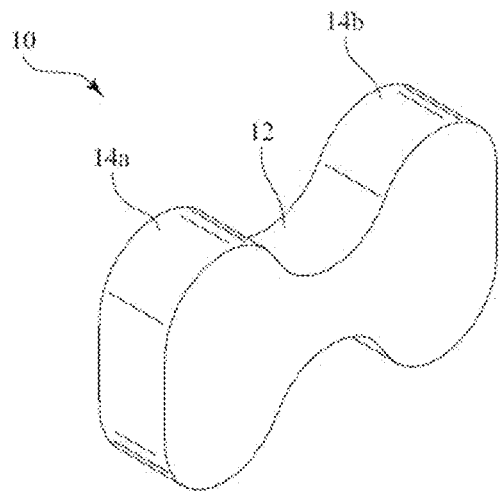
FIG. 1A is a perspective view of a dumbbell-shaped bone particle made in accordance with the presently-disclosed subject matter.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding, and no unnecessary limitations are to be understood therefrom.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although many methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a bone particle" includes a plurality of such particles, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations in some embodiments of ±20%, in some embodiments of ±10%, in some embodiments of ±5%, in some embodiments of ±1%, in some embodiments of ±0.5%, and in some embodiments of ±0.1% from the specified amount, as such variations are appropriate to perform the disclosed method.

Bone grafting is a surgical procedure that replaces missing bone with autograft, allograft, or xenograft bone materials, or a suitable bone graft composition. Bone grafting is possible because bone, unlike many other tissues, has the ability to regenerate completely if it is provided with the proper conditions and space in which to grow. For any bone graft composition to be effective and allow natural bone to fully occupy the space of a previous defect, however, several important qualities must be taken into consideration including: strength or mechanical stability (i.e., the ability to maintain physical relationships between bone surfaces into which the material is placed); osteoconductivity (i.e., the capability to function as a scaffold onto which new bone can form); and, in some instances, osteoinductivity (i.e., the property of stimulating migration and proliferation of bone cells in the subject to grow and become active at the graft site). As such, a synthetic bone graft composition should provide immediate mechanical stability and resorb quickly, but yet should also be able to effectively promote new bone formation. To that end, the presently-disclosed subject matter includes novel bone graft compositions that are comprised of bone particles of varying shapes, sizes, and quantities such that the bending strength and toughness, shear strength and toughness, tensile strength and toughness, and incorporation and remodeling rates of the compositions are optimized.

In some embodiments of the presently-disclosed subject matter, a bone graft composition is provided that includes materials added to a biologically-resorbable cement, which allow the cement structure that forms, after it sets in the body, to more rapidly incorporate and remodel. In some embodiments, the materials that are added to the compositions include processed bone particles, which allow the compositions to remodel faster when placed in a subject, but also allow for infiltration of the cement structure by cells, blood, and other such bodily fluids and structures.

In some embodiments of the presently-disclosed subject matter, bone graft compositions are provided that include specially-shaped, processed bone particles. In some embodiments, a bone graft composition is provided that comprises a biologically-resorbable cement and a plurality of processed bone particles. As described in further detail below, in these compositions, each of the processed bone particles has a shape such that is configured to interconnect and interlock with adjacent bone particles, the surrounding cement, or both when it is included in a bone graft composition of the presently-disclosed subject matter.

The term "biologically-resorbable cement" is used herein to refer to any biological cement, such as a bone substitute cement, that is capable of being broken down and assimilated by the body of a subject, and that is substantially non-toxic in the in vivo environment of its intended use such that it is not substantially rejected by the subject's physiological system (i.e., is non-antigenic or biocompatible). This can be gauged by the composition's toxicity, infectivity, pyrogenicity, irritation potential, reactivity, hemolytic activity, carcinogenicity and/or immunogenicity. A biologically-resorbable cement, when introduced into a bone of a majority of subjects, will not cause an undesirably adverse, long-lived or escalating biological reaction or response, and is distinguished from a mild, transient inflammation which typically accompanies surgery or implantation of foreign objects into a living organism.

As would be recognized by those skilled in the art, a "cement" is a product that is produced as a result of the setting of a paste that is formed by mixing a powdered component with water or another aqueous vehicle. A number of biologically-resorbable cements can be formed by mixing a powder component with water or another aqueous vehicle and then used in accordance with the presently-disclosed bone graft compositions, including, but not limited to, ceramics-based cements, calcium-based cements, magnesium ammonium-based cements, and the like. In some embodiments of the presently-disclosed compositions, the biologically-resorbable cement is a calcium-based cement, such as a calcium sulfate cement or a calcium phosphate cement, where the powdered component is comprised of a calcium-based compound. In some embodiments, the calcium-based cement is a calcium phosphate cement. In other embodiments, the calcium-based cement is a calcium sulfate cement.

The phrase "calcium phosphate cement" is used herein to refer to a cement where the powdered component of the cement is comprised of a calcium phosphate compound or a mixture of calcium and/or phosphate compounds. Exemplary calcium phosphate compounds or mixtures of calcium compounds and/or phosphate compounds that can be mixed with water or another aqueous vehicle and used in accordance with the presently-disclosed subject matter include, but are not limited to: tricalcium phosphate ($Ca_3(PO_4)_2$; TCP), including alpha-TCP, beta-TCP, and biphasic calcium phosphate containing alpha- and beta-TCP; amorphous calcium phosphate (ACP); monocalcium phosphate ($Ca(H_2PO_4)_2$; MCP) and monocalcium phosphate monohydrate ($Ca(H_2PO_4)_2 \cdot H_2O$; MCPM); dicalcium phosphate ($CaHPO_4$; DCP), dicalcium phosphate anhydrous ($CaHPO_4$; DCPA) and dicalcium phosphate dihydrate ($CaH_5PO_6 \cdot 2H_2O$; DCPD); tetracalcium phosphate (($Ca_4PO_4)_2O$; TTCP); octacalcium phosphate ($Ca_8(PO_4)_4HPO_4)_2 \cdot 5H_2O$; OCP); calcium hydroxyapatite ($Ca_m(PO_4)_6(OH)_2$; CHA); calcium oxyapatite ($Ca_m(PO_4)_6O$; COXA); calcium carbonate apatite ($Ca_{10}(PO_4)_6CO_3$; CCA); and calcium carbonate hydroxyapatites (e.g., $Ca_{10}(PO_4)_5(OH)(CO_3)_2$ and $C_{10}(PO_4)_4(OH)_2(CO_3)_3$; CCHA). Additional calcium phosphates useful herein also include calcium-deficient calcium phosphates in which the molar or mass ratio of Ca:P is reduced by about 20% or less, about 15% or less, or about 10% or less, relative to the corresponding calcium non-deficient species, examples of which include calcium-deficient hydroxyapatites, e.g., $Ca_{10-x}(HPO_4)_x(PO_4)_{6-x}(OH)_{2-x}$ (0≤X≤1) (CDHA); calcium-deficient carbonate hydroxyapatites (CDCHA); calcium-deficient carbonate apatites (CDCA); and other calcium phosphate compounds and salts known to be useful in the field of bone graft materials, e.g., calcium polyphosphates; and calcium-, phosphate-, and/or hydroxyl "replaced" calcium phosphates. In some embodiments, the calcium-phosphate cement is a hydroxyapatite cement. For further explanation and guidance regarding calcium phosphate cements, see, e.g., Ambard, et al. Journal of Prosthodontics. 15(5): 321-326 (2006).

The phrase "calcium sulfate cement" is used herein to refer to a cement where the powdered component of the cement is comprised of a calcium sulfate compound or a mixture of calcium and/or sulfate compounds. Exemplary calcium sulfate compounds or mixtures of calcium compounds and/or sulfate compounds that can be mixed with water or another aqueous vehicle and used in accordance with the presently-disclosed subject matter include, but are not limited to: calcium sulfate ($CaSO_4$); calcium sulfate dihydrate ($2CaSO_4 \cdot 2H_2O$); and calcium sulfate hemihydrate ($CaSO_4 \cdot \frac{1}{2}H_2O$). For further explanation and guidance regarding calcium sulfate cements, see, e.g., Bohner, European Cells & Materials, Vol. 20, 2010, pages 1-12.

Turning now to the processed bone particles that are included in the presently-disclosed bone graft compositions, the phrase "processed bone particles" is used herein to refer to pieces of bone that are derived from an intact bone, or part of an intact bone, and have been modified to produce pieces of bone with a desired level of mineralization, a desired size, and/or a desired shape, such that the pieces of bone can be combined with a suitable cement and applied to the site of a bone defect, as described in detail below. In some embodiments, the processed bone particles are of a size and shape that allows a prescribed mixture of cement (e.g., calcium phosphate cement) and processed bone particles to flow in a paste-like consistency, similar to the handling characteristics of processed cement. In some embodiments, the processed bone particles are from an autograft bone source, an allograft bone source, a xenograft bone source, or combinations thereof.

To produce an exemplary bone graft composition of the presently-disclosed subject matter, a specially-shaped bone particle is first obtained by refining an intact whole bone into a number of discrete particles. For example, to obtain a cortical bone particle having an interconnecting shape, as also described in further detail below, the soft tissue is first removed from the diaphysis of an intact bone, and the distal and proximal ends of the bone are removed. The bone marrow and the soft tissue inside the bone's shaft are then removed, and the inside of the bone is rinsed out, subsequent to removing any remaining cancellous bone from the inside of the diaphysis. The shaft of bone is then cut into thinned pieces of cortical bone, and is then typically either inserted into a punch that cuts the bone pieces into a desired interconnecting shape with a desired thickness or, in some embodiments, is mounted in a lathe to produce bone particles having a desired interconnecting shape. Of course, other techniques known to those of ordinary skill in the art including laser cutting techniques and the like can also be used to produce bone particles having a desired interconnecting shape and can be used without departing from the spirit and scope of the subject matter described herein.

The cement mixtures of the bone graft compositions are generally formed by mixing the powdered component of the cement with water or another aqueous vehicle. In this regard, once the specially-shaped bone particles are formed, the bone particles are then mixed with the cement at a desired concentration, as described further below. The term "aqueous vehicle" is used herein to refer to any fluid, such as water, that can be mixed with a powdered component of a cement to form a suitable paste of a biologically-resorbable cement. In this regard, the aqueous vehicle must also be substantially non-toxic in the in vivo environment of its intended use such that it is not substantially rejected by the subject's physiological system. In addition to water, such aqueous vehicles can include, but are not limited to, buffered saline solutions, sodium phosphate monobasic monohydrate ($NaH_2PO_4 \cdot H_2O$) solutions, sodium phosphate dibasic ($Na_2HPO_4$) solutions, glycerol solutions, and the like.

Typically, the amount of water or other aqueous vehicle that is mixed with the powdered component of the cement and the specially-shaped processed bone particles of the presently-disclosed subject matter is at least enough to generate the standard chemical reaction for cement setting to occur. When the bone particles are mixed with the cement, the aqueous vehicles temporarily hydrate any exposed collagen in the processed bone particles to allow the bone graft compositions to initially have flow and adherence properties of a standard processed cement. As the water is consumed, the collagen then binds with its surroundings and, at this point, any excess water, or other aqueous vehicle, beyond what is needed for the cement reaction to occur, can be taken up by the porosity of the bone particles or the exposed collagen. In some embodiments, the amount of water absorbed or adsorbed by the particles is about 30 percent to about 50 percent of the weight of the dry bone particles, such that, in certain embodiments, the amount of water or other aqueous vehicle absorbed or adsorbed by the bone particles comprises about 10 percent to about 20 percent of the volume of aqueous vehicle necessary for the setting reaction to occur.

As noted above, the bone particles of the presently-disclosed bone graft compositions have a shape that is configured to interconnect with adjacent bone particles when a plurality of the bone particles are included in a bone graft composition of the presently-disclosed subject matter. The terms "interconnect" or "interconnecting" as used herein in reference to the processed bone particles refer to bone particles having shapes that include intersecting surfaces or other structural features that allow the bone particles to interlock and/or more readily interact with one another, as opposed to simple cylindrical or spherical bone particles that would be unable to interlock with one another or would be less efficient at creating interconnected pathways by virtue of the association of one bone particle with one or more additional, adjacent bone particles.

Figure 1B:
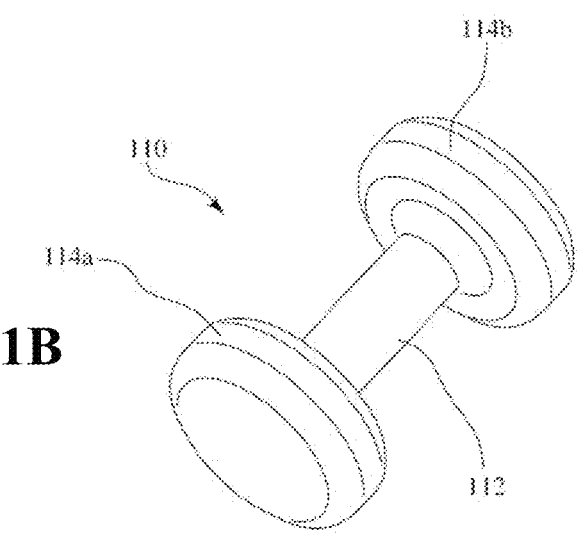
FIG. 1B is a perspective view of another dumbbell-shaped bone particle made in accordance with the presently-disclosed subject matter.
Figure 1C:
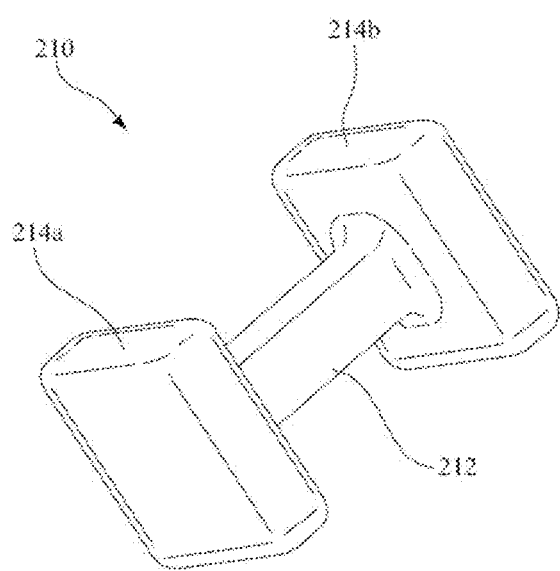
FIG. 1C is a perspective view of a further dumbbell-shaped bone particle made in accordance with the presently-disclosed subject matter.
Figure 2:
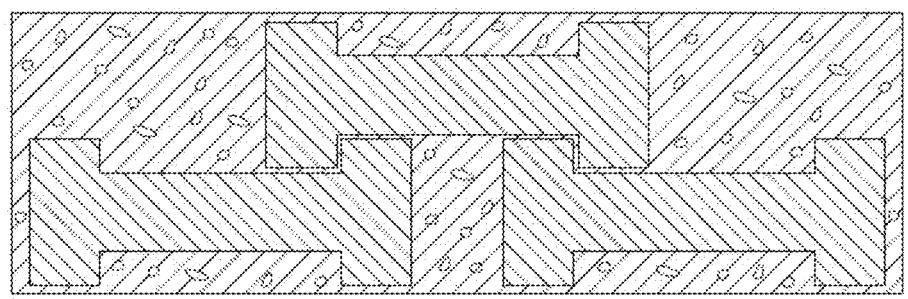
FIG. 2 is a schematic diagram showing a plurality of dumbbell-shaped bone particles interconnected with one another.
Figure 18:
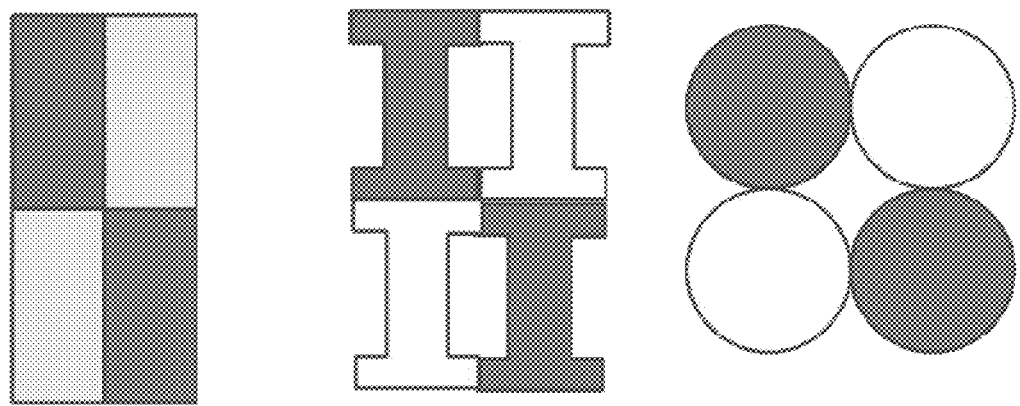
FIG. 18 is a schematic diagram showing the ability of various shaped bone particles to interconnect with one another, where rectangular bone particles and dumbbell-shaped bone particles are capable of interconnecting with one another along multiple surfaces, on the sides and corners of the shaped particles, but where circular bone particles are only capable of interconnecting with one another at single points of contact.

For example, in some embodiments and as shown in FIGS. 1A-1C and 1E, the bone particles 10, 110, 210, 410 are dumbbell-shaped, such that when the dumbbell-shaped bone particles 10, 110, 210, 410 are included in a bone graft composition of the presently-disclosed subject matter, the enlarged ends 14a, 14b, 114a, 114b, 214a, 214b, 414a, 414b of the dumbbell-shaped bone particles 10, 110, 210, 410 overlap and allow contact and engagement of the dumbbell-shaped bone particles along multiple surfaces (see, e.g., FIGS. 2 and 18). In some embodiments of the dumbbell-shaped bone particles, and as also shown in FIGS. 1A-1C and 1E, each bone particle 10, 110, 210, 410 includes two enlarged end portions 14a, 14b, 114a, 114b, 214a, 214b, 414a, 414b that extend laterally away from a longitudinal axis of the center portion 12, 112, 212, 412 of each bone particle. In some embodiments of the dumbbell-shaped bone particles, and as shown in FIG. 1B, a dumbbell-shaped bone particle 110 is provided that includes a center portion 112 with a circular cross-section and two disc-shaped end portions 114a, 114b that extend laterally away from (e.g., are oriented in a direction perpendicular to) the longitudinal axis of the center portion 112. In further embodiments, and as shown in FIG. 1C, a dumbbell-shaped bone particle 210 is provided that includes a center portion 212 with a generally elliptical cross-section and substantially square ends 214a, 214b that extend laterally away from the longitudinal axis of the center portion 212. In yet other embodiments, and as show in FIG. 1E, a dumbbell-shaped bone particle 410 is provided that includes a substantially-flat top surface 418 and a substantially-flat bottom surface 416, and further includes a center portion 412 with a generally square cross-section, and rectangular end portions 414a, 414b that laterally extend away from and are oriented in a direction perpendicular to the longitudinal axis of the center portion 412. Of course, to the extent it may be desired, bone particles of various other interconnecting shapes that would be capable of connecting with one another on multiple surfaces, such as "S-shaped" or "T-shaped" or "C-shaped" bone particles, can also be produced and used in a bone graft composition of the presently-disclosed subject matter without departing from the spirit and scope of the subject matter described herein.

Figure 1D:
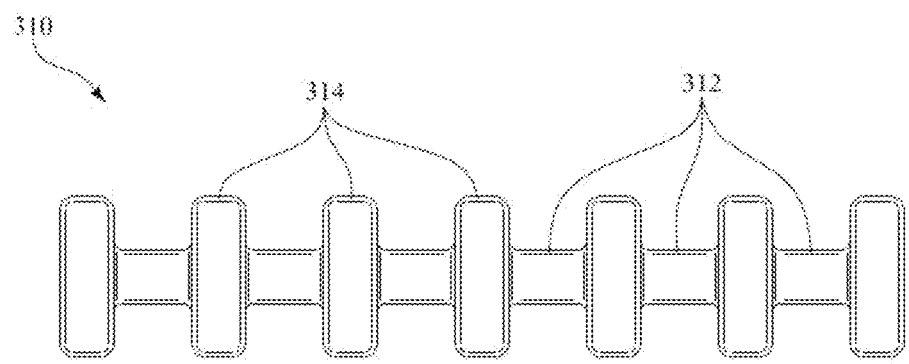
FIG. 1D is a side view of an elongated bone particle made in accordance with the presently-disclosed subject matter.
Figure 1E:
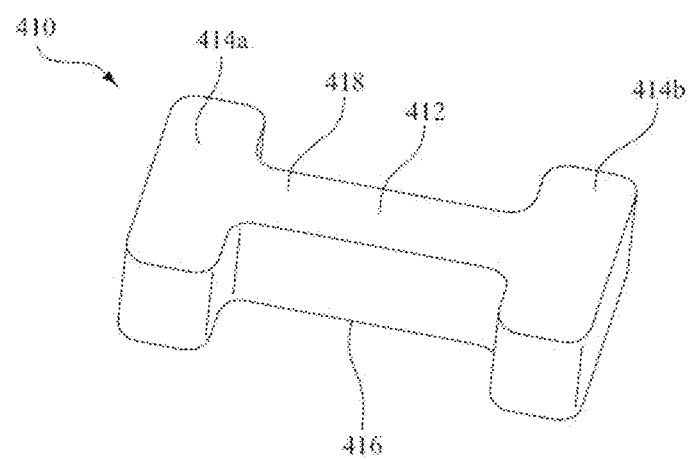
FIG. 1E is a perspective view of yet another dumbbell-shaped bone particle made in accordance with the presently-disclosed subject matter.

Furthermore, in certain embodiments, a number of interconnecting shapes having increased lengths can be provided that are capable of interconnecting with one another on multiple surfaces. For example, and as shown in FIG. 1D, in some embodiments, an elongated bone particle 310 is provided that includes a plurality of rectangular portions 314 and a plurality of center portions 312 aligned along a common longitudinal axis. In the bone particle 310, each of the rectangular portions 314 are oriented in a direction perpendicular to the common longitudinal axis of each center portion 312 and each of the center portions 312 are interposed between the respective rectangular portions 314. As another example of an elongated bone particle made in accordance with the presently-disclosed subject matter, and as shown in FIG. 1F, an elongated bone particle 510 is provided that includes a plurality of enlarged, spherical portions 514 and a plurality of center portions 512 aligned along a common longitudinal axis, where each of the enlarged portions 514 extend laterally away from the common longitudinal axis of each center portion 512, and where each of the center portions 512 are interposed between respective enlarged portions 514.

Figure 1F:
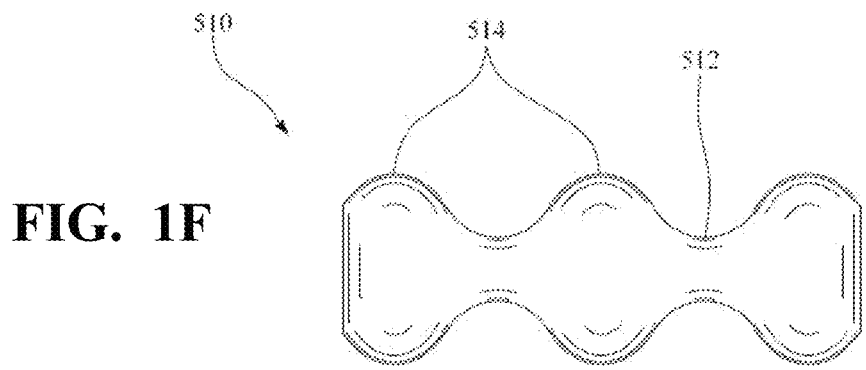
FIG. 1F is a side view of another elongated bone particle made in accordance with the presently-disclosed subject matter.
Figure 1G:
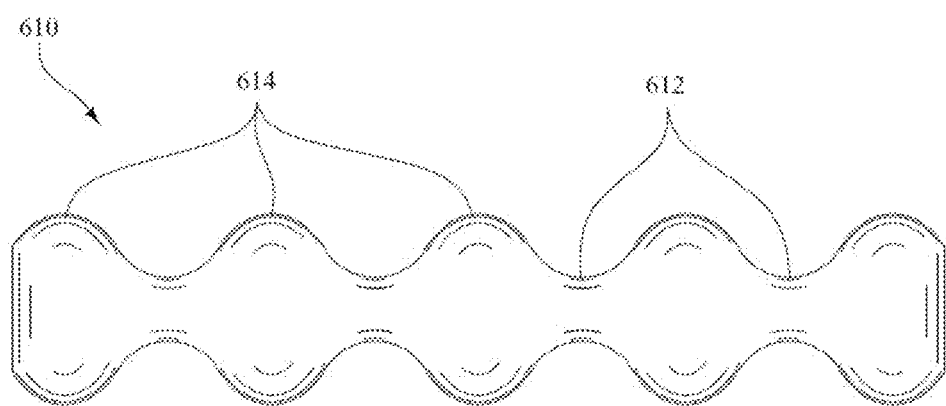
FIG. 1G is a side view of a further elongated bone particle made in accordance with the presently-disclosed subject matter.

In the embodiment shown in FIG. 1F, the bone particle 510 includes three enlarged portions 514. However, it is further contemplated that any number of enlarged portions can be included in a specially-shaped bone particle to produce bone particles of varying lengths without departing from the spirit and scope of the subject matter described herein. For instance, and as shown in FIG. 1G, an elongated bone particle 610 is provided that resembles a number of dumbbell-shaped bone particles placed end-to-end and includes five enlarged, spherical portions 614 and a plurality of center portions 612 aligned along a common longitudinal axis, where each of the enlarged portions 614 also extend laterally away from the common longitudinal axis of each center portion 612, and where each of the center portions 612 are also interposed between respective enlarged portions 614.

In some embodiments of the presently-disclosed subject matter, the interconnectedness of the bone particles also increases the compressive, bending, tensile, and shear strength of the bone graft compositions (i.e., the combination of particles and cement) by providing direct loading pathways through contacting other bone particles, which are stronger than the cement matrix. In this regard, in some embodiments, the interconnectedness of the bone particles is increased by each particle having larger dimensions at its ends compared to its center. For example, the inclusion of bone particles having a dumbbell shape, as described above, or a shape in the form of a capital "I" will have an increased connection to adjacent bone particles when compared to bone particles having a shape in the form of a capital "O," assuming both shapes have similar length and width.

Figure 19:
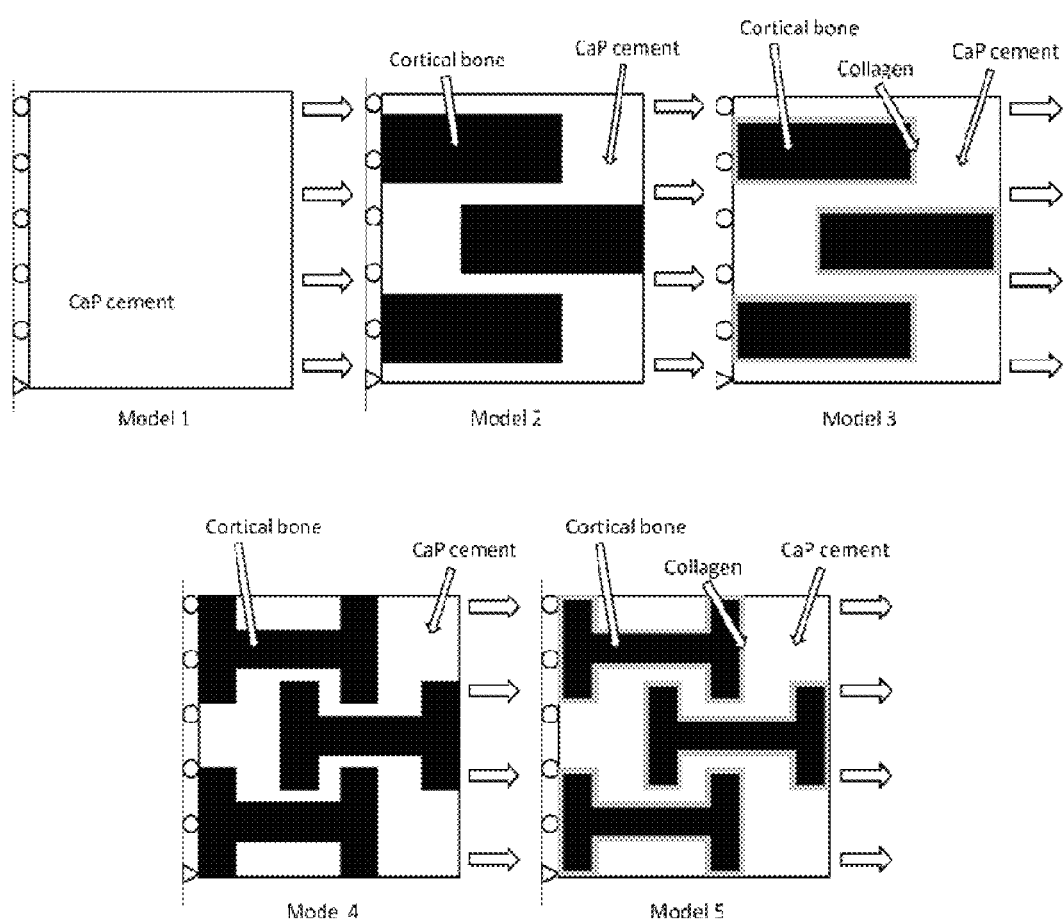
FIG. 19 is a schematic diagram showing the various models used to determine the mechanical behavior effects of shaped cortical bone particles in calcium phosphate cement, including a model that contained calcium phosphate cement only (Model 1); a model that contained cylindrical cortical bone particles in calcium phosphate cement (Model 2); a model that contained demineralized, cylindrical cortical bone particles in calcium phosphate cement (Model 3); a model that contained dumbbell-shaped cortical bone particles in calcium phosphate cement (Model 4); and a model that contained demineralized, dumbbell-shaped cortical bone particles in calcium phosphate cement (Model 5)

In some embodiments, the interconnecting of the bone particles allows the particles to increase their resistance to relative elongation displacement, including when they are embedded in a hardened cement. In some embodiments, the bone particles are further configured to interdigitate with the biologically-resorbable cement such that the strength and mechanical benefits of the presently-disclosed bone graft compositions are further increased. By including interconnecting bone particles in a bone graft composition, the bone particles are able to, in some embodiments, interlock and strengthen the bone graft compositions by the "keystoning" of the cement matrix, a term which is used herein to describe the conversion of tension in the shaped particles to compression in the cement matrix because of the direct interaction between the particle surfaces and the cement contacting surfaces. For an illustration and further guidance regarding keystoning of a cement matrix, see, e.g., FIGS. 18 and 19.

Additionally, the interconnecting of the bone particles also contribute to the enhanced incorporation, remodeling, and resorption of the bone graft compositions when the compositions are placed in a bone defect in vivo by extending three-dimensionally throughout the bone graft composition and bone defect site, and increasing the likelihood that the bone particles communicate not only with one another, but with the fluids and cells outside the cement surface. In other words, by including bone particles having an interconnecting shape in a bone graft composition, portions of the bone particles are capable of extending throughout the composition and into and through the outer surface of the cement structure that is formed when the bone graft composition sets into a solid structure in vivo, which, in turn, allows the composition to be accessible to cells and fluids (e.g., blood supply) from the subject and, ultimately, allows the bone graft composition to be incorporated into a subject.

For a bone graft composition to achieve the objective of becoming completely incorporated into a subject once it is placed in a bone defect, the bone graft composition must generally be rapidly remodeled and replaced with living bone in as short of time as possible, or remodeled such that a new trabecular architecture is restored within the geometry formed by the hardened cement having an interconnected network of included bone graft shapes. As such, it is thought that, not only must the bone graft composition be completely incorporated into a host, but the bone particles included in the composition must achieve a "cross-sample bioconnectivity," where the bone particles extend through the composition, once it is placed at the site of a bone defect, and communicate with each other and the outer surface of the bone graft composition to allow access to the grafted region by various cells and fluid from the subject. In this regard, it is also generally thought that as much bone material (i.e., bone particles) should be incorporated into a cement-based bone graft composition as possible and that the bone material should be readily accessible to the cells of a subject and the blood supply of a subject. However, the inclusion of an excessive amount of bone material in a cement-based bone graft composition frequently leads to a bone graft composition that does not exhibit the required mechanical stability and that does not allow the cement to behave like a cement in terms of the handling, flowability, and setting characteristics. Conversely, the inclusion of too little an amount of bone material in a cement-based bone graft composition often leads to a bone graft composition that is not sufficiently incorporated into a subject.

It has been experimentally observed, however, that the bone graft compositions of the presently-disclosed subject matter, which make use of bone particles having interconnecting shapes, are capable of optimizing the cross-sample bioconnectivity of the bone graft composition, while still preserving the mechanical stability of the bone graft composition itself (see, e.g., FIGS. 44A-44DD, showing images of serial sections of a bone graft composition, where, from one image to the next, the bone particles and, more specifically, the outer demineralized layers (shown in white) of the bone particles can be seen to connect to one another and to the outer surface of the cement (shown in black)). In particular, it has been determined that the interconnecting bone particles allow for an increased amount of cement to be present in the compositions, as compared to cement-based compositions that include only simple-shaped bone particles (e.g., cylindrical or spherical bone particles), such that the presently-disclosed bone graft composition is able to behave like a cement in terms of its handling, flowability, and setting characteristics. However, it has also been determined that by including the bone particles having an interconnecting shape in the presently-disclosed bone graft compositions, the compositions are allowed to behave as a cement while the bone particles provide an interlocking mechanical construct that augments the mechanical properties of the final cement volume once it has been administered to and has set up at the site of a bone defect. In some embodiments, the cross-sections of the processed bone particles described above may be substantially round, elliptical, square, rectangular, triangular, or have another prismatic shape such that the bone particles are able to further strengthen the cement in shear, tension, and bending loading modes as compared to the cement in its uncomposited form or as compared to cement that includes randomly-shaped and/or randomly-oriented particles. In some embodiments of the presently-disclosed bone graft compositions, the interconnecting bone particles are combined with the biologically-resorbable cement at a concentration of about 1 percent, about 2 percent, about 3 percent, about 4 percent, about 5 percent, about 6 percent, about 7 percent, about 8 percent, about 9 percent, about 10 percent, about 11 percent, about 12 percent, about 13 percent, about 14 percent, about 15 percent, about 20 percent, about 25 percent, about 30 percent, about 35 percent, about 40 percent, about 45 percent, about 50 percent by volume of the bone graft composition. In some embodiments, the interconnecting bone particles are combined with the biologically-resorbable cement at a concentration of about 1 percent to about 50 percent by volume of the bone graft composition. In some embodiments, the interconnecting bone particles are combined with the biologically-resorbable cement at a concentration of about 1 percent to about 15 percent by volume of the bone graft composition.

In some embodiments, the interconnecting bone particles of the presently-disclosed subject matter allow for an increased incorporation and remodeling of the bone graft composition, as compared to cement-based compositions that include only simple-shaped bone particles (e.g., cylindrical or spherical bone particles), by providing bone particles having an increased surface area. As will be recognized by those skilled in the art, the formation and infiltration of new bone at the site of a bone graft is a surface-driven phenomenon with the surface topology of the graft being capable of encouraging or hindering new bone from populating the graft site. By providing bone particles having an interconnecting shape, the interconnecting bone particles generally provide a greater surface area and off-axis span, as compared to bone particles having a simple shape such as a sphere or cylinder, which increases the likelihood of multiple bone particles touching and interconnecting and interlocking with each other in the composition, and also increases the osteoconductivity and osteoinductivity of the compositions. In this regard, the inclusion of the interconnecting bone particles in a bone graft composition results in a network of interconnected pathways or channels that allow for cells and fluids from the subject to infiltrate the bone graft composition and the bone graft itself, leading to the incorporation of the bone graft composition and its replacement with living bone from the subject. In other words, in some embodiments, the interconnecting bone particles can convey the host fluids and cells into the interior of the bone graft composition in order to allow resorption and new bone formation throughout the material, rather than only on its most exterior surface.

In some embodiments, the infiltration and activity of cells and fluids from the subject depends, at least in part, on the type of bone that is used to fabricate the bone particles of the presently-disclosed subject matter. In some embodiments, the processed bone particles comprise cancellous bone particles that are capable of creating a pathway through the bone graft composition and the bone graft without the need to modify their surface prior to including the cancellous bone particles in the composition. As would be recognized by those skilled in the art, cancellous or spongy bone is comprised of collagenous trabeculae and is typically less dense than cortical bone. As such, when cancellous bone is used to fabricate a bone particle having a interconnecting shape, the trabeculae provide tunnel-like spaces in the bone particles that can be used by the cells and fluids of the subject to infiltrate the bone graft and cause the incorporation and resorption of the bone graft composition.

In other embodiments of the presently-disclosed bone graft compositions, the processed bone particles are comprised of cortical bone. In these embodiments, the outer surface of cortical bone is typically first demineralized to provide a means to facilitate the movement of cells and fluids to the interior of the bone graft. The term "demineralized" is used herein to refer to the process by which bone mineral or the inorganic portion of the bone is removed to thereby expose the collagen portion of the bone. In this regard, in some embodiments, to prepare a bone particle of the presently-disclosed subject matter (e.g., a cortical bone particle), a demineralization process can be used such that the outer surface of the bone is transformed into an exposed collagen layer that is then capable of stimulating and facilitating the infiltration and activity of cells and fluid from the subject into the bone graft. In some embodiments, the processed bone particles are about 5%, about 10%, about 15%, about 20%, about 25%, about 30%, about 35%, about 40%, about 45%, about 50%, about 55%, about 60%, about 65%, about 70%, about 75%, about 80%, about 85%, to about 90% demineralized. In some embodiments, by demineralizing the bone particles, the speed with which the bone graft composition is incorporated, remodeled, or resorbed into the subject and replaced by living bone is increased, while the bone graft composition maintains and improves the strength of the subject's bone and the graft itself. In some embodiments, if the processed bone particles are not from an autograft source, the demineralization of the processed bone particles can increase the rate at which the bone graft composition is incorporated into the subject and replaced with living bone from the subject.

As noted above, in some embodiments that make use of bone particles having a demineralized layer, the interconnectedness of the bone particles of the presently-disclosed subject matter further increases the interconnectedness of the osteoinductive demineralized layers covering each particle. In this regard, in certain embodiments, the interconnected network of demineralized bone matrix (DBM) is oriented to resemble a restored trabecular architecture in the incorporating cement material mass, and the specific thickness of the demineralized layer can aid in the osteoconductivity of the end product. In some embodiments, the formation of a demineralized layer, while providing a pathway for the stimulation of activity and the infiltration of cells and fluid into the grafted region, as well as rapid resorption of the bone graft composition, also allows for the addition of an osteoinductive material, an osteogenic material, or both to the surface of the bone particles to thereby further enhance the incorporation of the bone graft composition into the subject and its replacement with living bone from the subject.

The term "osteoinductive material" is used herein to refer to any material that stimulates the migration or differentiation of bone cells to grow and become active at a graft site, while the term "osteogenic material" is used herein to refer to any material that is capable of directly or indirectly contributing to the action of osteoblasts or other cells capable of contributing to new bone growth. In some embodiments, the osteoinductive material that is added to the demineralized bone particles is selected from protein growth factors such as bone morphogenetic proteins (BMPs) and other proteins from the transforming growth factor-beta superfamily. In some embodiments, the osteogenic materials that can be added to the demineralized bone particles include host cells (e.g., osteoblasts, etc.) or stem cells or progenitor cells.

To add an osteoinductive and/or an osteogenic agent to the exposed collagen surface of a demineralized bone particle, the processed bone particles can be soaked in a solution containing the osteoinductive agent, the osteogenic agent, or both, prior to mixing the demineralized bone particles with the biologically-resorbable cement, such that the osteoinductive and/or osteogenic agent simply incorporates into and adheres to the collagen surface. Of course, a number of other methods for linking such an agent to a protein such as collagen are known to those of ordinary skill in the art and can be used without departing from the spirit and scope of the subject matter described herein.

In some embodiments, stem cells can further be added to the bone particles to enhance the incorporation of the bone graft composition into the subject and its replacement with living bone from the subject. As used herein, the term "stem cells" refers broadly to traditional stem cells, progenitor cells, preprogenitor cells, precursor cells, blood cells, platelets, reserve cells, and the like. Exemplary stem cells include, but are not limited to, embryonic stem cells, adult stem cells, pluripotent stem cells, neural stem cells, muscle stem cells, muscle precursor stem cells, endothelial progenitor cells, bone marrow stem cells, chondrogenic stem cells, lymphoid stem cells, mesenchymal stem cells, hematopoietic stem cells, and the like. Descriptions of stem cells, including methods for isolating and culturing them, may be found in, among other places, Embryonic Stem Cells, Methods and Protocols, Turksen, ed., Humana Press, 2002; Weisman et al., Annu Rev. Cell. Dev. Biol. 17:387-403; Pittinger et al., Science, 284:143-47, 1999; Animal Cell Culture, Masters, ed., Oxford University Press, 2000; Jackson et al., PNAS 96(25):14482-86, 1999; Zuk et al., Tissue Engineering, 7:211-228, 2001; and U.S. Pat. Nos. 5,559,022, 5,672, 346 and 5,827,735.

In addition to adding various osteoinductive or osteogenic agents, such as stem cells, to the bone particles of the presently-disclosed subject matter, it is further contemplated that a number of additional therapeutic agents can also be added directly to the biologically-resorbable cement prior to mixing it with the processed bone particles. Without wishing to be bound by any particular theory, it is contemplated that the accelerated remodeling and incorporation of the cement due to the presence of the processed bone particles can facilitate a more rapid and more complete release of a therapeutic agent into the subject at the implantation site.

Further therapeutic agents that can be added to the biologically-resorbable cement prior to or after mixing it with the processed bone particles include, but are not limited to: collagen and insoluble collagen derivatives; hydroxyapatite; bisphosphonates and/or other anti-osteoporosis drugs; antiviricides, such as those effective against HIV and hepatitis; amino acids, peptides, vitamins, and/or co-factors for protein synthesis; hormones; endocrine tissue or tissue fragments; synthesizers; enzymes, such as collagenase, peptidases, oxidases; polymer cell scaffolds with parenchymal cells; angiogenic drugs and polymeric carriers containing such drugs; collagen lattices; biocompatible surface active agents; antigenic agents; cytoskeletal agents; cartilage fragments; living cells, such as chondrocytes, bone marrow cells, mesenchymal stem cells; natural extracts; tissue transplants; bioadhesives; transforming growth factor (TGF-beta); insulin-like growth factor (IGF-1); parathyroid hormone; growth hormones, such as somatotropin; bone digesters; antitumor agents; fibronectin; cellular attractants and attachment agents; immuno-suppressants; and, permeation enhancers, e.g. fatty acid esters such as laureate, myristate and stearate monoesters of polyethylene glycol, enamine derivatives, and alpha-keto aldehydes.

In some embodiments, an antibiotic is added to the biologically-resorbable cement (e.g., the biologically-resorbable cement powder) prior to mixing it with the processed bone particles of the presently-disclosed subject matter. Various antibiotics can be employed in accordance with the presently-disclosed subject matter including, but are not limited to: aminoglycosides, such as amikacin, gentamycin, kanamycin, neomycin, netilmicin, paromomycin, streptomycin, or tobramycin; carbapenems, such as ertapenem, imipenem, meropenem; chloramphenicol; fluoroquinolones, such as ciprofloxacin, gatifloxacin, gemifloxacin, grepafloxacin, levofloxacin, lomefloxacin, moxifloxacin, norfloxacin, ofloxacin, sparfloxacin, or trovafloxacin; glycopeptides, such as vancomycin; lincosamides, such as clindamycin; macrolides/ketolides, such as azithromycin, clarithromycin, dirithromycin, erythromycin, or telithromycin; cephalosporins, such as cefadroxil, cefazolin, cephalexin, cephalothin, cephapirin, cephradine, cefaclor, cefamandole, cefonicid, cefotetan, cefoxitin, cefprozil, cefuroxime, loracarbef, cefdinir, cefditoren, cefixime, cefoperazone, cefotaxime, cefpodoxime, ceftazidime, ceftibuten, ceftizoxime, ceftriaxone, or cefepime; monobactams, such as aztreonam; nitroimidazoles, such as metronidazole; oxazolidinones, such as linezolid; penicillins, such as amoxicillin, amoxicillin/clavulanate, ampicillin, ampicillin/sulbactam, bacampicillin, carbenicillin, cloxacillin, dicloxacillin, methicillin, mezlocillin, nafcillin, oxacillin, penicillin G, penicillin V, piperacillin, piperacillin/tazobactam, ticarcillin, or ticarcillin/clavulanate; streptogramins, such as quinupristin/dalfopristin; sulfonamide/folate antagonists, such as sulfamethoxazole/trimethoprim; tetracyclines, such as demeclocycline, doxycycline, minocycline, or tetracycline; azole antifungals, such as clotrimazole, fluconazole, itraconazole, ketoconazole, miconazole, or voriconazole; polyene antifungals, such as amphotericin B or nystatin; echinocandin antifungals, such as caspofungin or micafungin, or other antifungals, such as ciclopirox, flucytosine, griseofulvin, or terbinafine. In some embodiments, the antibiotic that is included in a bone graft composition of the presently-disclosed subject matter is vancomycin. For further explanation and guidance regarding the use of cements, such as calcium phosphate cements, as drug delivery systems, see, e.g., Verron, et al. Drug Discovery Today. 15(13/14): 547-552 (2010).

As one particular example of adding a therapeutic, osteoinductive material to a bone graft composition of the presently-disclosed subject matter, bone morphogenetic protein 2 (BMP-2) can be mixed with the biologically-resorbable cement at a ratio of 0.17 mg BMP-2 for every 1 g of cement. As another particular example of the addition of a therapeutic agent to a bone graft composition of the presently-disclosed subject matter, 30 mg of a desired antibiotic, such as vancomycin, can be added per gram of cement and can be mixed in powder form directly with the resorbable cement powder prior to implantation. As yet another particular example of adding a therapeutic osteogenic agent to a bone graft composition of the presently-disclosed, a bisphosphonate can be added for local bone quality improvement and preservation in a manner that has distinct advantages over other approaches. In this regard, in some embodiments, the bisphosphonate can be mixed directly with the powder components of the cement so that it is evenly distributed with the final set cement mass, and causing the release of the bisphosphonate to be dependent on the rate of cement resorption by osteoclasts and the subsequent deposition of the bisphosphonate in any newly formed bone nearby. In other embodiments, the bisphosphonate can be mixed with a processed allograft bone particle of the composite cement so that it primarily resides at discrete locations in the graft and, in particular, on the surface of the graft particles. In this case, as opposed to including the bisphosphonate in the cement itself, the bisphosphonate would be rapidly released and delivered to the local region as new bone forms in response to the bone grafting procedure. Any new bone, thus formed, would be infused with the bisphosphonate drug and would be more readily preserved relative to normal bone. In yet other embodiments, the bisphosphonate can be mixed with both the cement powder and the bone particles to obtain both of the beneficial effects of the approaches outline above.

Further provided, in some embodiments of the presently-disclosed subject matter, are methods for treating a bone defect. In some embodiments, a method for treating a bone defect is provided that comprises the steps of: providing a bone graft composition of the presently-disclosed subject matter; and administering an effective amount of the bone graft composition to a bone defect site in a subject.

As used herein, the terms "treatment" or "treating" relate to any treatment of a bone defect, including, but not limited to, prophylactic treatment and therapeutic treatment. As such, the terms "treatment" or "treating" include, but are not limited to: preventing a bone defect or the development of a bone defect; inhibiting the progression of a bone defect; arresting or preventing the development of a bone defect; reducing the severity of a bone defect; ameliorating or relieving symptoms associated with a bone defect; and causing a regression of the bone defect or one or more of the symptoms associated with the bone defect.

The term "bone defect" is used herein to refer to any imperfection or discontinuity in the structure of a bone. For example, in some embodiments, the bone defect site is a bone void, or, in other words, an empty space that is typically occupied by bone. As another example, in some embodiments, the bone defect is a bone fracture or a break in the continuity of a bone. As yet another example, in some embodiments, the bone defect site is a site of an intended bone fusion, such as sites where portions of bone are rubbing against one another.

For administration of a bone graft composition disclosed herein, the bone graft compositions are typically administered in an amount sufficient to fill the site of the bone defect, i.e., an "effective amount." Of course, the optimum amount of a bone graft composition used to fill a bone defect will vary depending on the size and/or shape of the particular bone defect being filled. However, determination and adjustment of the amount of a bone graft composition to be used in a particular application, as well as when and how to make such adjustments, can be ascertained using only routine experimentation.

Figure 45A:
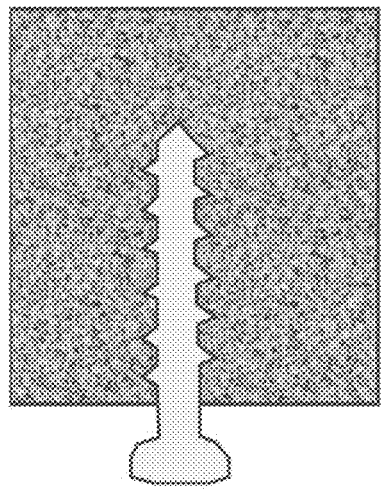
FIGS. 45A-45E are schematic diagrams showing: a screw placed in cancellous bone (FIG. 45A); a screw placed in cancellous bone, where the placement of the screw is augmented with cement (FIG. 45B); a failure of a screw placed in a cancellous bone, where the placement of the screw was augmented with cement, and where the failure occurs at the interface of the cancellous bone and the cement (FIG. 45C); a failure of a screw placed in a cancellous bone, where the placement of the screw was augmented with cement, and where the failure occurs via shear force at the interface of the screw and the cement (FIG. 45D); and a screw placed in cancellous bone, where the placement of the screw is augmented with cement and processed bone particles having a shape as shown in FIG. 1A, and where the processed bone particles bridge across and strengthen both the screw-cement and cement-bone interfaces (FIG. 45E)
Figure 45B:
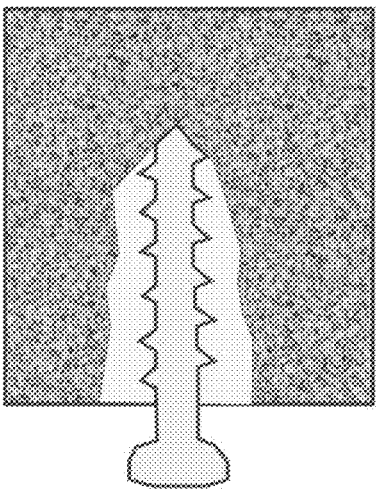
Figure 45C:
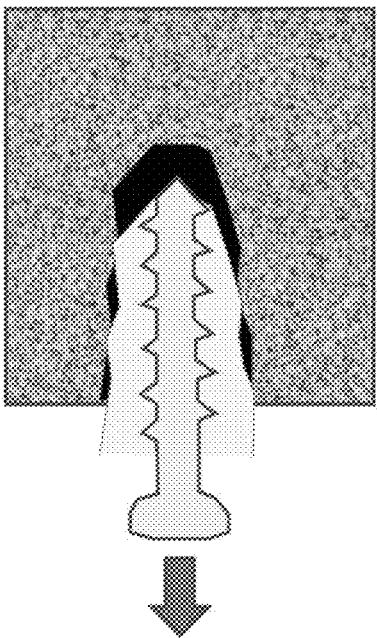
Figure 45D:
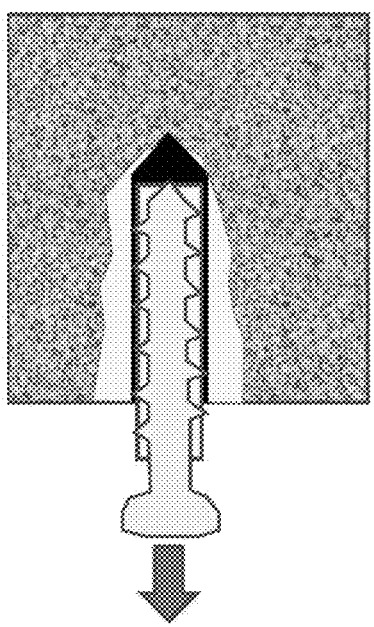
Figure 45E:
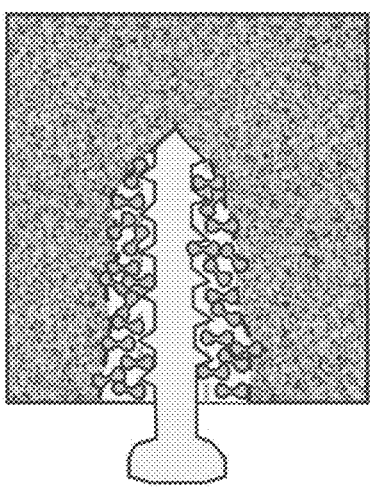
Figure 46:
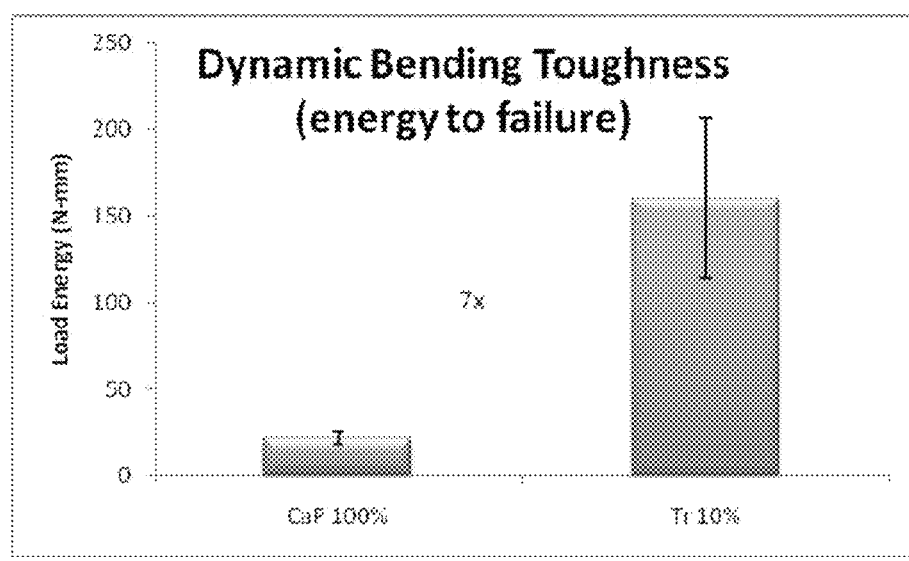
FIG. 46 is a graph showing the results of a dynamic bending toughness test performed to analyze the bending toughness of: a pure calcium phosphate cement (CaP 100%) comprised of tetracalcium phosphate (TTCP), monocalcium phosphate (MCP), and calcium carbonate; and a bone graft composition of the presently-disclosed subject matter that includes a calcium phosphate cement comprised of TTCP, MCP and calcium carbonate and that includes 10 percent by volume of processed bone particles having a shape as shown in FIG. 1A (Tr 10).

In some embodiments of the therapeutic methods described herein, the bone graft compositions can be used in association with various other devices commonly used to treat a bone defect. It has been observed that the placement of various devices into a bone defect often fails due to the device becoming dislodged or otherwise removed from the bone or bone defect. For example, screws are often placed into a bone, either alone or in association with various cements, as shown in FIGS. 45A and 45B, respectively. However, the placement of a screw into a bone, particularly when the placement of screw into a bone is augmented with cement, frequently results in a failure of the cement composition, either at the interface of the bone and the cement, as shown in FIG. 45C, or at the interface of the screw and the cement, as shown in FIG. 45D. By using the bone graft compositions of the presently-disclosed subject matter though, it has further been observed that the processed bone particles bridge across and strengthen both the screw-cement and cement-bone interfaces FIG. 45E. As such, in some embodiments of the presently-disclosed methods for treating a bone defect, an effective amount of a bone graft composition can be administered to a site of a bone defect in a subject prior to placing a device, such as a screw, in the bone defect site.

In yet further embodiments of the presently-disclosed subject matter, kits are provided. In some embodiments, a kit is provided that includes a biologically-resorbable cement powder and a plurality of processed bone particles, where each of the processed bone particles has a shape configured to interconnect with adjacent bone particles. In some embodiments of the kits, the biologically-resorbable cement powder and the processed bone particles are packed in separate vessels or are packaged together in a single vessel.

In some embodiments, the bone particles included in the kit are lyophilized or are otherwise dehydrated. In this regard, in some embodiments, the kit further includes an aqueous vehicle for adding to the cement powder, the bone particles, or both the cement powder and bone particles. In some embodiments, the aqueous vehicle can be metered and packaged in a separate vessel such that the vessel includes a precise amount of aqueous vehicle for preparing a bone graft composition having a desired consistency. In other embodiments, the kit further comprises instructions for mixing the cement powder and the bone particles, and then combining that mixture with a prescribed amount of an aqueous vehicle such that a bone graft composition having a desired consistency is produced and can then be administered to a subject.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The presently-disclosed subject matter is further illustrated by the following specific but non-limiting examples. Some of the following examples may include compilations of data that are representative of data gathered at various times during the course of development and experimentation related to the present invention. Additionally, some of the following examples are prophetic, notwithstanding the numerical values, results and/or data referred to and contained in the examples.

EXAMPLES

Example 1

Fabrication of Planar Cortical Bone Particles

To fabricate planar cortical bone particles through the refinement of an intact bone into a larger number of separate cortical bone particles, an intact bone was first obtained, and all of the soft tissue was removed from the diaphysis of the bone, with the larger pieces of soft tissue being removed using a blade, and the periosteum and connective tissues being removed using a stainless steel wire wheel or brush. Next, the distal and proximal ends of the bone were removed with a saw, leaving only the diaphyseal region of the bone. All of the bone marrow and soft tissue inside the bone's shaft was then physically removed, and the bone was rinsed out. A reamer was used to remove any remaining cancellous bone material from the inside of the diaphyseal bone until only cortical bone remained. The resulting shaft of cortical bone was then thoroughly cleaned with detergent and deionized (DI) water, and the shaft of cortical bone was subsequently soaked in 100 percent ethanol overnight.

After the overnight ethanol bath, each shaft of bone was then dried and cut longitudinally to create 3 to 4 shanks of cortical bone that were approximately 1 inch wide. Those fabricated pieces of cortical bone were cut with the longitudinal axis of the bone material running in the same direction as the finished parts largest dimension. A surface grinder was then used to create thinned pieces of cortical bone that were 0.5 mm thick and approximately 1 to 2 inches square. That creation of thinned pieces of cortical bone was done by machining small portions of each bone shank one at a time due to the shanks' curved and organic shape. Once a 0.5 mm-thick piece of cortical bone stock was created, the bone's longitudinal direction was then labeled, and the 0.5 mm-thick pieces of bone stock were soaked in DI water under a vacuum for an hour. This allowed the material to soften or become slightly pliable and also filled all the open voids with water to minimize the amount of splintering in the subsequent stamping/punching process and to reduce waste. The 0.5 mm-thick bone stock was then removed from the DI water and its surface blotted dry. The bone was then inserted in a custom punch with care taken to insure that the longitudinal direction of the bone was in the correct orientation in the punch. The punch was then used to create a matrix of shaped cortical bone particles with a 0.5 mm thickness. A microscope with a scale was then used to measure the individual bone pieces and ensure that their size and shape were in accordance with the appropriate specifications. Typically, the cortical bone particles fabricated were 2.5 mm long and 1.5 mm wide by 0.5 mm thick.

Example 2

Fabrication of Complex Cortical Bone Particles

To fabricate more complex, three-dimensional cortical bone particles by refining an intact bone into a large number of cortical bone particles, an intact bone was first obtained, and all of the soft tissue was removed from the diaphysis of the bone, with the larger pieces of soft tissue being removed using a blade, and the periosteum and connective tissues being removed using a stainless steel wire wheel or brush. Next, the distal and proximal ends of the bone were removed with a saw leaving only the diaphyseal region of the bone. All the bone marrow and soft tissue inside the bone's shaft was then physically removed, and the bone was rinsed out. A reamer was used to remove any remaining cancellous bone material from the inside of the diaphyseal bone until only cortical bone remained. The resulting shaft of cortical bone was then thoroughly cleaned with detergent and dionized (DI) water, and the shaft of cortical bone was subsequently soaked in 100 percent ethanol overnight.

Subsequent to the overnight ethanol bath, each shaft of bone was then dried and cut longitudinally to produce "matchstick" size shanks of bone, with each shank being 4 to 5 mm across and approximately 75 mm in length. Each of these "matchsticks" of cortical bone was then fixed in a thimble-sized pot using an epoxy or polyester resin with care taken to be sure that the "matchstick" pieces of bone potted concentric with the center of the pot. Once the bone material was fixed in a pot, a turning operation was then used to create the "dumbbell" like shapes (see, e.g., FIGS. 1A-1C). Briefly, each pot containing the bone material was mounted in a lathe, but, instead of a traditional cutter as is commonly used in lathe operations, a thin abrasive disk (approximately 0.5 mm thick) was used to shape the bone particles as the abrasive disk prevented splintering of the bone material. During the lathing procedure, the abrasive disk was used to cut the bone material perpendicular to the rotation of the bone material in the lathe. Once the dumbbell-shaped bone particles were formed, a microscope was then used in conjunction with a scale to ensure the bone particles were of the appropriate size and dimensions. For most applications, dumbbell-shaped bone particles were fabricated that were about 2.5 mm long, 1.5 mm diameter at the ends and 0.5 mm diameter in the center portion.

Example 3

Partial Demineralization of Cortical Bone

To partially demineralize the fabricated cortical bone particles by removing the calcium from the surface of the particles, 9.0 to 10.0 g of clean, defatted, cortical bone particles were first placed in a 1000 ml glass beaker with a magnetic stir bar. Approximately 600 ml of 0.05N HCl was then added to the container to ensure a sufficient volume of acid was present to prevent neutralization during the demineralization process. The acid solution containing the cortical bone particles was then stirred for 90 min using a magnetic stir bar to facilitate proper mixing. After 90 min, the bone particles were then allowed to settle out in the solution, and the acid was poured off by using a thin mesh, stainless steel wire strainer. The bone pieces were then immediately washed with DI water until the pH was neutralized. Subsequently, the bone pieces were dried for several hours in a dehydrator/oven at a temperature of approximately 100° F. (38° C.). Further measurements of the decalcified layer, using a light microscope and a scanning electron microscope (SEM) to examine the surface morphology of the acid-soaked rods, revealed that the procedure resulted in approximately 10% decalcification of each piece of bone.

Example 4

Analysis of Bending Strength of Calcium Phosphate (Tetracalcium Phosphate/Monocalcium Phosphate/Calcium Carbonate)-based Bone Graft Composition To assess the bending strength of a calcium phosphate cement comprised of a mixture of tetracalcium phosphate, monocalcium phosphate, and calcium carbonate powder and augmented with specially-shaped cortical bone particles, mechanical testing experiments using such a calcium phosphate cement with various amounts of partially-demineralized, shaped cortical bone particles were undertaken to determine the mechanical behavior effects of adding various amounts of the specially-processed cortical bone particles to the exemplar calcium-based cement. Briefly, in these experiments, a calcium phosphate cement consisting of tetracalcium phosphate (TTCP) powder, monocalcium phosphate (MCP) powder, and calcium carbonate powder was used and was prepared by mixing the powder mixture with water in a 2.6:1 powder to water ratio by weight to form a paste, which was then capable of setting within fifteen minutes into a solid mass.

Similar to the methodology described herein above, cortical bone particles were then created through a machining process that yielded specially-shaped particles approximately 2.5 mm in length, 1.5 mm in width at each end, and 0.5 mm thickness on average with a 0.5 mm wide central portion (see, e.g., FIG. 1A). These bone particles were obtained from the diaphyseal regions of porcine femora and tibae and were partially demineralized using the methodology described above. After the particles were formed and dehydrated, they were then weighed and added to the premixed cement powder in volume ratios of 10.0% and 20.0%. The dry components of cement powders and dry bone particles were then thoroughly mixed.

For purposes of comparison, calcium phosphate mixtures were also made using non-specially shaped cortical bone particles of similar size to those described above. The non-specially shaped particles were produced by grinding 0.5 mm thick scrap bone that was produced during the fabrication of the shaped bone particles. The scrap bone was ground in a rotary mill to produce a variety of particle sizes that were sorted using two sieves over multiple passes to produce particles between 1.75 mm and 0.5 mm particle size dimensions. These particles were also partially demineralized as described above and dehydrated before being added to the calcium phosphate powder, and were thoroughly mixed to produce approximate volume ratios of 10% and 40%.

Subsequent to the formation of the powders and the bone particles, test samples were then created by combining the dry bone and cement materials with an appropriate amount of distilled water (2.6:1 ratio of calcium phosphate powder to water by weight), mixing with a thin metal spatula until a consistent wet paste was formed. Next, the materials were spread into cylindrical Teflon® (Du Pont de Nemours and Company Corporation, Wilmington, Del.) molds that were designed to create test samples 20 mm in length with a diameter of 8 mm.

Figure 3:
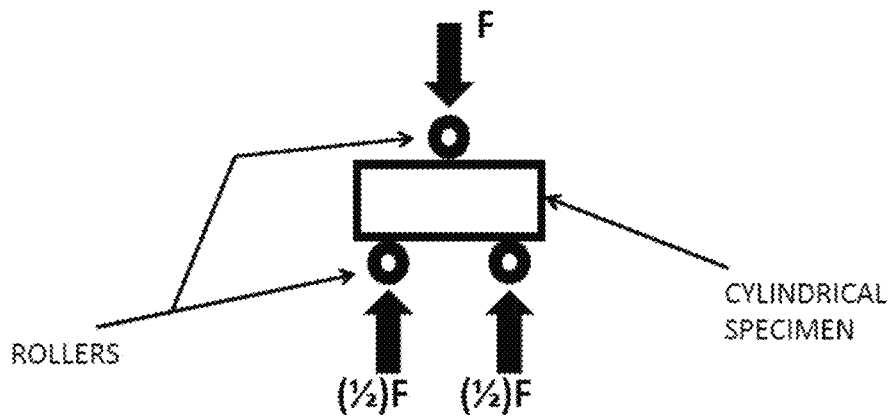
FIG. 3 is a schematic diagram showing an experimental three-point bending fixture used to apply a force (F) and assess the bending strength of a hardened bone graft composition (cylindrical specimen) made in accordance with the presently-disclosed subject matter.

The bending test was then performed using a three-point bending fixture with an 11 mm support span and a central radiused "blade" that applied a load to the top of the horizontally oriented specimen at a rate of 0.1 in/min (2.54 mm/min), as depicted in FIG. 3. The maximum force achieved prior to the first failure of the sample resulting in a 40% reduction in applied load or a significant change in specimen stiffness was recorded. The failure stress was calculated as the flexural strength based on the applied bending load and the sample geometry using the formula $\sigma = Mc/I$, where I is the area moment of inertia of the circular cross-section of the sample.

TABLE 1

Bending Strength (MPa) of Calcium Phosphate (Tetracalcium Phosphate/Monocalcium Phosphate/Calcium Carbonate)-Based Bone Graft Compositions

|  | CaP 100% | Tr 10% | Tr 20% | Alt 10% | Alt 40% |
|---|---|---|---|---|---|
| Mean | 4.4 | 8.1 | 6.4 | 7.9 | 3.5 |
| Std. Dev. | 1.3 | 1.9 | 1.1 | 2.2 | 0.9 |
| P |  | <0.005 | <0.01 | <0.005 | NS |

Figure 4:
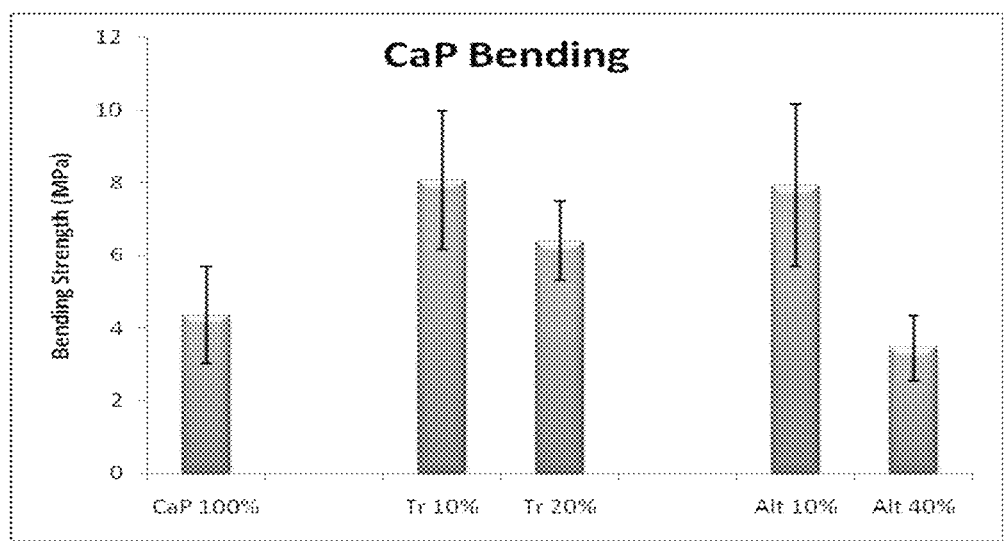
FIG. 4 is a graph showing the results of a bending test performed with a three-point bending fixture as shown in FIG. 3 to analyze the bending strength of: a pure, calcium phosphate cement (CaP 100%) comprised of tetracalcium phosphate (TTCP); monocalcium phosphate (MCP), and calcium carbonate; a bone graft composition of the presently-disclosed subject matter that includes a calcium phosphate cement comprised of TTCP, MCP and calcium carbonate and that includes 10 percent or 20 percent by volume of processed bone particles having a shape as shown in FIG. 1A (Tr 10% and Tr 20%, respectively); and a bone graft composition that includes a calcium phosphate cement comprised of TTCP, MCP and calcium carbonate and that includes 10 percent or 40 percent by volume of non-specially shaped bone particles (Alt 10% and Alt 40%, respectively)

As shown in FIG. 4 and Table 1, upon analysis of the results from these experiments, it was observed that adding specially-shaped and partially demineralized bone particles (Tr) to a calcium phosphate cement significantly improve the mechanical properties of the cement in the demanding loading mode of bending. In other words, the foregoing results demonstrated that an osteoconductive, remodelable, resorbable, and osteoinductive material can be added to a calcium phosphate cement and can be used to increase the bending strength of the calcium phosphate cement. In contrast, when the bone particles added at 40% were non-specially shaped (Alt), the bending strength decreased significantly, as also shown in FIG. 4, thus further indicating that the mechanical behavior of bone graft compositions can be improved by the inclusion of the specially-shaped bone particles. Additionally, it was found that a higher percentage of non-specially shaped bone particles was required to be added to the cement to achieve a similar level of remodeling potential through interconnectedness as compared to the specially-shaped particles that were included at a lower percentage.

Example 5

Analysis of Bending Strength of Calcium Phosphate (Alpha-Tricalcium Phosphate/Hydroxyapatite)-based Bone Graft Composition To further assess the bending strength of calcium phosphate-based cements augmented with specially-shaped cortical bone particles, additional mechanical testing experiments using an alternative calcium phosphate cement with various amounts of partially-demineralized, specially-shaped cortical bone particles were undertaken. Briefly, in this further experiment, a commercial-grade calcium phosphate cement, including an alpha-tricalcium phosphate powder that, upon mixing with a setting solution, formed precipitated hydroxyapatite, was used. When this powder mixture was mixed with water in a 2.6:1 powder-to-water ratio by weight, a paste formed that was then capable of setting within fifteen minutes into a solid mass.

Similar to the methodology described above, cortical bone particles were then again created through a machining process that yielded specially-shaped particles approximately 2.5 mm in length, 1.5 mm in width at each end, and 0.5 mm in thickness, on average, with a 0.5 mm wide central region (see, e.g., FIG. 1A). These bone particles were once again obtained from the diaphyseal regions of porcine femora and tibae and were partially demineralized subsequent to weighing and adding the bone particles to the premixed cement powder in a volume ratio of 10.0%. The dry components of cement powders and dry bone particles were then thoroughly mixed.

Again, for purposes of comparison, calcium phosphate mixtures were also made using non-specially shaped cortical bone particles of similar size to those described above. The non-specially shaped particles were again produced using scrap bone and had particle size dimensions of between 1.75 mm and 0.5 mm. These particles were also partially demineralized as described above and dehydrated before being added to the calcium phosphate powder and thoroughly mixed to produce an approximate volume ratio 40%, as it was found in the experiments described above that a higher percentage of non-specially shaped bone particles was required to be added to the cement to achieve a similar level of remodeling potential through interconnectedness as compared to the specially-shaped bone particles included at a lower percentage.

Subsequent to the formation of the powders and the bone particles, test samples were once again created by combining the dry bone and cement materials with an appropriate amount of distilled water (2.6:1 ratio of calcium phosphate powder to water by weight), and mixing with a thin metal spatula until a consistent wet paste was formed. The materials were then again spread into cylindrical Teflon® (Du Pont De Nemours And Company Corporation, Wilmington, Del.) molds to yield test samples 20 mm in length with a diameter of 8 mm.

The bending test was again performed with these additional calcium phosphate-based samples using the three-point bending fixture described above (see FIG. 3). The maximum force achieved prior to the first failure of the sample resulting in a 40% reduction in applied load or a significant change in specimen stiffness was once more recorded, and the failure stress for these samples was subsequently calculated as the flexural strength based on the applied bending load and the sample geometry using the formula $\sigma = Mc/I$, where I is the area moment of inertia of the circular cross-section of the sample.

TABLE 2

Bending Strength (MPa) of Calcium Phosphate (Alpha-Tricalcium Phosphate/Precipitated Hydroxyapatite)-Based Bone Graft Compositions

|  | CaP* 100% | Tr 10% | Alt 40% |
|---|---|---|---|
| Mean | 3.8 | 4.2 | 2.1 |
| Std. Dev. | 1.4 | 1.2 | 0.9 |
| P |  | NS | <0.005 |

Figure 5:
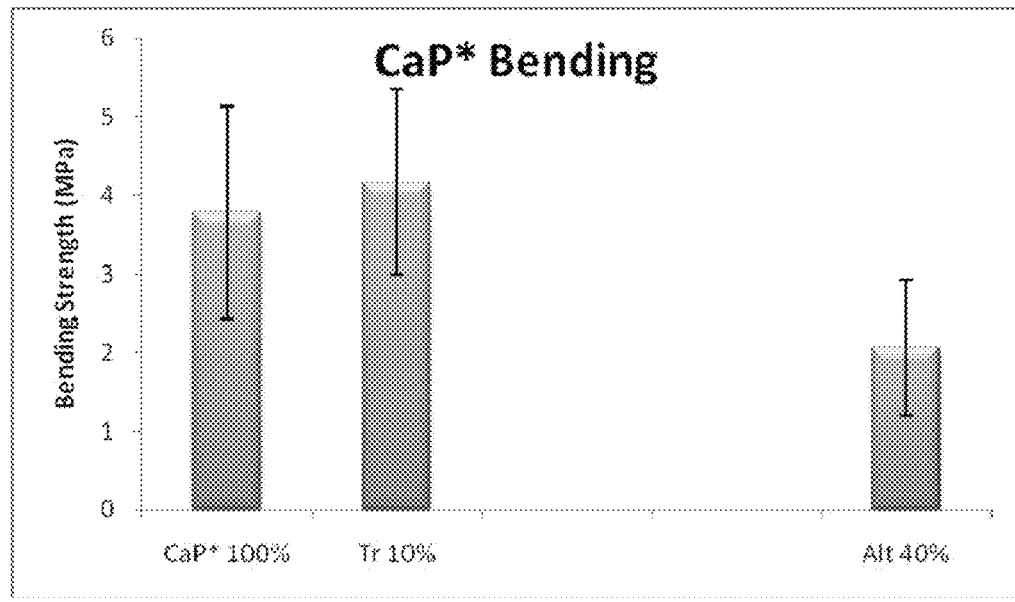
FIG. 5 is a graph showing the results of a bending test performed with a three-point bending fixture as shown in FIG. 3 to analyze the bending strength of: a pure, commercial-grade calcium phosphate cement (CaP* 100%) made from alpha-tricalcium phosphate powder; a bone graft composition of the presently-disclosed subject matter that includes a commercial-grade calcium phosphate cement made from alpha-tricalcium phosphate powder and that includes 10 percent by volume of processed bone particles having a shape as shown in FIG. 1A (Tr 10%); and a bone graft composition that includes a commercial-grade calcium phosphate cement made from alpha-tricalcium phosphate powder and that includes 40 percent by volume of non-specially shaped bone particles (Alt 40%)

As shown in FIG. 5 and Table 2, upon analysis of the results from these experiments, it was once more observed that adding specially-shaped and partially demineralized bone particles (Tr) to an alternative calcium phosphate cement, which was comprised of alpha-tricalcium phosphate/precipitated hydroxyapatite, significantly improved the mechanical properties of the cement in the demanding loading mode of bending. Similar to the experiment described above in Example 4, when the bone particles added at 40% were non-specially shaped (Alt), the bending strength decreased significantly, as shown in FIG. 5, thus further indicating that the bending strength of the calcium phosphate could be increased by utilizing specially-shaped bone particles.

Example 6

Analysis of Bending Strength of Calcium Sulfate-based Bone Graft Composition

To assess the bending strength of a non-calcium phosphate-based cement in conjunction with the presently-described, specially-shaped cortical bone particles, mechanical testing experiments using a calcium sulfate (CaS) cement with various amounts of partially-demineralized, specially-shaped cortical bone particles were also undertaken. Briefly, in this further experiment, a commercial grade CaS cement was used and was mixed with water in a 2:1 powder to water ratio by weight, such that a paste was formed that was capable of setting within twenty minutes into a solid mass.

Similar to the methodology described above, cortical bone particles were then again created through a machining process that yielded specially-shaped particles approximately 2.5 mm in length, 1.5 mm in width at each end, and 0.5 mm thickness on average with a 0.5 mm wide central region (see, e.g., FIG. 1A). These bone particles were also obtained from the diaphyseal regions of porcine femora and tibae and were partially demineralized subsequent to weighing and adding the bone particles to the premixed cement powder in a volume ratios of 10.0% and 20.0%. The dry components of cement powders and dry bone particles were then thoroughly mixed.

Again, for purposes of comparison, CaS mixtures were also made using non-specially shaped cortical bone particles of similar size to those described above. The non-specially shaped particles were again produced using scrap bone and had particle size dimensions of between 1.75 mm and 0.5 mm. These particles were also partially demineralized as described above and dehydrated before being added to the calcium phosphate powder, and were thoroughly mixed to produce approximate volume ratios of 10% and 40%, as it was found in the experiments described above that a higher percentage of non-specially shaped bone particles was required to be added to the cement to achieve a similar level of remodeling potential through interconnectedness as compared to the specially-shaped particles that were included at a lower percentage.

Subsequent to the formation of the powders and the bone particles, test samples were once again created by combining the dry bone and cement materials with an appropriate amount of distilled water (2:1 ratio of CaS powder to water by weight), and mixing with a thin metal spatula until a consistent wet paste was formed. The materials were then again spread into cylindrical Teflon® (Du Pont de Nemours and Company Corporation, Wilmington, Del.) molds to create test samples 20 mm in length with a diameter of 8 mm.

The bending test was then again performed using the three-point bending fixture described above (see FIG. 3). The maximum force achieved prior to the first failure of the sample resulting in a 40% reduction in applied load or a significant change in specimen stiffness was once more recorded, and the failure stress for these samples was subsequently calculated as the flexural strength based on the applied bending load and the sample geometry using the formula $\sigma = Mc/I$, where I is the area moment of inertia of the circular cross-section of the sample.

TABLE 3

Bending Strength (MPa) of Calcium Sulfate Based Composite Cements

|  | CaS 100% | Tr 10% | Tr 20% | Alt 10% | Alt 40% |
|---|---|---|---|---|---|
| Mean | 3.7 | 5.0 | 5.0 | 3.0 | 1.9 |
| Std. Dev. | 0.4 | 0.9 | 0.9 | 0.5 | 0.1 |
| P |  | <0.005 | <0.005 | <0.05 | <0.0005 |

Figure 6:
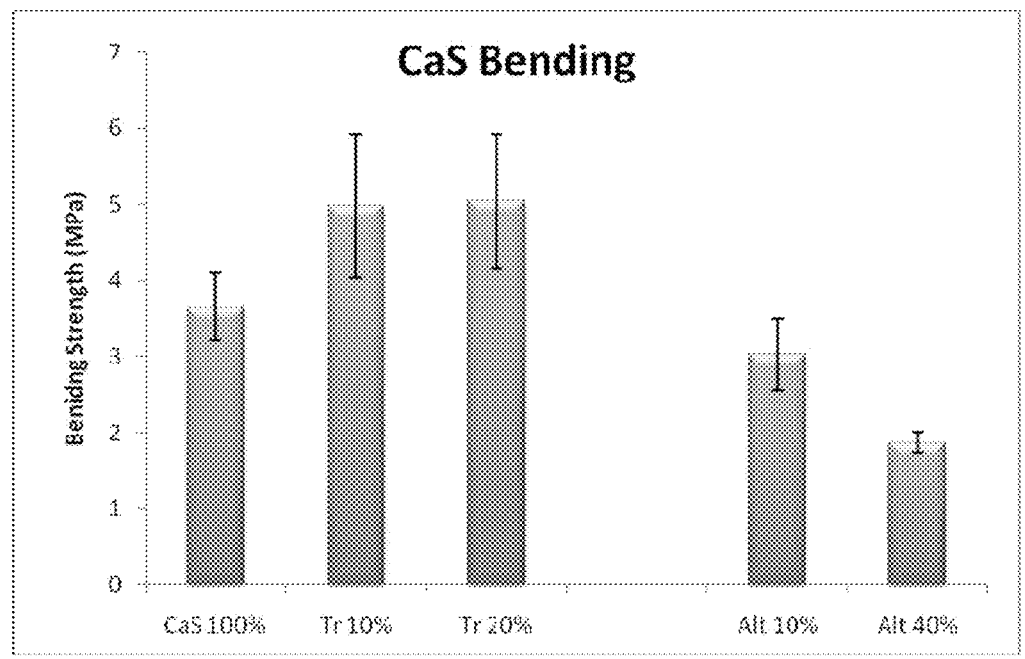
FIG. 6 is a graph showing the results of a bending test performed with a three-point bending fixture as shown in FIG. 3 to analyze the bending strength of: a pure, commercial grade calcium sulfate cement (CaS 100%); a bone graft composition of the presently-disclosed subject matter that includes a commercial-grade calcium sulfate cement and that includes 10 percent or 20 percent by volume of processed bone particles having a shape as shown in FIG. 1A (Tr 10% and Tr 20%, respectively); and a bone graft composition that includes a calcium sulfate cement and that includes 10 percent or 40 percent by volume of non-specially shaped bone particles (Alt 10% and Alt 40%, respectively)

As shown in FIG. 6 and Table 3, upon analysis of the results from these experiments, it was observed that the addition of specially-shaped and partially demineralized bone particles (Tr) to a different calcium-based cement, namely a CaS cement, also significantly improved the mechanical properties of the cement in the demanding loading mode of bending, demonstrating that an osteoconductive, remodelable, resorbable, and osteoinductive material can be added to a CaS cement and used to increase the bending strength of the CaS cement by utilizing bone particles having specialized shapes. Similar to the experiment described above in Examples 4 and 5, when the bone particles added at 10% and 40% were non-specially shaped (Alt), the bending strength decreased significantly, as shown in FIG. 6.

Example 7

Analysis of Bending Strength of Calcium Sulfate-based Bone Graft Composition Including Elongated Cortical Bone Particles To assess the bending strength of a calcium-based cement augmented with specially-shaped cortical bone particles having a different shape than those described above, mechanical testing experiments were undertaken using calcium sulfate (CaS) cement with a ten percent (10%) amount of partially-demineralized cortical bone particles that were shaped in an elongated fashion, which was designed to mimic a chain of independent, discrete supporting structures. In these experiments, commercially available CaS powders were mixed with water in a 2:1 powder to water ratio by weight, such that a paste was formed that was capable of setting within twenty minutes into a solid mass. Unlike the methodology described above, the cortical bone particles in these experiments were created through the machining process to yield specially-shaped particles that were approximately 10 or 14.5 mm in length, 1.5 mm in width at each end, and 0.5 mm thickness on average with a 0.5 mm wide center portion (FIG. 1G). These bone particles were also obtained from the diaphyseal regions of porcine femora and tibae and were partially demineralized using the methodology described above such that a flexible elongated structure was created. After the particles were formed and dehydrated, the particles were then weighed and added to the premixed cement powder in a 10% volume ratio. The dry components of cement powders and dry bone particles were then thoroughly mixed. For comparison purposes, a 100% CaS cement control was also created using the same described powder and water in a 2:1 ratio by weight.

Subsequent to the formation of the powders and the bone particles, test samples were then created by combining the dry materials with the appropriate amount of distilled water (2:1 ratio of CaS powder to water by weight), and mixing with a spatula until a consistent wet paste was formed. Next, the materials were spread into cylindrical Teflon® (Du Pont de Nemours and Company Corporation, Wilmington, Del.) molds designed to create test samples 20 mm in length with a diameter of 8 mm.

Similar to the experiments described above, the bending test was then performed using a three-point bending fixture with an 11 mm support span and a central radiused "blade" that applied a load to the top of the horizontally oriented specimen at a rate of 0.1 in/min (2.54 mm/min). The maximum force achieved prior to the first failure of the sample resulting in a 40% reduction in applied load or a significant change in specimen stiffness was again recorded for these samples, and the failure stress was calculated as the flexural strength based on the applied bending load and the sample geometry using the formula $\sigma=Mc/I$, where I is the area moment of inertia of the circular cross-section of the sample.

Figure 7:
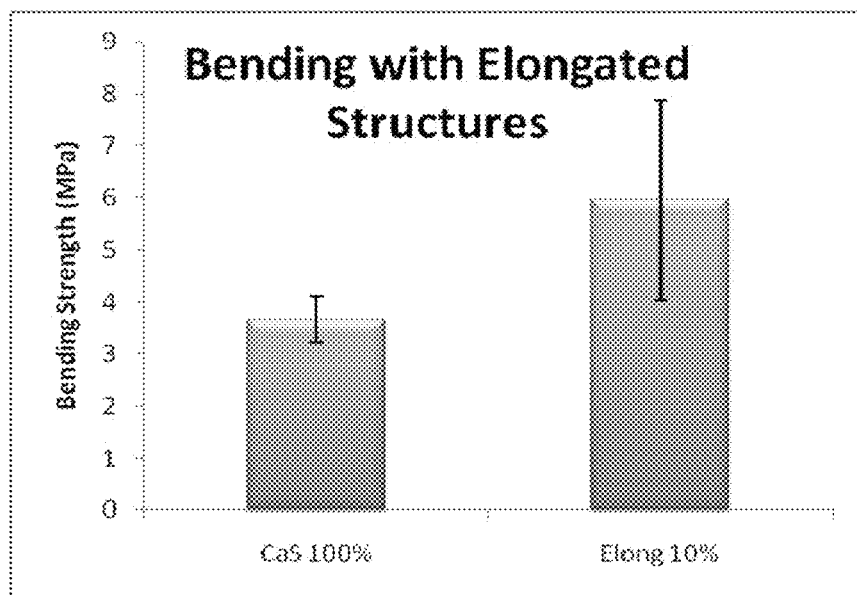
FIG. 7 is a graph showing the results of a bending test performed with a three-point bending fixture as shown in FIG. 3 to analyze the bending strength of: a pure, commercial grade calcium sulfate cement (CaS 100%); and a bone graft composition of the presently-disclosed subject matter that includes a commercial-grade calcium sulfate cement and that includes 10 percent by volume of processed bone particles having a shape as shown in FIG. 1G (Elong 10%)

The bending strength test results obtained from these experiments are depicted in FIG. 7 and in Table 4 below, where Table 4 contains the maximum force data recorded for each test during the 3-point Bending test.

TABLE 4

Bending Strength (MPa) of Calcium Sulfate Based Composite Cements Including Elongated Cortical Bone Particles.

|  | CaS 100% | Elong 10% |
|---|---|---|
| Mean | 3.7 | 6.0 |
| Std. Dev. | 0.4 | 1.9 |
| P |  | <0.005 |

Once more, the results indicated that adding specially-shaped and partially demineralized bone particles (Elong) to a CaS cement significantly improved its mechanical properties in the demanding loading mode of bending, and further indicating that the mechanical behavior of the bone graft compositions can be improved via the presence of the specially-shaped bone particles.

Example 8

Analysis of Shear Strength of Calcium Phosphate (Tetracalcium Phosphate/Monocalcium Phosphate/Calcium Carbonate)-based Bone Graft Composition To assess the shear strength of a calcium phosphate cement comprised of a mixture of tetracalcium phosphate, monocalcium phosphate, and calcium carbonate powder and augmented with specially-shaped cortical bone particles, mechanical testing experiments using such a calcium phosphate cement with various amounts of partially-demineralized, shaped cortical bone particles were also undertaken. These experiments were undertaken, at least in part, because it was believed that the mechanical properties in the demanding loading mode of shear is also important for the mechanical function of the materials when implanted in the body for control of fracture fragments. Briefly, in these experiments, a calcium phosphate cement consisting of tetracalcium phosphate (TTCP) powder, monocalcium phosphate (MCP) powder, and calcium carbonate powder was used, and was prepared by mixing the powder mixture with water in a 2.6:1 powder-to-water ratio by weight to form a paste, which was then capable of setting within fifteen minutes into a solid mass.

Similar to the methodology described above, cortical bone particles were then created through a machining process that yielded specially-shaped particles approximately 2.5 mm in length, 1.5 mm in width at each end, and 0.5 mm thickness on average with a 0.5 mm wide center portion (see, e.g., FIG. 1A). These bone particles were obtained from the diaphyseal regions of porcine femora and tibae and were partially demineralized using the methodology described above. After the particles were formed and dehydrated, they were then weighed and added to the premixed cement powder in volume ratios of 10.0% and 20.0%. The dry components of cement powders and dry bone particles were then thoroughly mixed.

For purposes of comparison, calcium phosphate mixtures were also made using non-specially shaped cortical bone particles of similar size to those described above. Again, the non-specially shaped particles were produced by grinding 0.5 mm thick scrap bone to produce particles between 1.75 mm and 0.5 mm particle size dimensions. These particles were also partially demineralized as described above and dehydrated before being added to the calcium phosphate powder and thoroughly mixed to produce approximate volume ratios of 10% and 40%%, as it was found in the experiments described above that a higher percentage of non-specially shaped bone particles was required to be added to the cement to achieve a similar level of remodeling potential through interconnectedness as compared to the specially-shaped particles that were included at a lower percentage.

Figure 8:
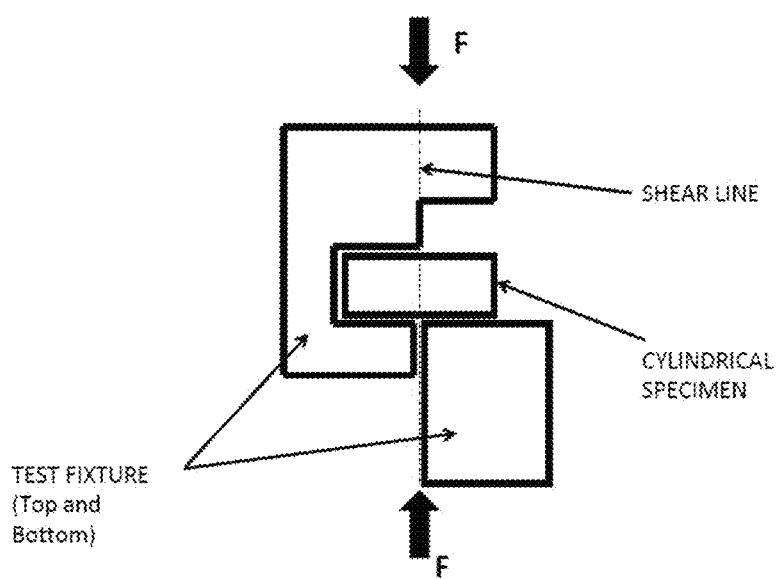
FIG. 8 is a schematic diagram of an experimental shear test fixture used to apply a force (F) along a shear line and assess the shear strength of a hardened bone graft composition (cylindrical specimen) made in accordance with the presently-disclosed subject matter.

Subsequent to the formation of the powders and the bone particles, test samples were then created by combining the dry bone and cement materials with an appropriate amount of distilled water (2.6:1 ratio of calcium phosphate powder to water by weight), mixing with a thin metal spatula, until a consistent wet paste was formed. Next, the materials were spread into tapered cylindrical (conical) molds that had been machined into an aluminum block. The molds were designed to create test samples 20 mm in length with an average diameter of 8 mm spread over a 1-degree taper along the length of the sample. Thus, the minimum diameter of the test sample was 7.83 mm, and the maximum diameter was 8.17 mm. The rationale for the taper was for ease of removal of the samples from the one-piece molds and for shear testing using a custom made shear test fixture that shared the same taper as the molds, as depicted in FIG. 8.

TABLE 5

Shear Strength (MPa) of Calcium Phosphate Based Composite Cements

|  | CaP 100% | Tr 10% | Tr 20% | Alt 10% | Alt 40% |
|---|---|---|---|---|---|
| Mean | 4.3 | 3.4 | 2.3 | 3.0 | 1.6 |
| Std. Dev. | 0.7 | 0.5 | 0.4 | 0.7 | 0.4 |
|  | p | <0.005 | <0.0001 | <0.001 | <0.00001 |

Figure 9:
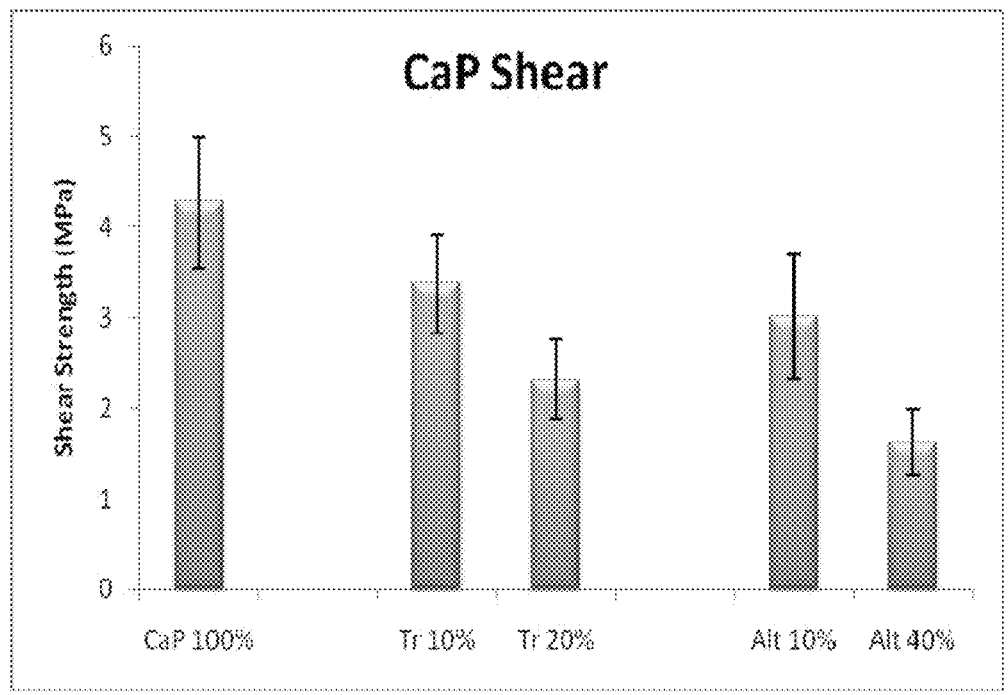
FIG. 9 is a graph showing the results of a shear test performed with a shear test fixture as shown in FIG. 8 to analyze the shear strength of: a pure calcium phosphate cement (CaP 100%) comprised of tetracalcium phosphate (TTCP), monocalcium phosphate (MCP), and calcium carbonate; a bone graft composition of the presently-disclosed subject matter that includes a calcium phosphate cement comprised of TTCP, MCP and calcium carbonate and that includes 10 percent or 20 percent by volume of processed bone particles having a shape as shown in FIG. 1A (Tr 10% and Tr 20%, respectively); and a bone graft composition that includes a calcium phosphate cement comprised of TTCP, MCP and calcium carbonate and that includes 10 percent or 40 percent by volume of non-specially shaped bone particles (Alt 10% and Alt 40%, respectively)

As shown in FIG. 9 and Table 5, upon analysis of the results from these experiments, it was observed that adding specially-shaped and partially demineralized bone particles (Tr) to a calcium phosphate cement at a 10% volume fraction improved the mechanical properties of the composition in the demanding loading mode of shear, while the addition of 20% specially-shaped bone particles and both 10% and 40% non-specially shaped bone particles (Alt) significantly weakened the calcium phosphate in shear. As such, these results thus indicated that an osteoconductive, remodelable, resorbable, and osteoinductive material can be added to a calcium phosphate cement and improve its mechanical shearing properties.

Example 9

Analysis of Bending Strength of Calcium Phosphate (Alpha-Tricalcium Phosphate/Hydroxyapatite)-based Bone Graft Composition To further assess the shear strength of calcium phosphate-based cements augmented with specially-shaped cortical bone particles, additional mechanical testing experiments using an alternative calcium phosphate cement with various amounts of partially-demineralized, shaped cortical bone particles were undertaken. Briefly, in these further experiments, a calcium phosphate cement comprising a commercial grade calcium phosphate cement, including alpha-tricalcium phosphate powder that, upon mixing with a setting solution forms precipitated hydroxyapatite, was used. When this powder mixture was mixed with water in a 2.6:1 powder-to-water ratio by weight, a paste formed that was capable of setting within fifteen minutes into a solid mass.

Similar to the methodology described above, cortical bone particles were then again created through a machining process that yielded specially shaped particles approximately 2.5 mm in length, 1.5 mm in width at each end, and 0.5 mm thickness on average with a 0.5 mm wide center portion (see, e.g., FIG. 1A). These bone particles were once again obtained from the diaphyseal regions of porcine femora and tibae and were partially demineralized subsequent to weighing and adding the bone particles to the premixed cement powder in volume ratios of 10.0% and 20%. The dry components of cement powders and dry bone particles were then thoroughly mixed.

Again, for purposes of comparison, calcium phosphate mixtures were also made using non-specially shaped cortical bone particles of similar size to those described above. The non-specially shaped particles were again produced using scrap bone and had particle size dimensions of between 1.75 mm and 0.5 mm. These particles were also partially demineralized as described above and dehydrated before being added to the calcium phosphate powder, and were thoroughly mixed to produce an approximate volume ratio 40%%, as it was found in the experiments described above that a higher percentage of non-specially shaped bone particles was required to be added to the cement to achieve a similar level of remodeling potential through interconnectedness as compared to the specially-shaped particles that were included at a lower percentage.

Subsequent to the formation of the powders and the bone particles, test samples were once again created by combining the dry bone and cement materials with an appropriate amount of distilled water (2.6:1 ratio of calcium phosphate powder to water by weight), mixing with a thin metal spatula, until a consistent wet paste was formed. Next, the materials were once again spread into tapered cylindrical (conical) molds that had been machined into an aluminum block. The molds were designed to create test samples 20 mm in length with an average diameter of 8 mm spread over a 1-degree taper along the length of the sample. Thus, the minimum diameter of the test sample was 7.83 mm, and the maximum diameter was 8.17 mm. The rationale for the taper was for ease of removal of the samples from the one-piece molds and for shear testing using a custom made shear test fixture, depicted in FIG. 8, that shared the same taper as the molds.

TABLE 6

Shear Strength (MPa) of Calcium Phosphate Based Composite Cements

|  | CaP 100% | Tr 10% | Tr 20% | Alt 40% |
|---|---|---|---|---|
| Mean | 2.8 | 3.2 | 1.5 | 1.2 |
| Std. Dev. | 0.4 | 0.7 | 0.3 | 0.4 |
|  | p | NS | <0.00001 | <0.00001 |

Figure 10:
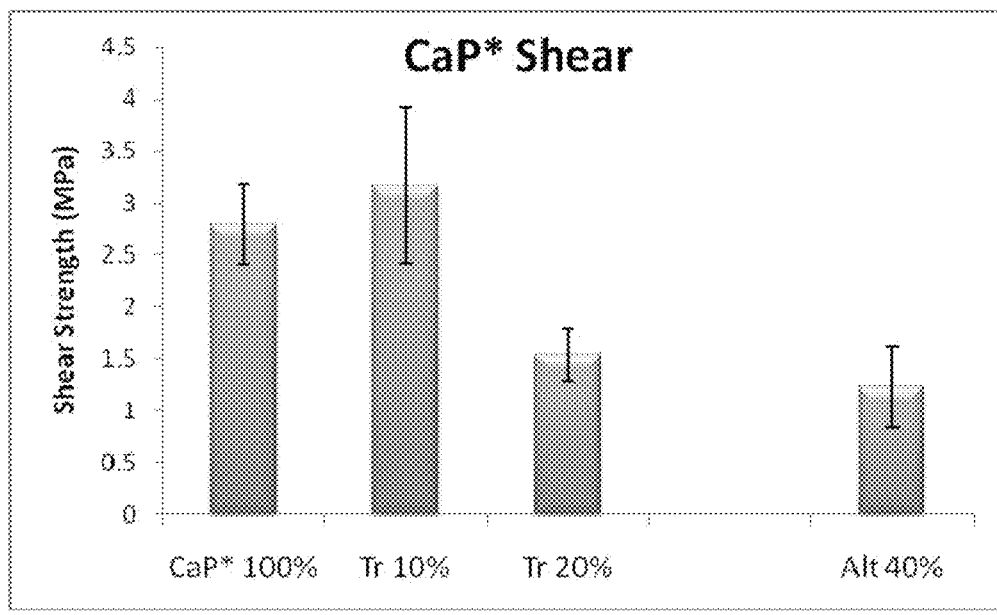
FIG. 10 is a graph showing the results of a shear test performed with a shear test fixture as shown in FIG. 8 to analyze the shear strength of: a pure, commercial-grade calcium phosphate cement (CaP* 100%) made from alpha-tricalcium phosphate powder; a bone graft composition of the presently-disclosed subject matter that includes a commercial-grade calcium phosphate cement made from alpha-tricalcium phosphate powder and that includes 10 percent or 20% by volume of processed bone particles having a shape as shown in FIG. 1A (Tr 10% or Tr 20%, respectively); and a bone graft composition that includes a commercial-grade calcium phosphate cement made from alpha-tricalcium phosphate powder and that includes 40 percent by volume of non-specially shaped bone particles (Alt 40%)

As shown in FIG. 10 and Table 6, upon analysis of the results from these experiments, it was observed that adding specially-shaped and partially demineralized bone particles (Tr) to a further calcium phosphate cement at a 10% volume fraction improved the mechanical properties of the composition in the demanding loading mode of shear, while the addition of 20% specially-shaped bone particles and 40% non-specially shaped bone particles (Alt) significantly weakened the calcium phosphate in shear. As such, these results thus also indicated that an osteoconductive, remodelable, resorbable, and osteoinductive material can be added to a calcium phosphate cement and improve its mechanical shearing properties.

Example 10

Analysis of Shear Strength of a Calcium Sulfate-based Bone Graft Composition To assess the shear strength of a non-calcium phosphate-based cement in conjunction with the presently-described, specially-shaped cortical bone particles, mechanical testing experiments using a calcium sulfate (CaS) cement with various amounts of partially-demineralized, shaped cortical bone particles were also undertaken to assess the mechanical behavior effects of adding various percentages of the specially processed cortical bone particles to that calcium-based cement. Briefly, in this further experiment, a commercial grade CaS cement was used and was mixed with water in a 2:1 powder-to-water ratio by weight, such that a paste was formed that was capable of setting within twenty minutes into a solid mass.

Similar to the methodology described above, cortical bone particles were then again created through a machining process that yielded specially-shaped particles approximately 2.5 mm in length, 1.5 mm in width at each end, and 0.5 mm thickness on average with a 0.5 mm wide center portion (see, e.g., FIG. 1A). These bone particles were also obtained from the diaphyseal regions of porcine femora and tibae and were partially demineralized subsequent to weighing and adding the bone particles to the premixed cement powder in a volume ratios of 10.0% and 20.0%. The dry components of cement powders and dry bone particles were then thoroughly mixed.

Subsequent to the formation of the powders and the bone particles, test samples were once again created by combining the dry bone and cement materials with an appropriate amount of distilled water (2:1 ratio of CaS powder-to-water by weight), and mixing with a thin metal spatula until a consistent wet paste was formed. Next, the materials were once again spread into tapered cylindrical (conical) molds that had been machined into an aluminum block. The molds were designed to create test samples 20 mm in length with an average diameter of 8 mm spread over a 1-degree taper along the length of the sample. Thus, the minimum diameter of the test sample was 7.83 mm, and the maximum diameter was 8.17 mm. The rationale for the taper was for ease of removal of the samples from the one-piece molds and for shear testing using a custom made shear test fixture, depicted in FIG. 8, that shared the same taper as the molds.

TABLE 7

Shear Strength (MPa) of Calcium Phosphate Based Composite Cements

|  | CaP 100% | Tr 10% | Tr 20% |
|---|---|---|---|
| Mean | 0.8 | 1.0 | 0.9 |
| Std. Dev. | 0.4 | 0.5 | 0.4 |

Figure 11:
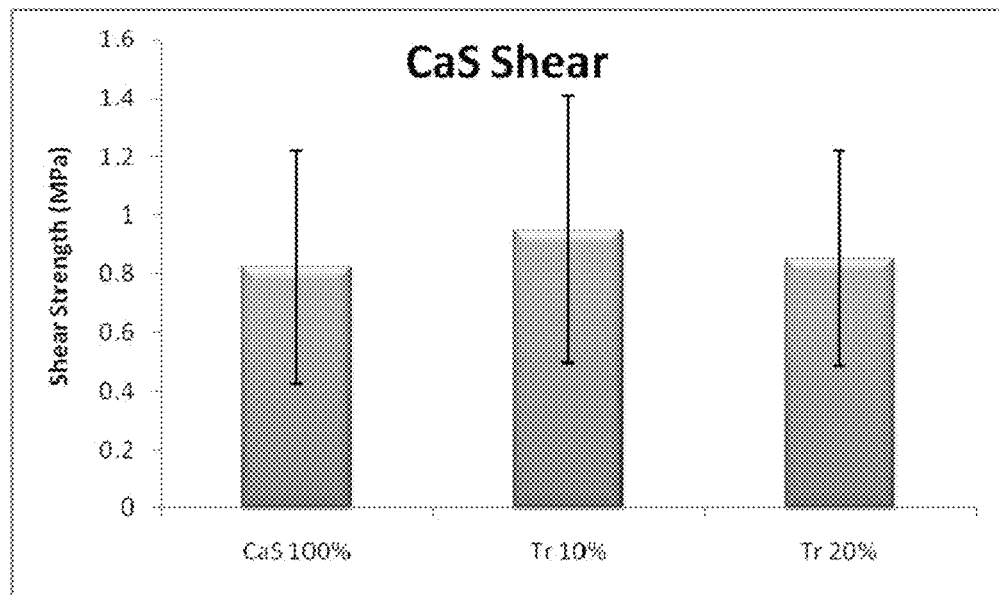
FIG. 11 is a graph showing the results of a shear test performed with shear test fixture as shown in FIG. 3 to analyze the shear strength of: a pure, commercial grade calcium sulfate cement (CaS 100%); and a bone graft composition of the presently-disclosed subject matter that includes a commercial-grade calcium sulfate cement and that includes 10 percent or 20 percent by volume of processed bone particles having a shape as shown in FIG. 1A (Tr 10% and TR 20%, respectively)

As shown in FIG. 11 and Table 7, upon analysis of the results from these experiments, it was observed that the addition of specially-shaped and partially demineralized bone particles (Tr) to a CaS cement did not significantly compromise its mechanical properties in the demanding loading mode of shear. In other words, the foregoing results further demonstrate that an osteoconductive, remodelable, resorbable, and osteoinductive material can be added to a CaS cement without negatively affecting its mechanical properties, provided the particles possess the shapes tested here.

Example 11

Diametral Tensile Strength of Calcium Sulfate-based Bone Graft Composition

To assess the diametral tensile strength of a calcium-sulfate cement incorporating the specially-shaped bone particles of the presently-disclosed subject matter, mechanical testing experiments using a calcium sulfate (CaS) cement that incorporated various amounts of partially demineralized shaped cortical bone particles were undertaken. In these experiments, and similar to the experiments described above, a commercial grade CaS cement was used that, when mixed with water in a 2:1 powder-to-water ratio by weight, was capable of forming a paste that set within twenty minutes into a solid mass. Also, in these experiments and again similar to the methodology described above, cortical bone particles were created through a machining process that yielded specially-shaped particles approximately 2.5 mm in length, 1.5 mm in width at each end, and 0.5 mm thickness on average with a 0.5 mm wide center portion (FIG. 1A). These bone particles were also obtained from the diaphyseal regions of porcine femora and tibae and were also partially demineralized using the methodology described above. After the particles were formed and dehydrated, they were then weighed and added to the premixed cement powder in volume ratios of 10.0% and 20.0%. The dry components of cement powders and dry bone particles were thoroughly mixed.

For comparison, alternative mixtures were made using non-specially shaped cortical bone particles of similar size to those described above. The non-specially shaped particles were again produced by grinding 0.5 mm thick scrap to produce particles between 1.75 mm and 0.5 mm particle size dimensions, and were also partially demineralized as described above and dehydrated before being added to the CaS powder and thoroughly mixed to produce approximate volume ratios of 10% and 40%, as it was found in the experiments described above that a higher percentage of non-specially shaped bone particles was required to be added to the cement to achieve a similar level of remodeling potential through interconnectedness as compared to the specially-shaped particles that were included at a lower percentage.

The test samples were then created by combining the dry materials with an appropriate amount of distilled water (2:1 ratio of CaS powder-to-water by weight), and mixing with a thin metal spatula until a consistent wet paste was formed. Next, the materials were spread into tapered cylindrical (i.e., conical) molds that had been machined into an aluminum block. The molds were designed to create test samples 20 mm in length with a diameter of 8 mm.

Figure 12:
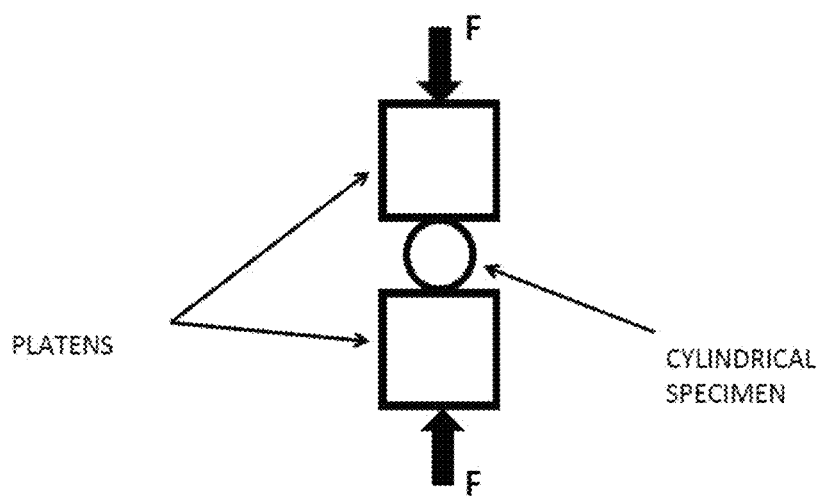
FIG. 12 is a schematic diagram of an experimental fixture used to apply a force (F) and assess the diametral tensile strength of a hardened bone graft composition (cylindrical specimen) made in accordance with the presently-disclosed subject matter.

The diametral tension test was performed using two polished parallel platens (see FIG. 12). The cylindrical specimen was placed horizontally such that a compressive load could be applied in a direction perpendicular to the longitudinal axis at a rate of 0.1 in/min (2.54 mm/min). The maximum force achieved prior to the first failure of the sample resulting in a 40% reduction in applied load or a significant change in specimen stiffness was then recorded, and the failure stress was calculated based on the applied load and the sample geometry using the formula $\sigma=2P/(\pi*D*L)$, where P is the load, D is the diameter, and L is the length of the specimen.

TABLE 8

Diametral Tensile Strength (MPa) of Calcium Sulfate Based Composite Cements.

|  | CaS 100% | Tr 10% | Tr 20% | Alt 10% | Alt 40% |
|---|---|---|---|---|---|
| Mean | 1.1 | 1.5 | 1.4 | 0.9 | 0.7 |
| Std. Dev. | 0.2 | 0.4 | 0.4 | 0.2 | 0.2 |

Figure 13:
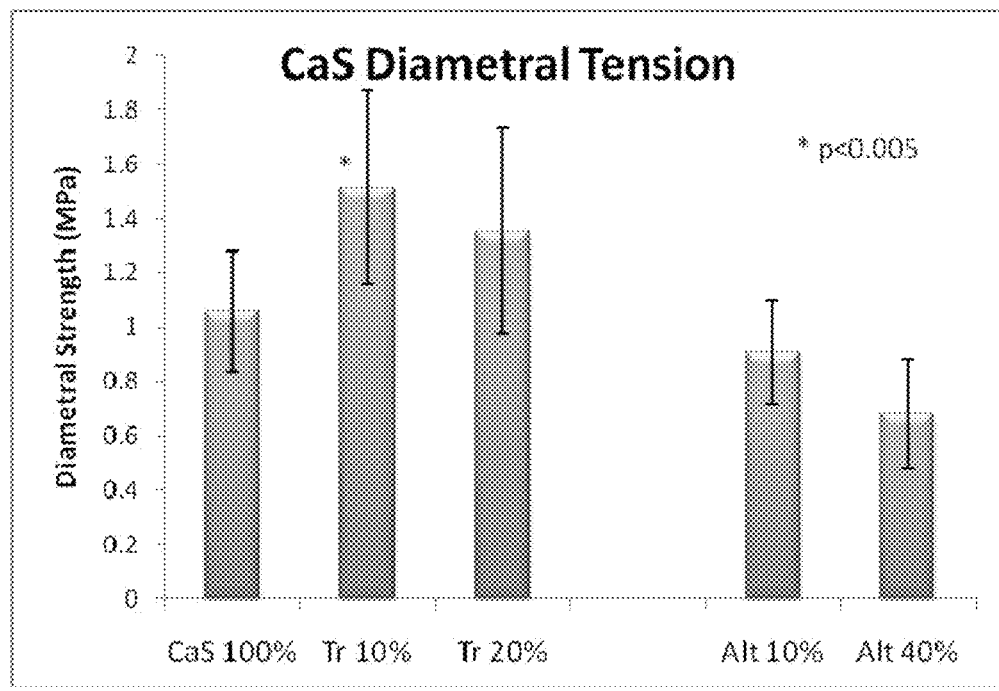
FIG. 13 is a graph showing the results of a diametral tensile test performed with a fixture as shown in FIG. 12 to analyze the diametral tensile strength of: a pure, commercial grade calcium sulfate cement (CaS 100%); a bone graft composition of the presently-disclosed subject matter that includes a commercial-grade calcium sulfate cement and that includes 10 percent or 20 percent by volume of processed bone particles having a shape as shown in FIG. 1A (Tr 10% and TR 20%, respectively); and a bone graft composition that includes a calcium sulfate cement and that includes 10 percent or 40 percent by volume of non-specially shaped bone particles (Alt 10% and Alt 40%, respectively)

Upon analysis of the results from the diametral tensile strength experiments, and as shown in FIG. 13 and Table 8, it was observed that adding specially-shaped and partially demineralized bone particles (Tr) to a CaS cement can significantly increase its mechanical strength in the demanding loading mode of diametral tension, while the addition of 10% and 40% non-specially shaped bone particles (Alt) significantly weakened the diametral tensile strength of the calcium phosphate. As such, these results also provide further support for the finding that an osteoconductive, remodelable, resorbable, and osteoinductive material can be added to a Ca-based cement and can be used improve its mechanical properties, provided the particles possess the unique shapes tested here.

Example 12

Bending Toughness (Energy-to-Failure) of Calcium Phosphate-Based Bone Graft Composition when Loaded Dynamically To assess the bending toughness of a calcium phosphate-based cement incorporating the specially-shaped bone particles of the presently-disclosed subject matter when such a composition is loaded dynamically, mechanical testing experiments using calcium phosphate cement with various amounts of partially-demineralized, specially-shaped cortical bone particles were undertaken. Briefly, a calcium phosphate cement consisting of tetracalcium phosphate (TTCP) powder, monocalcium phosphate (MCP) powder, calcium carbonate powder was used, and was mixed with water in a 2.6:1 powder-to-water ratio by weight, such that a paste was formed that set within fifteen minutes into a solid mass.

Similar to the methodology described above, cortical bone particles from the diaphyseal regions of porcine femora and tibae were again created through a machining process that yielded specially-shaped particles approximately 2.5 mm in length, 1.5 mm in width at each end, and 0.5 mm thickness on average with a 0.5 mm wide central region (FIG. 1A). These bone particles were then partially demineralized using the methodology described above and, after the particles were formed and dehydrated, were then weighed and added to the premixed cement powder in volume ratios of approximately 10.0% and 20.0%. The dry components of cement powders and dry bone particles were then thoroughly mixed.

Test samples were then created by combining the dry materials with an appropriate amount of distilled water (2.6:1 ratio of calcium phosphate powder to water by weight), mixing with a thin metal spatula, until a consistent wet paste was formed. Next, the materials were spread into cylindrical Teflon® (Du Pont De Nemours And Company Corporation, Wilmington, Del.) molds. The molds are designed to create test samples 20 mm in length with a diameter of 8 mm.

Similar to experiments described above, the dynamic bending test was performed using a three-point bending fixture with an 11 mm support span and a central radiused "blade" that applies a load to the top of the horizontally oriented specimen at a rate of 10 mm/s. The toughness of the samples was calculated as the energy-to-failure by measuring the under the load-displacement curve during the test to failure in bending.

TABLE 9

Bending Toughness (energy-to-failure: N-mm) of Calcium Phosphate Based Composite Cements.

|  | CaP 100% | Tr 10% |
| --- | --- | --- |
| Mean | 21.9 | 160.4 |
| Std. Dev. | 3.6 | 46.3 |
| P |  | <0.00001 |

Upon analysis of the results from the dynamic bending experiments, and as shown in Table 9, it was observed that the addition of specially-shaped and partially-demineralized bone particles to a calcium phosphate cement significantly improved its mechanical properties in the demanding loading mode of bending, indicating that an osteoconductive, remodelable, resorbable, and osteoinductive material can effectively be added to a calcium phosphate cement while significantly increasing its bending toughness, provided the particles possess the unique shapes tested here.

Example 13

Mechanical Testing of Calcium Phosphate Cement with Various Percentage Inclusion of Partially Demineralized Elongated Cortical Bone Particles Mechanical testing experiments using calcium phosphate cement with various amounts of partially demineralized elongated cortical bone particles were undertaken to determine the mechanical behavior effects of adding various percentages of specially processed cortical bone particles to an exemplar calcium phosphate cement. Briefly, a commercial grade calcium phosphate cement consisting of equimolar parts of tetracalcium phosphate (TTCP) and dicalcium phosphate anhydrous (DCPA) powders was used. When these powders were mixed with a solution of sodium phosphate, a paste formed that set within twenty minutes into a solid hydroxyapatite ceramic mass.

Similar to the methodology described above, cortical bone particles were created through a milling process that yielded elongated particles approximately 5 mm in length and 0.5 mm thickness on average. These bone particles were obtained from the mid-diaphyseal regions of porcine femora and tibae and were also partially demineralized using the methodology described above. After the particles were formed and dried, the particles were then weighed and added to the premixed cement powder in the following weight ratios: 0.0%, 1.25%, 2.5%, 3.75%, and 5.0 percent. The resulting cements were labeled X000, X125, X250, X375, and X500, respectively. Because the ceramic was denser than the partially demineralized bone particles, the volume percentages of bone in the cement were approximately 50% greater than the weight percentages. The dry components of cement powders and dry bone particles were thoroughly mixed.

Test samples were then created by mixing the dry materials with an appropriate amount of a sodium phosphate (NaP) solution, using a thin metal spatula, until a consistent wet paste was formed. Next, the materials were spread into tapered cylindrical (conical) molds that had been machined into an aluminum block. The molds were designed to create test samples 20 mm in length with an average diameter of 8 mm spread over a 1 degree taper along the length of the sample. Thus, the minimum diameter of the test sample was 7.83 mm and the maximum diameter was 8.17 mm. The rationale for the taper was for ease of removal of the samples from the one-piece molds and for the shear testing.

Shear testing was done using a custom-made shear test fixture (see FIG. 8). Three-point bending testing was done using the same sample type with the maximum bending stress placed at the central point (8 mm diameter) of the sample. In both cases, however, the tests were performed by advancing the fixture. Furthermore, and in addition to testing the strength of each sample (bending and shear) that was measured as a function of the sample geometry and the maximum load attained before failure, the work of failure (or toughness) of each sample was determined by calculating the area under the load displacement curve for each test.

Figure 14:
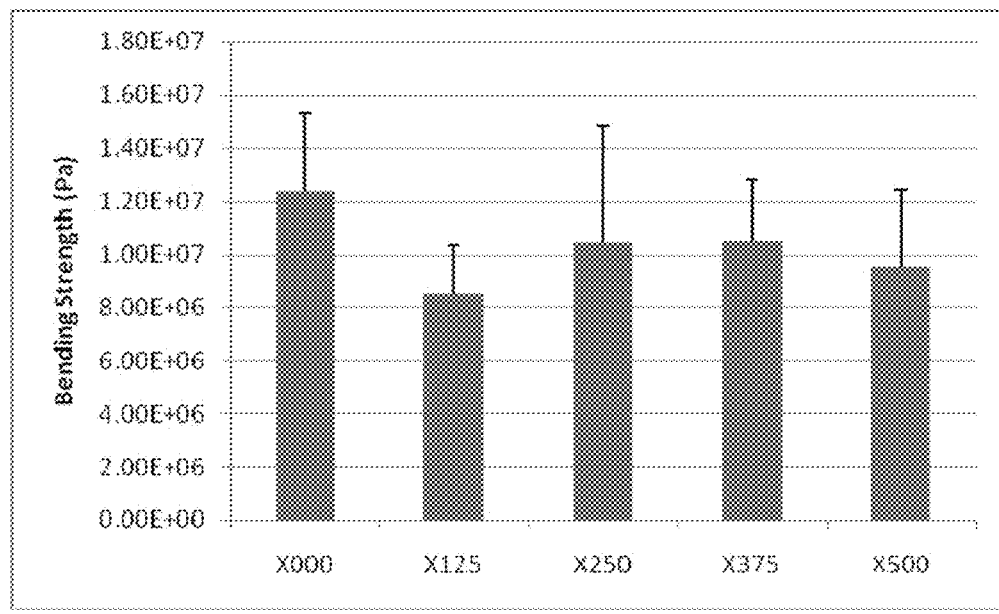
FIG. 14 is a graph showing the bending strength of bone graft compositions comprised of elongated cortical bone particles that were mixed with calcium phosphate cement, where the bone particles were added to the calcium phosphate cement powder in approximate volume ratios of 0.0% (X000), 1.25% (X125), 2.5% (X250), 3.75% (X375), and 5.0% (X500)

The bending test results for these samples are depicted in FIG. 14. The bending test results for a control calcium phosphate cement were similar to other published values for standard calcium phosphate cement (Xu et al., J Biomed Mater Res. 2001 Dec. 5; 57(3):457-66). The strength for the 0% samples was 12.4±2.9 MPa (mean±SD). None of the samples with processed bone added were significantly different from the control (p>0.05). The strongest of the composites was the 3.75% bone material which had a strength of 10.5±2.3 MPa. Table 10 below contains the maximum force data recorded for each test during the bending test, and it was the maximum force that was used to calculate the strength of each test sample

TABLE 10

3-Point Bending.

| Bone Source | XBC + 0.0% | XBC + 1.25% | XBC + 2.50% | XBC + 3.75% | XBC + 5.0% |
|---|---|---|---|---|---|
| 45.16 | 279.24 | 192.85 | 156.56 | 152.29 | 218.43 |
| 40.64 | 297.13 | 94.68 | 125.66 | 236.67 | 214.48 |
| 23 | 212.93 | 157.43 | 92.75 | 145.69 | 154.15 |
| 51.09 | 203.39 | 172 | 220.79 | 163.45 | 173.65 |
| 48.35 | 215.5 | 166.62 | 243.51 | 219.31 | 80.09 |
| 50.56 | 150.22 | 152.41 | 306.6 | 233.06 | 206.39 |

| | Bsource | X000 | X125 | X250 | X375 | X500 |
|---|---|---|---|---|---|---|
| Mean | 43.133 | 226.402 | 155.998 | 190.978 | 191.745 | 174.532 |
| SD | 10.596 | 53.718 | 33.172 | 80.146 | 42.340 | 52.675 |

Figure 15:
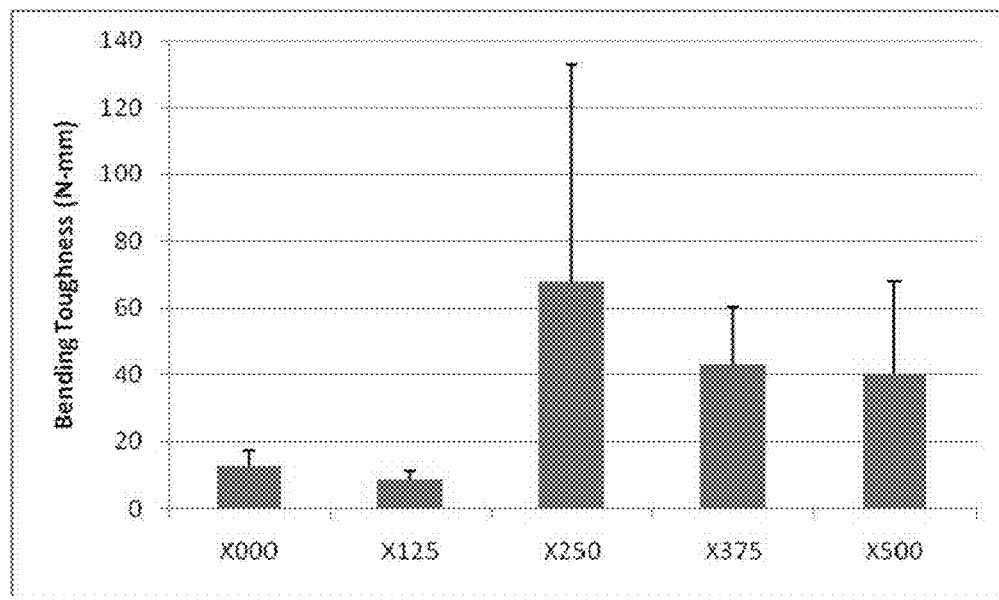
FIG. 15 is a graph showing the bending toughness of bone graft compositions comprised of elongated cortical bone particles that were mixed with calcium phosphate cement, where the bone particles were added to the calcium phosphate cement powder in approximate volume ratios of 0.0% (X000), 1.25% (X125), 2.5% (X250), 3.75% (X375), and 5.0% (X500)

The bending toughness test results are depicted in FIG. 15 and in Table 11 below. The bending toughness results showed greater toughness in the higher percentage composites compared to the control cement.

TABLE 11

3-Point Bending Toughness.

| Bone Source | XBC + 0.0% | XBC + 1.25% | XBC + 2.50% | XBC + 3.75% | XBC + 5.0% |
|---|---|---|---|---|---|
| 15.897 | 16.893 | 12.058 | 10.532 | 36.569 | 87.730 |
| 6.487 | 18.711 | 4.057 | 15.042 | 50.082 | 43.205 |
| 1.998 | 10.250 | 7.297 | 3.971 | 30.344 | 21.818 |
| 4.271 | 11.095 | 10.562 | 133.208 | 19.176 | 28.934 |
| 4.651 | 12.792 | 9.001 | 102.157 | 64.465 | 8.095 |
| 5.112 | 5.976 | 8.170 | 141.448 | 58.247 | 51.019 |

| | Bsource | X000 | X125 | X250 | X375 | X500 |
|---|---|---|---|---|---|---|
| Mean | 6.403 | 12.620 | 8.524 | 67.727 | 43.147 | 40.134 |
| SD | 4.875 | 4.636 | 2.773 | 64.838 | 17.392 | 27.859 |

Figure 16:
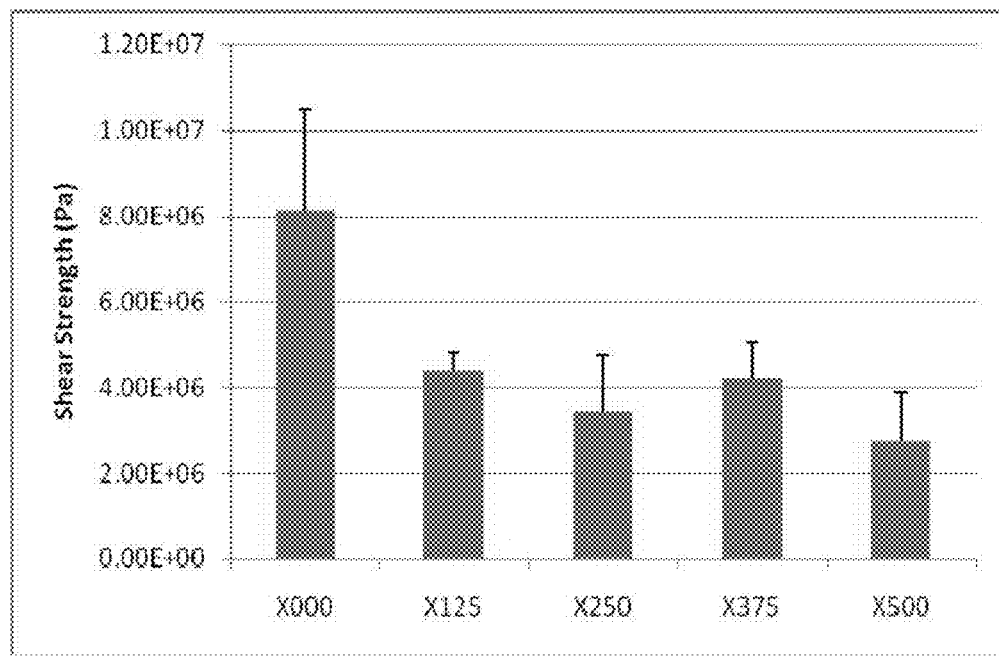
FIG. 16 is a graph showing the shear strength of bone graft compositions comprised of elongated cortical bone particles that were mixed with calcium phosphate cement, where the bone particles were added to the calcium phosphate cement powder in approximate volume ratios of 0.0% (X000), 1.25% (X125), 2.5% (X250), 3.75% (X375), and 5.0% (X500)

The shear strength test results are depicted in FIG. 16 and in Table 12 below. Table 3 contains the maximum force data recorded for each test during the shear test. It was that maximum force that was divided by the sample cross-sectional area and used to calculate the shear strength of each test sample. The shear strength of the control cement was significantly greater than the composited cements at all percentages, but each of these was reasonably strong in shear and none were significantly different from each other.

TABLE 12

Shear Strength.

| Bone Source | XBC + 0.0% | XBC + 1.25% | XBC + 2.50% | XBC + 3.75% | XBC + 5.0% |
|---|---|---|---|---|---|
| 74.1 | 416.9 | 228.1 | 89.9 | 202.1 | 144.9 |
| 49.7 | 499.1 | 177.7 | 210.7 | 284.2 | 132 |
| 44.7 | 473.2 | 236.5 | 131.1 | 165.2 | 220.5 |
| 32.1 | 435.3 | 228.2 | 277 | 224.7 | 87.5 |

TABLE 12-continued

Shear Strength.

| 35.2 | 455.8 | 231.1 | 153 | 213.5 | 60.8 |
|---|---|---|---|---|---|
| 134.9 | 173.2 | 222.8 | 179.5 | 182.3 | 179.4 |
| | 329.8 | | | | |

| | Bsource | X000 | X125 | X250 | X375 | X500 |
|---|---|---|---|---|---|---|
| Mean | 61.783 | 408.917 | 220.733 | 173.533 | 212 | 137.516 |
| SD | 38.790 | 118.984 | 21.551 | 65.328 | 41.344 | 58.502 |

Figure 17:
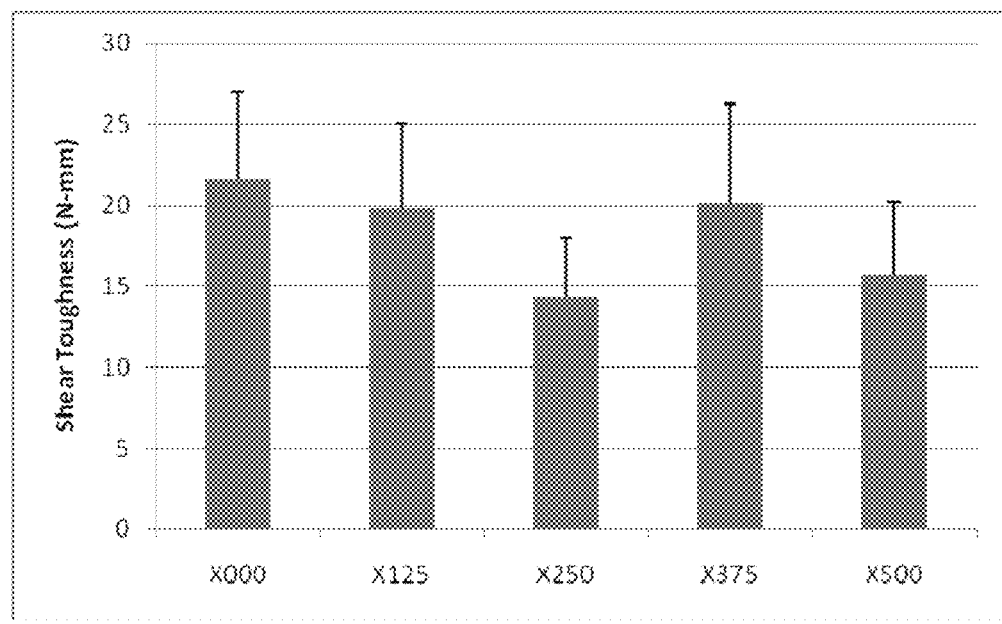
FIG. 17 is a graph showing the shear toughness of bone graft compositions comprised of elongated cortical bone particles that were mixed with calcium phosphate cement, where the bone particles were added to the calcium phosphate cement powder in approximate volume ratios of 0.0% (X000), 1.25% (X125), 2.5% (X250), 3.75% (X375), and 5.0% (X500)

The shear toughness test results are depicted in FIG. 17 and in Table 13 below. The shear toughness showed no significant difference between any of the sample groups.

TABLE 13

Shear Toughness.

| Bone Source | XBC + 0.0% | XBC + 1.25% | XBC + 2.50% | XBC + 3.75% | XBC + 5.0% |
|---|---|---|---|---|---|
| 7.2 | 17.4 | 20.3 | 9 | 31.2 | 15.9 |
| 7.1 | 25 | 27.8 | 15.7 | 16.4 | 13.8 |
| 3.5 | 31 | 12.7 | 14 | 16.4 | 19.5 |
| 3.2 | 19.7 | 15.6 | 20.1 | 23 | 13.2 |
| 3.8 | 18.6 | 20.7 | 13.6 | 19 | 9.7 |
| 12.5 | 18.4 | 21.7 | 14 | 14.7 | 22.2 |
| | 24.9 | | | | |

| | Bsource | X000 | X125 | X250 | X375 | X500 |
|---|---|---|---|---|---|---|
| Mean | 6.217 | 21.683 | 19.8 | 14.4 | 20.116 | 15.717 |
| SD | 3.565 | 5.298 | 5.229 | 3.586 | 6.154 | 4.530 |

The foregoing results indicate that adding elongated and partially demineralized bone particles to a calcium phosphate cement did not significantly compromise its mechanical properties in the demanding loading modes of shear and bending. In other words, the foregoing results demonstrate that an osteoconductive, resorbable, and osteoinductive material can be added to a calcium phosphate cement without negatively affecting its mechanical properties. In this regard, and without wishing to be bound by any particular theory, it is thought that the results described above further provide support for the proposition that the biologic behavior (incorporation, resorption, new bone formation) of bone cement compositions can be improved by the presence of the bone materials, without sacrificing the mechanical properties of the cement.

Example 14

Analysis of Simple Included Shapes with Two-Dimensional (2D) Connectivity

To further analyze the benefits that may be derived from producing specially-shaped bone particle and including those particles within cement-based bone graft composition to increase the incorporation, resorption, and remodeling and new bone formation within a resulting combined hardened material, an analysis was conducted to examine the maximization of the interconnectedness of the included particles, pores, or channels in conjunction with the minimization of the total volume of included particles, pores, or channels. The efficiency with which a particular shape can achieve complete connectivity is important to the efficacy of that shape compared to other shapes. In other words, when comparing different shapes of particles for inclusion in the bone graft compositions of the presently-disclosed subject matter, the shape that is most connected with the least volume of particle material can, in some instances, be considered most advantageous. Percolation theory indicates that for a regularly spaced matrix of potential voids, the probability that a given void exists ranges from 0 to 1 (no voids present to all voids present). Furthermore, there will be an important threshold probability at which it is possible or probable that a continuous pathway between voids exists that connects the outer boundary of the structure to the center of the structure. The level of the threshold probability depends on the shape of the voids (or in this case, the shape of the included particles) and the shape of the overall structure. See, e.g., Genin D. Percolation: Theory and Applications. NIST. 2007, which is incorporated herein by reference in its entirety.

To conduct the 2D analysis of the shapes of the bone particles, the overall structure was first represented by a regularly shaped mass of hardened synthetic bone substitute cement of similar dimensions to a filled defect (2.5 cm×2.5 cm). The cement material was then infused with specially-shaped bone particles that accelerate the incorporation and remodeling of the synthetic material. Three different shapes were considered. First, circles (spheres in 3D) were used to represent the most general shape indicative of simple grinding of bone in a mill. Second, rectangles were used to represent elongated particles produced through a simple machining process. Third, bone shapes in the form of a dumbbell having enlarged ends (see, e.g., FIG. 1A) were used as those shapes have been shown to have strength benefits, and this analysis was also, at least in part, designed to demonstrate any biologic benefits of those shapes due to connectivity.

The analysis then used a 10×10 grid space filled with 100 rectangular spaces. In turn, each location could be occupied by a particular shape (First circles, etc.). As the probability of a void presence increased, the number of shapes present then approached 100. A random number generator was used to determine the next location for placement of a shape. Each shape analysis was repeated ten times, and the probability value at which edge to center connectivity was achieved was recorded. The rectangles and specially-shaped bone particles were able to "connect" (i.e., contact one another) on sides or corners, but the circles could only "connect" on sides (FIG. 18). The grid was subsequently randomly filled ten times with corner connectivity, and ten times with only side connectivity allowed. The resulting threshold probabilities were 26.3±7.0% and 46.6±4.6% for corner connectivity (Rectangles and Dumbbells) and side connectivity (Circles), respectively.

TABLE 14

Grid experiment representing a case of side only connectivity that achieved edge-to-center connectivity at a void probability of 49%. The side-to-side connected pathway reaches one of four center grids (#46) and connects to outer edge grids (#s 8, 9, 30, 40). The various grid positions from 1 to 100 were highlighted randomly by sequential random number generation.

| 1 | 2 | 3 | 4 | 5 | 6 | 7 | 8 | 9 | 10 |
|---|---|---|---|---|---|---|---|---|---|
| 11 | 12 | 13 | 14 | 15 | 16 | 17 | 18 | 19 | 20 |
| 21 | 22 | 23 | 24 | 25 | 26 | 27 | 28 | 29 | 30 |
| 31 | 32 | 33 | 34 | 35 | 36 | 37 | 38 | 39 | 40 |
| 41 | 42 | 43 | 44 | 45 | 46 | 47 | 48 | 49 | 50 |
| 51 | 52 | 53 | 54 | 55 | 56 | 57 | 58 | 59 | 60 |
| 61 | 62 | 63 | 64 | 65 | 66 | 67 | 68 | 69 | 70 |
| 71 | 72 | 73 | 74 | 75 | 76 | 77 | 78 | 79 | 80 |
| 81 | 82 | 83 | 84 | 85 | 86 | 87 | 88 | 89 | 90 |
| 91 | 92 | 93 | 94 | 95 | 96 | 97 | 98 | 99 | 100 |

TABLE 15

Grid experiment representing a case of side and/or corner connectivity that achieved edge-to-center connectivity at a void probability of 29%. The connected pathway reaches one of four center grids (#55) and connects to outer edge grid (#93). The various grid positions from 1 to 100 were highlighted randomly by sequential random number generation.

| 1 | 2 | 3 | 4 | 5 | 6 | 7 | 8 | 9 | 10 |
|---|---|---|---|---|---|---|---|---|---|
| 11 | 12 | 13 | 14 | 15 | 16 | 17 | 18 | 19 | 20 |
| 21 | 22 | 23 | 24 | 25 | 26 | 27 | 28 | 29 | 30 |
| 31 | 32 | 33 | 34 | 35 | 36 | 37 | 38 | 39 | 40 |
| 41 | 42 | 43 | 44 | 45 | 46 | 47 | 48 | 49 | 50 |
| 51 | 52 | 53 | 54 | 55 | 56 | 57 | 58 | 59 | 60 |
| 61 | 62 | 63 | 64 | 65 | 66 | 67 | 68 | 69 | 70 |
| 71 | 72 | 73 | 74 | 75 | 76 | 77 | 78 | 79 | 80 |
| 81 | 82 | 83 | 84 | 85 | 86 | 87 | 88 | 89 | 90 |
| 91 | 92 | 93 | 94 | 95 | 96 | 97 | 98 | 99 | 100 |

Upon examination of the results from this analysis (see Table 16), it was observed that the volume fraction (area fraction in 2D) of each grid space occupied by the three shapes are Rectangle: 100%, Dumbbell: 66.7%, Circle: 78.5%. Thus, the amounts of included bone material (volume fraction) of each shape required to achieve threshold connectivity was further calculated to 26.3% for Rectangle shapes, 26.3×0.667=17.5% for Dumbbells, and 46.6×0.785=36.6% for Circles. More particularly, it was found that, compared to circles, Dumbbell shapes only require approximately half the material to achieve comparable connectivity, which is in addition to the strength benefits outline above.

TABLE 16

Result of Various Trials of 2D Connectivity Analysis

| Trial | Square | Circle |
|---|---|---|
| 1 | 23 | 49 |
| 2 | 22 | 43 |
| 3 | 27 | 46 |
| 4 | 27 | 49 |
| 5 | 41 | 51 |
| 6 | 34 | 37 |
| 7 | 17 | 42 |
| 8 | 29 | 50 |
| 9 | 22 | 48 |
| 10 | 21 | 51 |
| Mean | 26.3 | 46.6 |
| SD | 7.04036 | 4.599517 |

Example 15

Analysis of Simple Included Shapes with Three-Dimensional (3D) Connectivity

To further assess the connectivity of various shapes, the above-described analysis was repeated as a three-dimensional analysis by comparing spheres and dumbbell shapes in a three-dimensional grid pattern similar to that described in the previous example with the following exception: the pattern contained 1000 cube-shaped spaces that could be occupied by spheres or by cubes or by dumbbells. The spheres could "connect" only on faces while the cubes and dumbbell shapes could connect on faces, edges, and corners. In this regard, the potential connectivity of a given space occupied by a cube or a dumbbell shape with its 26 neighbors is complete with 6 faces, 12 edges, and 8 corners connected. With a sphere, there were only 6 potential connections (i.e., six points of contact).

TABLE 17

Results of Various Trials of 3D Connectivity Analysis.

| Trial | Cube | Sphere |
|---|---|---|
| 1 | 57 | 305 |
| 2 | 63 | 297 |
| 3 | 53 | 383 |
| 4 | 123 | 344 |
| 5 | 70 | 241 |
| 6 | 133 | 257 |
| 7 | 87 | 271 |
| 8 | 155 | 198 |
| 9 | 119 | 338 |
| 10 | 76 | 253 |
| Mean | 93.6 | 288.7 |
| SD | 36.0037 | 55.58787 |

Upon examination of the results from this analysis, it was found that the volume fraction of each grid space occupied by the three shapes are Cube: 100%, Dumbbell: 55.5%, Sphere: 52.3%, and thus, the amounts of included bone material (volume fraction) of each shape required to achieve threshold connectivity are 9.4% for Cube shapes, 9.36× 0.555=5.2% for Dumbbells, and 28.9×0.523=15.1% for Spheres. More particularly, it was found that, compared to spheres, dumbbell shapes only require one third the material to achieve comparable connectivity, which is in addition to the strength benefits outline above.

Example 16

Finite Element Modeling of Dumbbell-Shaped Bone Particles in Calcium Phosphate Cement To determine the mechanical behavior effects of adding specially-shaped, processed cortical bone particles to an exemplar calcium phosphate cement loaded in uniaxial tension, a finite element modeling system was used to model the mechanical properties of dumbbell-shaped particles as compared to more common shapes, such as simple cylinders. Without wishing to be bound by any particular theory, it was thought that if the interconnecting bone particles demonstrated a mechanical benefit compared to more common shapes, such as cylinders or spheres, then the unique shapes would be capable of exhibiting a synergistic effect that could be achieved in terms of both mechanics and biology.

Briefly, to examine the potential mechanical benefits, finite element analyses were performed using an academic research version of a commercially available software package (Ansys Release 12.0.1) running on a standard PC. The first analysis was set up as a two-dimensional plane strain simulation using 8 node quadrilateral elements. The test plane was a rectangular region 3.5 mm wide and 4 mm tall. The boundary conditions were such that the left boundary was fixed in the x-direction (horizontal). The lower left corner was pinned to not move in the y-direction (vertical). A uniform x-displacement of 0.0005 mm was applied to the right boundary.

Five models (FIG. 19) were created and executed, with the output being the Von Mises stress distribution over the test plane. Model 1 was entirely calcium phosphate cement, Models 2 and 3 contained three rectangular bone particles, and Models 4 and 5 contained three dumbbell-shaped bone particles. In models 3 and 5, the bone pieces had a uniform 0.1 mm thick collagen layer around their periphery. The dumbbell particles that were modeled in these analyses were 2.5 mm long and 1.5 mm wide by 0.5 mm thick. Further, in the analyses, the models were 4 mm in height and 3 mm in width.

The calcium phosphate cement was modeled as having the following mechanical properties: an elastic modulus of 40 GPa; a poisson ratio of 0.33; a yield strength of 5 MPa; and a plastic modulus of 5% of the elastic modulus.

The cortical bone was modeled as having the following mechanical properties: an elastic modulus of 15 GPa; a poisson ratio of 0.3; a yield strength of 150 MPa; and a plastic modulus of 5% of the elastic modulus.

The collagen layer (i.e., the demineralized surface) of the cortical bone was modeled as having the following mechanical properties: an elastic modulus of 150 MPa and a poisson ratio of 0.45.

Figure 20:
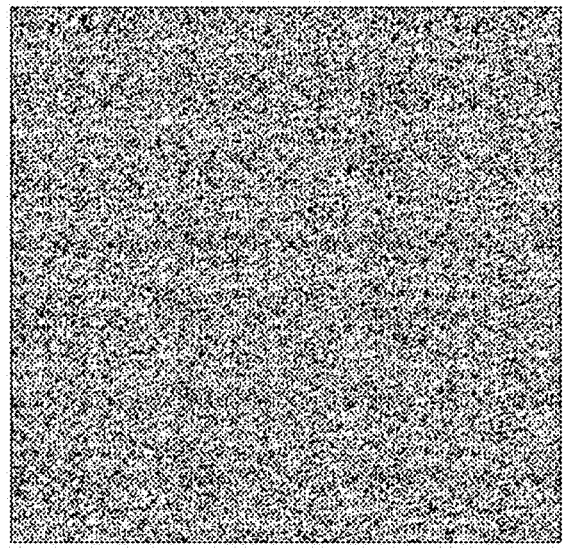
FIG. 20 is an image showing the results of finite element analysis of a model containing calcium phosphate cement only (Model 1), where the darker areas represent regions of higher stress.
Figure 20:
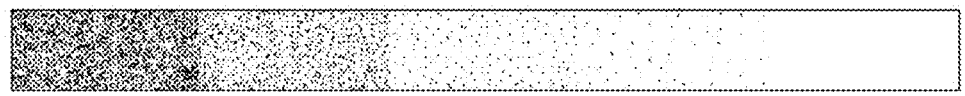
Figure 21:
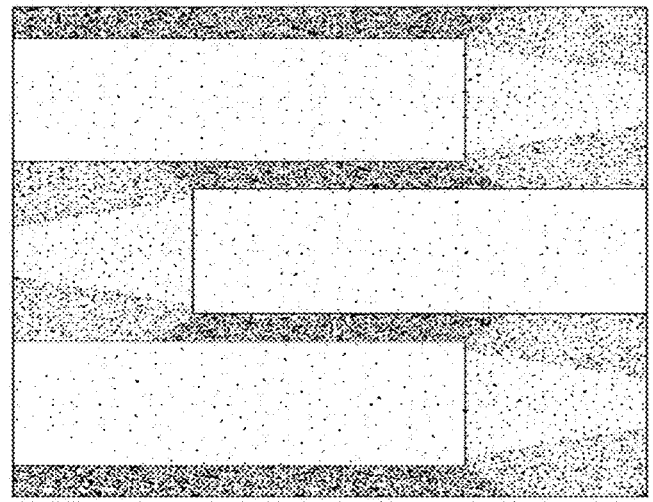
FIG. 21 is an image showing the results of finite element analysis of a model containing cylindrical cortical bone particles in calcium phosphate cement (Model 2), where the darker areas represent regions of higher stress.
Figure 21:
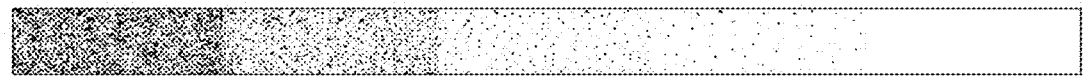
Figure 22:
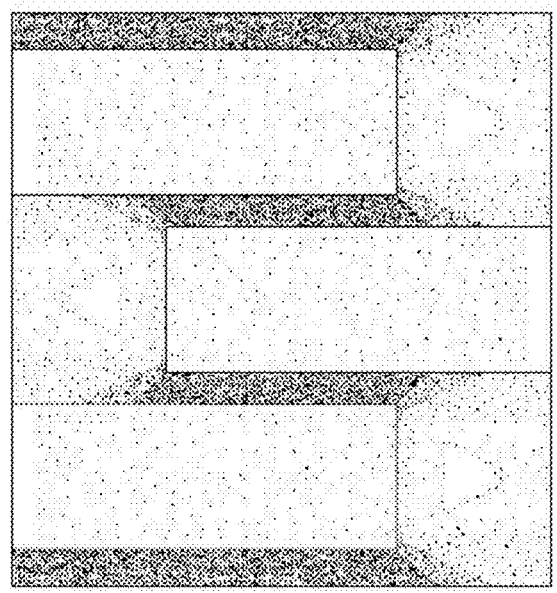
FIG. 22 is an image showing the results of finite element analysis of a model containing demineralized, cylindrical cortical bone particles in calcium phosphate cement (Model 3), where the darker areas represent regions of higher stress.
Figure 22:
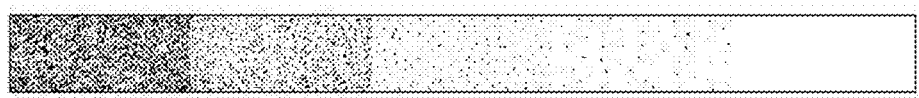
Figure 23:
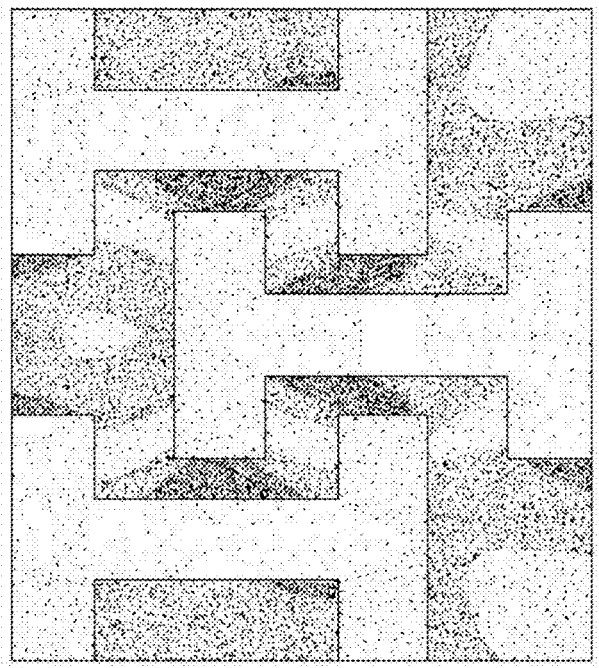
FIG. 23 is an image showing the results of finite element analysis of a model containing dumbbell-shaped cortical bone particles in calcium phosphate cement (Model 4), where the darker areas represent regions of higher stress.
Figure 23:
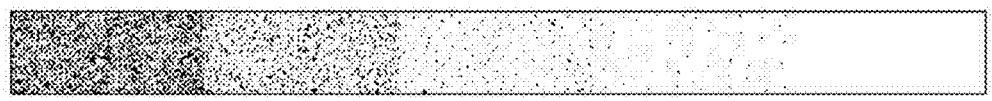
Figure 24:
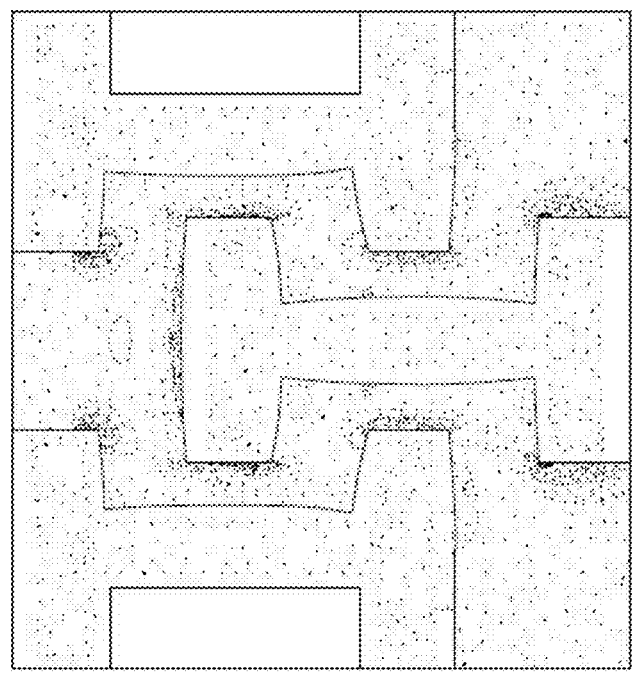
FIG. 24 is an image showing the results of finite element analysis of a model containing demineralized, dumbbell-shaped cortical bone particles in calcium phosphate cement (Model 5), where the darker areas represent regions of higher stress.
Figure 24:
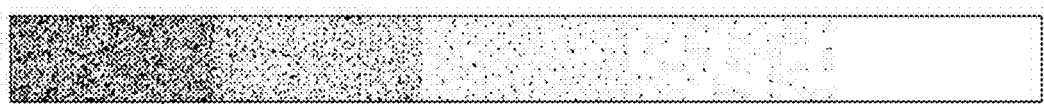

Upon reviewing the results from the finite elements modeling, it was observed that the model made up of only calcium phosphate cement (Model 1) showed a uniform stress distribution of over 5 MPa indicating complete failure of the cement substance at this level of strain (FIG. 20). In Model 2, the inclusion of bone cylinders was somewhat protective of the weaker, more brittle calcium phosphate cement (FIG. 21). There was, however, a wide path from the top to bottom of the sample that indicated cement failure and, as such, it was predicted that that sample would likely have failed completely. In Model 3, the 0.1 mm thick demineralized layer was of little benefit as the regions of high calcium phosphate cement stress were similar to Model 2 (FIG. 22). Model 4 showed a distinct protective effect, with the overlapping dumbbell-shaped particles allowing only isolated regions of high calcium phosphate cement stress (FIG. 23). Finally, Model 5 showed an even further protective effect when the overlapping dumbbell-shaped particles with a uniform 0.1 mm thick demineralized layer (FIG. 24) were included, as there were only a limited number of small regions of calcium phosphate cement stress in excess of its strength.

Figure 25:
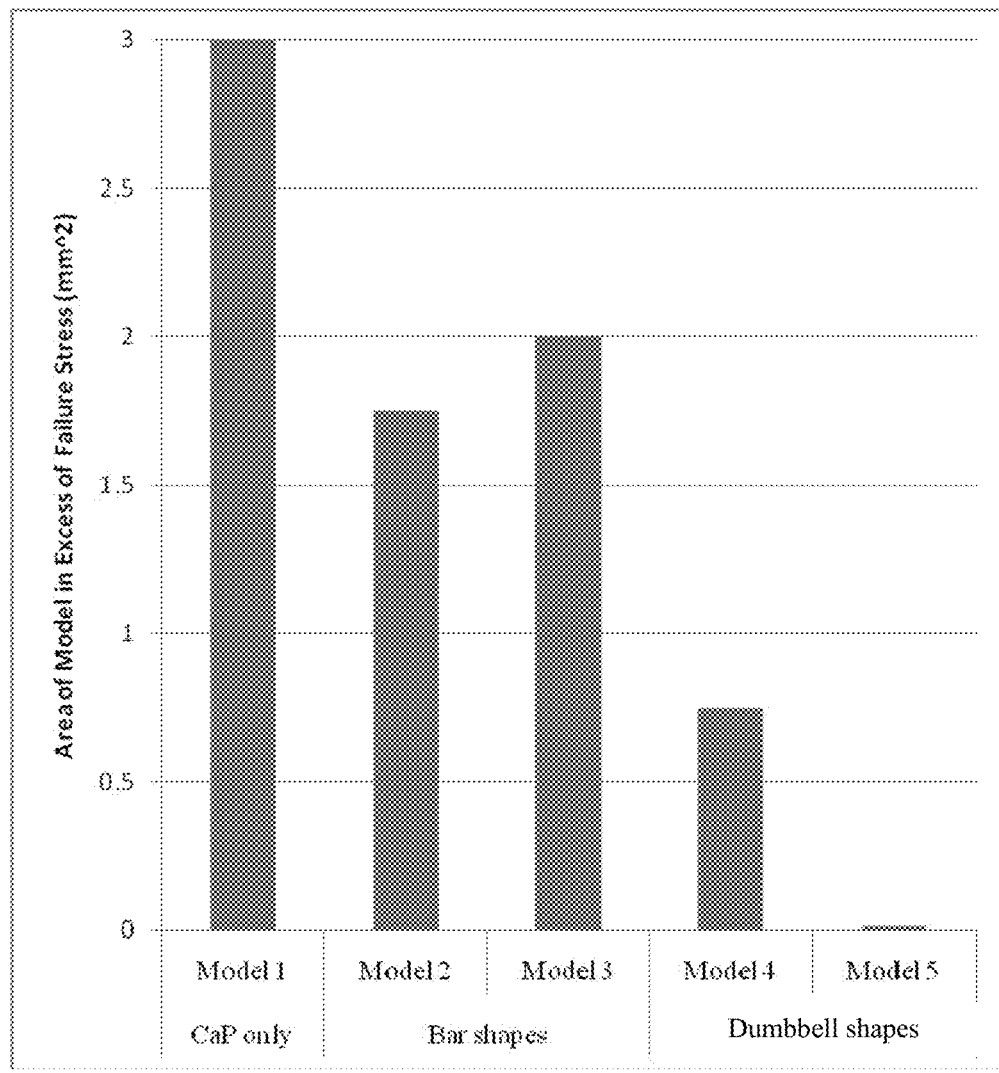
FIG. 25 is a graph showing the amount of the area of calcium phosphate cement that was stressed in excess of its strength (>5 MPa) in the various models illustrated in FIG. 14.

In further analyzing the results, it was observed that if the results were quantified by calculating the amount of area of calcium phosphate cement that was stressed in excess of its strength (>5 MPa), then the protective effect of the included bone particles could clearly be seen (FIG. 25). Furthermore, in addition to the obvious mechanical benefits of the dumbbell shapes, there was less total bone material in Models 4 and 5 (6.75 mm$^2$) compared to Models 2 and 3 (7.5 mm$^2$) and there was more total length of demineralized (collagen) layer (28.8 mm v. 19.8 mm). Without wishing to be bound by any particular theory, it was thus believed that the dumbbell shapes would also be expected to possess better biological properties because of the greater amount of osteoconductive surface that is exposed.

The foregoing results from the finite element modeling represented a mechanical benefit from adding the dumbbell-shaped bone particles to the calcium phosphate cement. The less stiff but stronger dumbbell-shaped bone particles protected the cement from reaching maximum stress. The branching parts of the dumbbell-shaped bone particles allowed better interdigitation with the cement which aided in the mechanical benefit, especially compared to the straight bars of bone used in models 2 and 3. Unexpectedly, adding the demineralized (collagen) layer to the bone pieces improved the mechanical benefit of adding the dumbbell-shaped bone particles and that unique combination created a composite structure that could undergo greater strain while minimizing the amount of its component materials reaching critical stress.

Example 17

Bone Volume Handling Test

The specially-shaped bone particles of the presently-disclosed subject matter can be incorporated into any bone void filler (BVF), such as a calcium-based cement, and it has been observed that there is an optimum percent volume of specially-shaped bone particles that should be incorporated in a hardened BVF to achieve a maximum flexural, tensile or compressive strength. Nevertheless, it was further recognized that there were other applications in which mechanical strength was of little concern, where the needs of a specific biological response and/or remodeling of a bone defect or void was of greater importance than any mechanical strength of the BVF. For example, some applications may require a greater quantity of specially-shaped bone particles, with a smaller percentage of the bone graft compositions volume being taken up by calcium phosphate cement material such that the bone graft compositions would achieve a faster incorporation and remodeling of a defect space. In this regard, experiments were undertaken to determine how high of a percentage of the BVF volume could be taken up by the specially-shaped bone particles before the bone graft composition's handling characteristics would prevent the material from setting into a solid mass.

Briefly, in these experiments, a calcium phosphate cement consisting of tetracalcium phosphate (TTCP) powder, monocalcium phosphate (MCP) powder, and calcium carbonate powder was used. When these powders were mixed with water in a 2.6:1 powder-to-water ratio by weight, a paste formed that set within fifteen minutes into a solid mass. Also, in these experiments and similar to the methodology described above, cortical bone particles were created through a machining process that yielded specially-shaped particles approximately 2.5 mm in length, 1.5 mm in width at each end, and 0.5 mm thickness on average with a 0.5 mm wide center portion (see FIG. 1A). These bone particles were obtained from the diaphyseal regions of porcine femora and tibae and were partially demineralized using the methodology described above.

After the particles were formed and dehydrated, they were then weighed and added to the premixed cement powder in an approximate 50% volume ratio. The dry components of cement powders and dry bone particles were thoroughly mixed, with the liquid being added to the dry components and mixed for 40 seconds to create a homogenous paste. The wetted and mixed material was very granular and would hold together if compressed. The material was then loaded into two Teflon® (Du Pont de Nemours and Company Corporation, Wilmington, Del.) cylindrical molds. The molds were designed to create test samples 20 mm in length with a diameter of 8 mm. A 7 mm rod was used to compress the material together and into the void space of the mold. At 20 min the cylindrical specimens were removed from the mold. One specimen was immediately placed in PBS and the other left in open air to complete setting. At 35 min, the sample in PBS had broken apart slightly but was hard and set. The sample left to air dry was in two pieces and also set.

The results from these experiments indicated that adding these specially-shaped and partially demineralized bone particles to a calcium phosphate cement at a concentration of 50% bone particles by volume allows the material to be handled and placed into a defect, even though the material is more wet granules than paste. In other words, the foregoing results demonstrate that an osteoconductive, remodelable, resorbable, and osteoinductive material can be added to a calcium phosphate cement in concentrations on the order of 50% specially-shaped, processed bone particle and still maintain the ability of the bone graft composition to set into a hardened mass.

Example 18

Injectability of Bone Graft Compositions

To assess the handling characteristics of a bone graft composition of the presently-disclosed subject matter, a calcium phosphate cement with demineralized, specially-shaped cortical bone particles was investigated to determine if the handling characteristics of the wetted bone graft composition would lend itself to being injected into a defect sight. Briefly, a calcium phosphate cement consisting of tetracalcium phosphate (TTCP) powder, monocalcium phosphate (MCP) powder, calcium carbonate powder was used. When these powders were mixed with water in a 2.5:1 powder-to-water ratio by weight, a paste formed that set within fifteen minutes into a solid mass.

Similar to the methodology described above, cortical bone particles were then created through a machining process that yielded specially-shaped particles approximately 2.5 mm in length, 1.5 mm in width at each end, and 0.5 mm thickness on average with a 0.5 mm wide center portion (see FIG. 1A). These bone particles were obtained from the diaphyseal regions of porcine femora and tibae and were partially demineralized using the methodology described above. After the particles were formed and dehydrated, the particles were then weighed and added to the premixed cement powder in an approximate 10% volume ratio. The dry components of cement powders and dry bone particles were thoroughly mixed, with the liquid being added to the dry components and mixed for 30 seconds to create a homogenous paste. This wetted material was then loaded into a syringe-style delivery device and injected through a 6 gauge cannula (approx. 4.6 mm ID). Approximately 1 cc was injected into a small container and covered with Phosphate Buffered Saline (PBS) after 20 min had elapsed. Another volume of approximately 1 cc was left in open air and allowed to set on the bench top. Both volumes set within 15 min. The portion that was covered in PBS and left overnight did not show any cloudiness of the solution or signs that the cement material had not set or dissolved to any degree.

The results from these experiments thus indicated that adding the specially-shaped and partially demineralized bone particles to a calcium phosphate cement did not reduce the ability of the bone graft composition to be injected. In other words, the foregoing results demonstrated that an osteoconductive, remodelable, resorbable, and osteoinductive material can be added to a calcium phosphate cement while also maintaining the cement bone void fillers ability to be injected through a cannula.

Example 19

Analysis of Hydroxyapatite Cement Augmented with Xenograft Bone Particles to Improve Incorporation into Cancellous Defects Hydroxyapatite cement (HAC) is biocompatible and osteoconductive, but its slow resorption limits new bone formation. The addition of pores or biological materials helps resorption, but typically compromises short-term strength. To that end, the effects of adding decalcified xenograft bone on cement resorption, new bone formation, and strength were determined in an established animal model over ten weeks in order to examine whether processed xenograft bone particles would increase the incorporation and formation of new bone within HAC without decreasing its strength.

All procedures were approved by an institutional animal care and use committee. Briefly, in the first experiment, twelve six-month-old female New Zealand white rabbits were used to compare the biologic incorporation of xenograft versus allograft in a cancellous bone defect in the lateral femoral condyles. Drill-hole defects (8.0 mm long, 4.0 mm diameter) were prepared and filled with either allograft cancellous bone obtained from other rabbits or xenograft cancellous bone from young pigs. The bone graft was washed in organic detergent (Triton X-100) and morselized to an average particle size of 2 mm. Graft samples were impacted in a tube before being placed in the defect. Histologic analysis was done on femur samples after three (n=6) or ten (n=6) weeks. The amount of new bone was measured, and the degree of inflammatory response was evaluated and quantified using a 0-3 analog scale. Calcein was given three days before sacrifice to indicate newly forming bone.

In the second experiment, eight six-month-old female New Zealand white rabbits were used. Drill-hole defects (8.0 mm long, 5.0 mm diameter) were again prepared, but were filled with either HAC alone or HAC mixed with processed xenograft bone particles from young pigs (XBC) at a volumetric ratio of approximately 25%. The particles were elongated "needles" of cortical bone that were approximately 5 mm long and had a diameter of approximately 1 mm. The cortical bone particles were extensively washed, demineralized in dilute HCl, and rewashed. Micro-Computerized Tomography (μCT) scanning, decalcified and undecalcified histology, and mechanical indentation testing of the healing defects were performed after ten weeks (n=8). New bone and inflammatory/immune response were graded on a 0-3 scale, and calcein labeling was quantified as the percent area of new bone. Statistical analysis was by Student's t-tests.

Figure 27A:
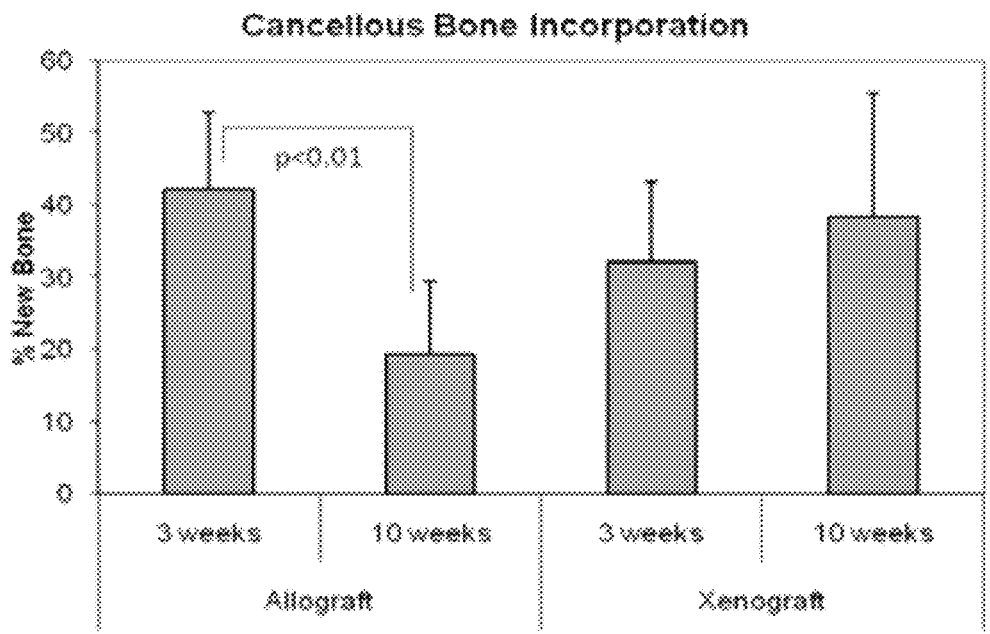
FIGS. 27A-27B include graphs illustrating the extent of cancellous bone incorporation (FIG. 27A) and the amount of inflammatory response (FIG. 27B) observed in cancellous bone defects at various time points, where the bone defects were filled with either allograft cancellous bone obtained from other rabbits (Allograft) or xenograft cancellous bone from pigs (Xenograft)
Figure 27B:
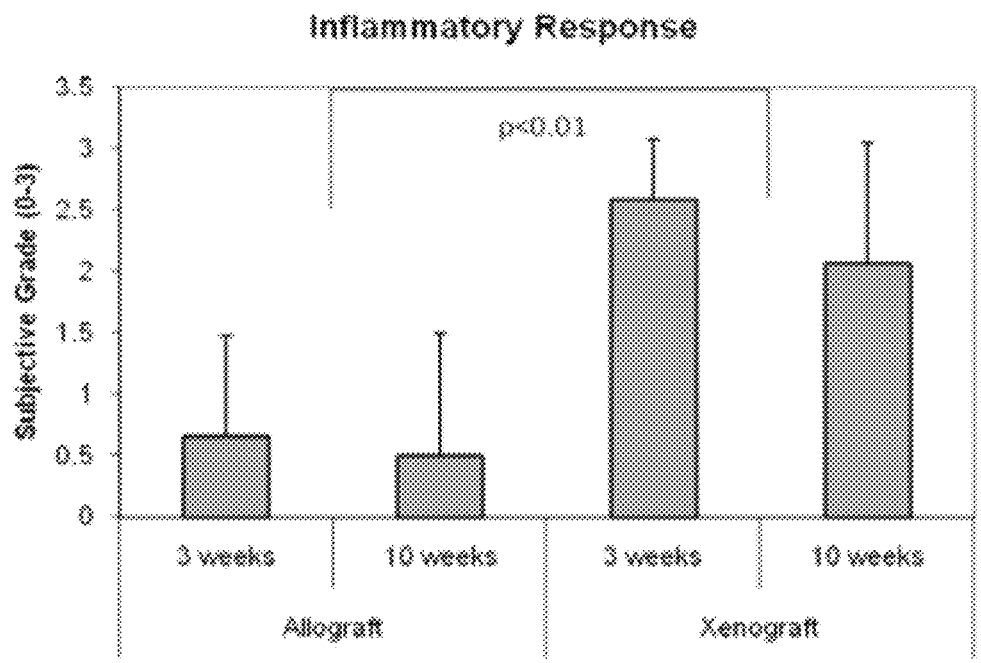

Subsequent to the analysis of the results from the first experiment, it was observed that the allograft cancellous bone healing response showed a rapid incorporation of the graft with extensive new bone formation at 3 weeks and nearly complete remodeling at 10 weeks (FIG. 26A) with a minimal inflammatory response and new bone formation (FIG. 26B). In many cases it was difficult to distinguish the allograft defects from normal bone at 10 weeks. The xenograft cancellous bone healing response was considerably slower (FIG. 26C) with a much larger inflammatory response at both 3 and 10 weeks and a generally higher level of new bone formation (FIG. 26D). By ten weeks, there was new bone formation in both groups, but with substantial new bone with the xenograft (FIG. 27A). The decrease in bone in the 10-week allograft group was because of extensive remodeling back to the normal state. Again, the inflammatory response was greater with xenograft and remained greater over 10 weeks (FIG. 27B).

Figure 28A:
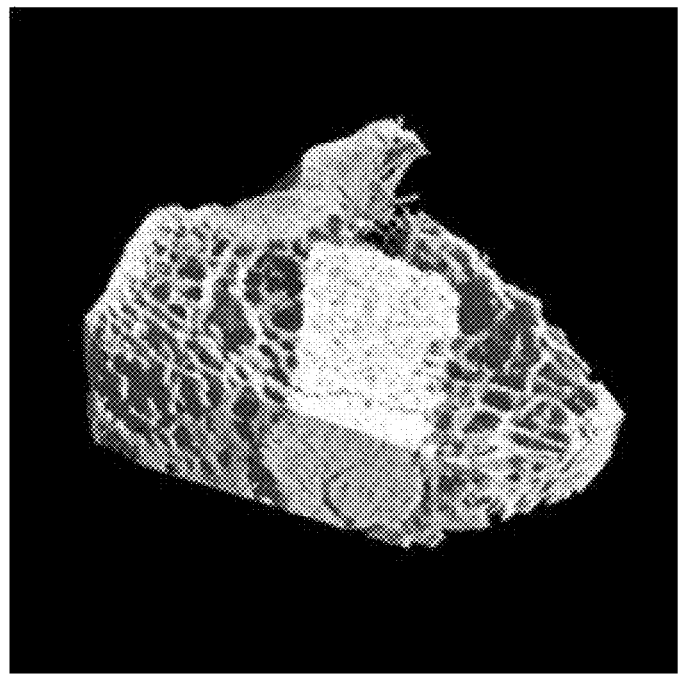
FIGS. 28A-28B are images of computer-generated, three-dimensional micro-CT reconstructions showing the extent of remodeling and new bone formation in drill hole defects in the femoral condyles of rabbits, where the drill hole defects were filled with either hydroxyapatite cement only (FIG. 28A) or a mixture of hydroxyapatite cement and xenograft bone particles (FIG. 28B)
Figure 28B:
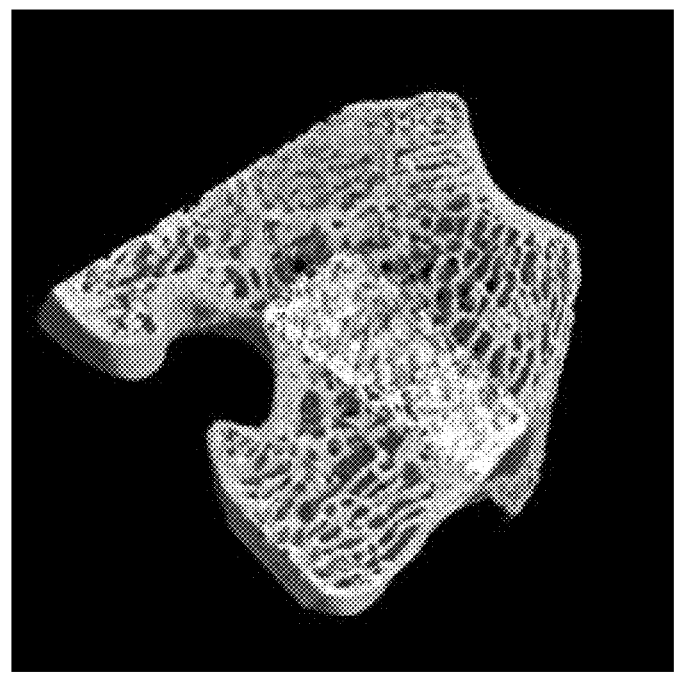

Subsequent to the analysis of the results from the second experiment, it was observed that, overall, the XBC group showed significantly more new bone formation than the HAC group throughout the defect (p<0.05). The XBC group, however, showed significantly more inflammatory/immune response than the HAC group (p<0.05). The three-dimensional μCT reconstructions showed that the HAC was basically inert, while the XBC took on an appearance suggestive of more extensive incorporation. Indeed, after 10 weeks, the HAC cylinder (FIG. 28A) was well fixed and appeared to be integrated with the cancellous bone, but without much remodeling, while the XBC cylinder (FIG. 28B) appeared to be remodeling more extensively with new bone formation. The indentation strength of HAC was significantly stronger than XBC only after ten weeks (p<0.05), but both grafts were stronger than normal cancellous bone at all times.

Figure 29A:
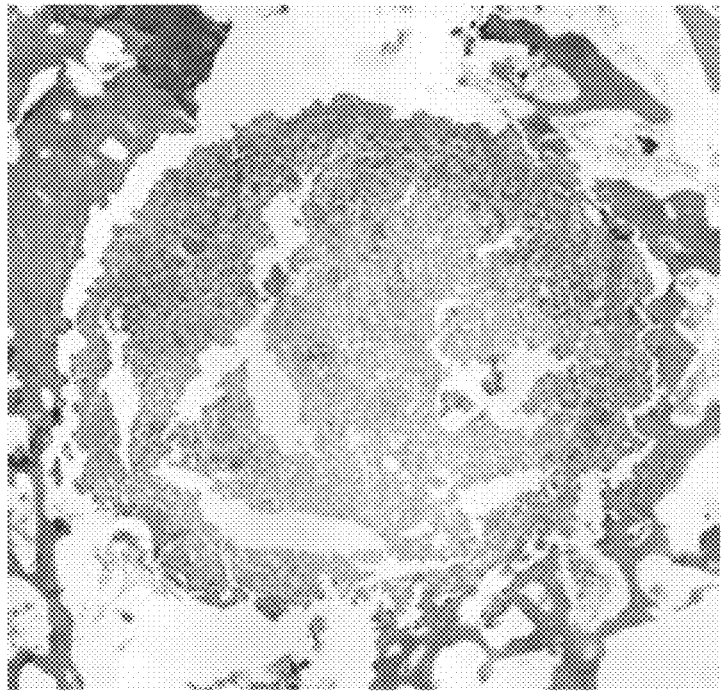
FIGS. 29A-29C include light microscopy images showing cellular activity and new bone formation in drill hole defects in the femoral condyles of rabbits, where the drill hole defects were filled with either hydroxyapatite cement only (FIG. 29A) or a mixture of hydroxyapatite cement and xenograft bone particles (FIG. 29B and FIG. 29C)
Figure 29B:
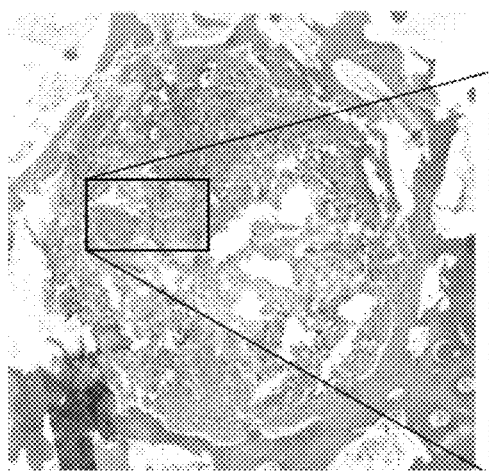
Figure 29C:
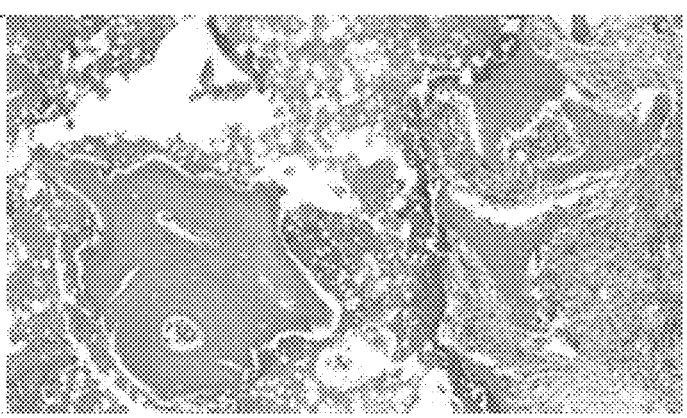
Figure 30A:
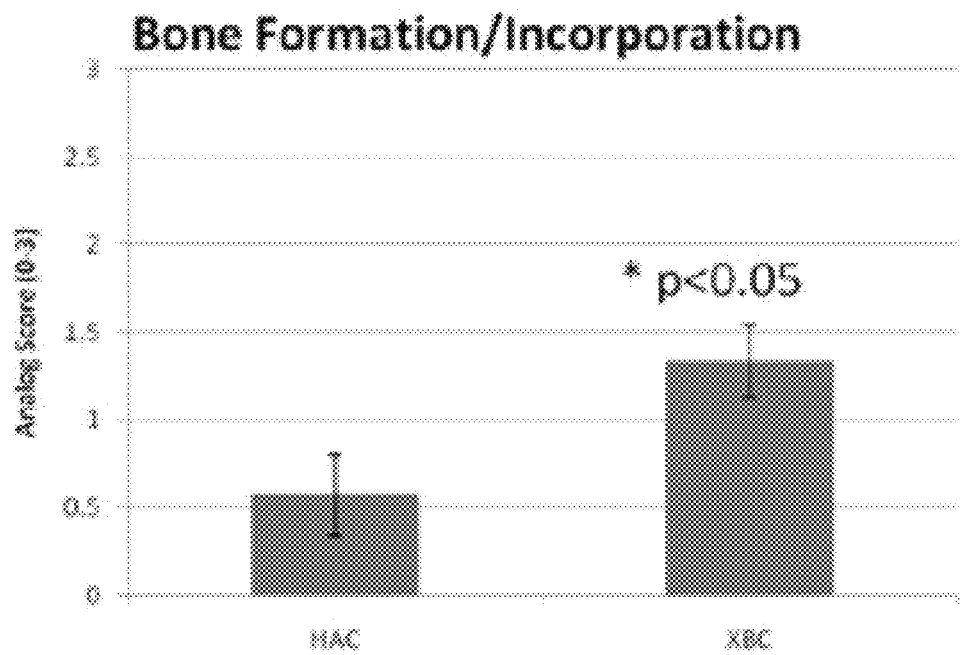
FIGS. 30A-30B include graphs illustrating the extent of incorporation and new bone formation (FIG. 30A) and the amount of inflammation and cellular activity (FIG. 30B) observed in drill hole defects in the femoral condyles of rabbits 10 weeks after the drill hole defects were filled with either hydroxyapatite cement only (HAC) or a mixture of hydroxyapatite cement and xenograft bone particles (XBC)
Figure 30B:
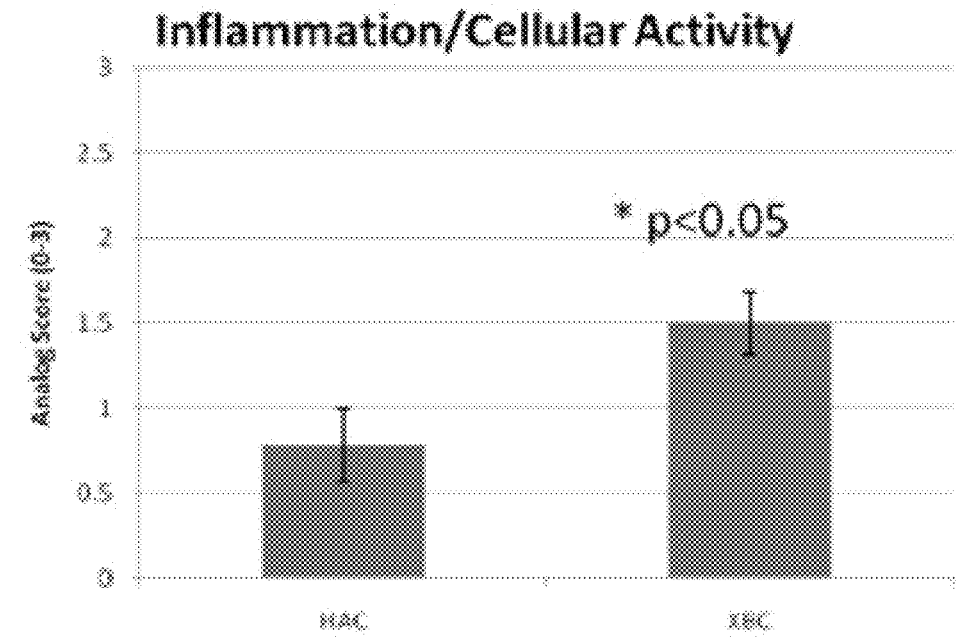
Figure 31A:
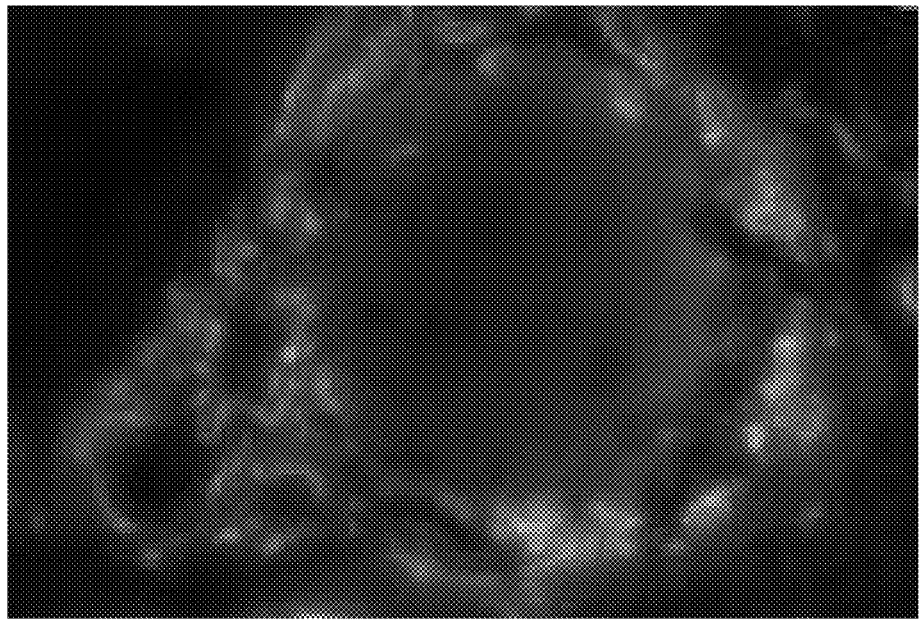
FIGS. 31A-31B and FIG. 31C include fluorescent microscopy images and a graph, respectively, showing new bone formation in calcein-labeled drill hole defects in the femoral condyles of rabbits 10 weeks after the drill hole defects were filled with either hydroxyapatite cement only (FIG. 31A) or a mixture of hydroxyapatite cement and xenograft bone particles (FIG. 31B)
Figure 31B:
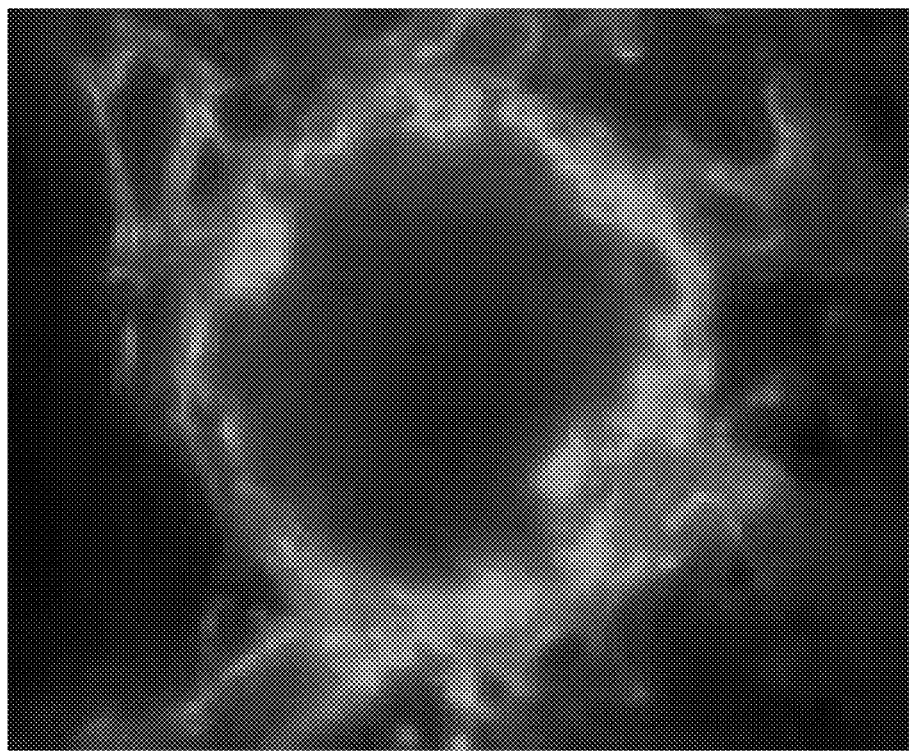
Figure 31C:
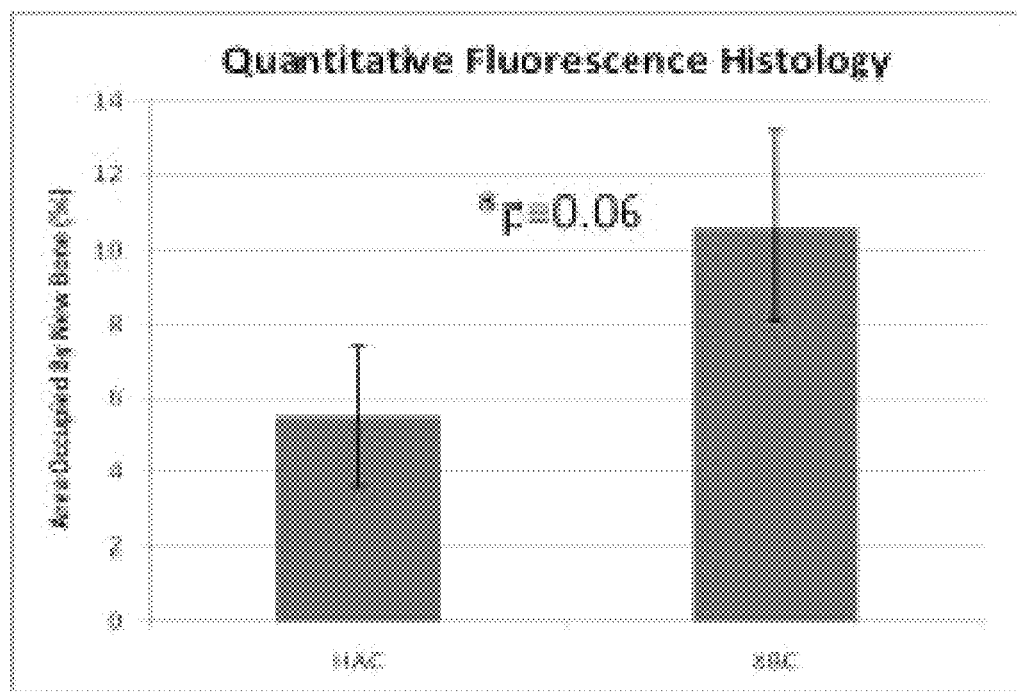
Figure 32:
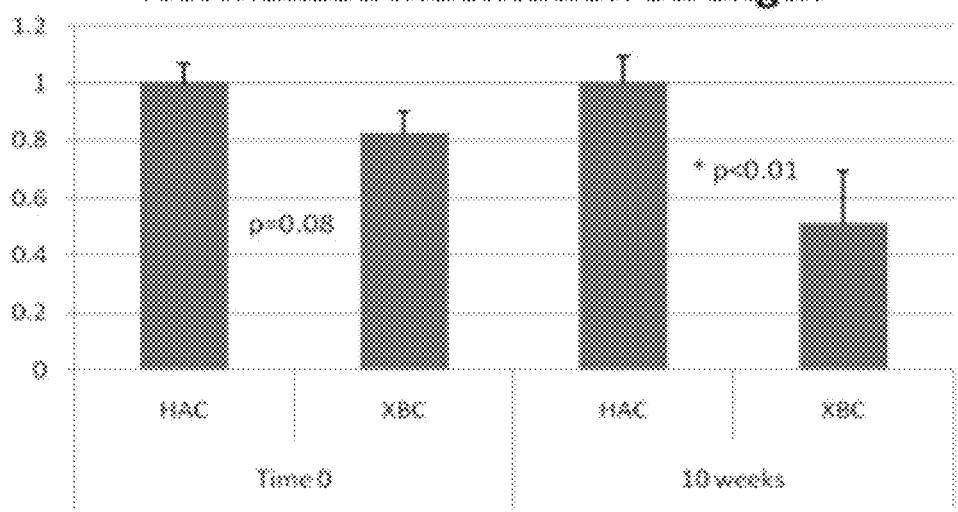
FIG. 32 is a graph showing the indentation strength of bone graft compositions comprised of either hydroxyapatite cement only (HAC) or a mixture of hydroxyapatite cement and xenograft bone particles (XBC) at the time of inserting the composition or 10 weeks after inserting the compositions in drill hole defects in the femoral condyles of rabbits.

In the second experiment, after 10 weeks, there was no new bone formation within the HAC filled defect (FIG. 29A), while the XBC filled defect (FIG. 29B) had several regions of extensive cellular activity with new bone formation (see, e.g., FIG. 29C). After 10 weeks, there was also significantly more new bone formation within the XBC defects compared to HAC (FIG. 30A; p<0.05). There was also significantly more inflammatory/cellular response in the XBC compared to HAC (FIG. 30B; p<0.05). Further, after 10 weeks, there was a trend toward more new bone formation activity within the XBC defects (FIG. 31A), as indicated by calcein labeling, compared to HAC (FIG. 31B) (see also FIG. 31C). Finally, blunt indentation testing using a 1.5 mm diameter indenter showed no significant difference at time zero, but the XBC resisted significantly less indentation force after 10 weeks in vivo (FIG. 32). It should be noted that the XBC remained stronger than cancellous bone after 10 weeks.

The results from the foregoing experiments indicated that adding xenograft to HAC created a bioactive composite that was more rapidly incorporated, resorbed, and replaced by new bone. The presence of the xenograft particles created a vigorous inflammatory response, but, without wishing to be bound by any particular theory, it was thought that there may be some benefit to the resorption rate of the HAC component of the XBC due to the infiltration of cells. That volumetric inclusion of rapidly resorbed bone graft did not compromise the initial indentation strength of the filled defect relative to normal cancellous bone.

Example 20

Allograft Augmented Calcium Phosphate Cement as a Self-Hardening Bone Graft Substitute An established animal model was utilized to determine the effects of adding specially-engineered shapes of partially demineralized allograft cortical bone on short term cement behavior and biocompatibility, and to further assess whether the presence of processed bone particles would increase the incorporation rate of the cement without compromising its handling characteristics. Briefly, a six-month-old female New Zealand white rabbit was used to evaluate the handling characteristics and biologic incorporation of allograft augmented calcium phosphate cement in cancellous bone defects in the lateral femoral condyles of both hind limbs. All procedures were first approved by the institutional animal care and use committee. First, drill-hole defects (8.0 mm long, 5.0 mm diameter) were prepared and filled with a novel calcium phosphate cement augmented with specially engineered shapes of partially demineralized allograft cortical bone. The particles were elongated "dumbbells" of cortical bone approximately 2.5 mm long, 1.5 mm diameter at the ends and 0.5 mm diameter in the center portion (see FIG. 1A). Prior to mixing with the cement, the particles were machined from a donor rabbit femur, extensively washed, demineralized in dilute HCl, and rewashed. The outer layer of each dumbbell was demineralized to a thickness of approximately 100 to 200 μm. The cleaned particles were allowed to dry in air in an oven at 37° C. for 24 hours and were then sealed in sterile airtight containers prior to use.

At the time of surgery, and subsequent to the creation of the defect, the cement was mixed by combining 2.4 g of calcium phosphate cement powder and thirty dumbbell-shaped particles (see FIG. 1A) of partially demineralized bone (0.064 g). The partially demineralized bone particles were first added to the container of calcium phosphate cement powder and mixed thoroughly with a spatula to evenly disperse the bone within the powder. Next, a sodium phosphate solution was added to the dry mixture of calcium phosphate cement and partially demineralized bone particles. The material was then mixed for 30 sec to form a paste with a uniform consistency. Once a uniform consistency was obtained, a spatula was then used to fill the drill hole defect that was created in the distal femur of the rabbit. As a result of filling the defect with the paste, each void was made to contain approximately 9 to 12 pieces of demineralized bone, or, in other words, about 10 to about 15% demineralized bone particles by volume of the defect. The outer surface of the defect was then covered with a plug of bone wax to stop bleeding and to prevent periosteal osteogenesis in the defect. The wound was then closed and the process was repeated for the opposite leg.

The rabbit was subsequently allowed to recover and ambulate normally and eat a normal diet ad libitum. After ten days, the rabbit was sacrificed, and high resolution μCT scanning (14 μm voxels) was performed on both distal femurs before they were prepared for decalcified histology using hemotoxylin and eosin staining.

Figure 33:
FIG. 33 is a micro-computerized tomography (micro-CT) image of a drill hole defect in the lateral femoral condyle of a rabbit that was filled with a bone graft composition of the presently-disclosed subject matter that comprised calcium phosphate cement and dumbbell-shaped bone particles.
Figure 34:
FIG. 34 is a copy of the micro-CT image shown in FIG. 33, but with the cement-filled area of the bone defect highlighted and with the bone particles within the cement further highlighted and shaded white.

Upon obtaining the results of these experiments, the micro-CT scan image (FIG. 33) shows the extent to which the experimental bone substitute cement was able to fill the defect and the extent to which the hardened cement extends and the presence of several partially demineralized allograft "dumbbells." Also, the allograft dumbbells are clearly visible at several locations within the filled defect (see, e.g., FIG. 34), and the demineralized layer on the bone particles is clearly visible due to the radiolucency of that layer. Further, other allograft bone pieces could be seen at other levels in different regions of the defect.

Figure 35:
FIG. 35 is a light microscopy image showing a cross-section of a drill hole defect in the lateral femoral condyle of a rabbit that was filled with a bone graft composition comprising calcium phosphate cement and allograft, dumbbell-shaped bone particles.
Figure 36:
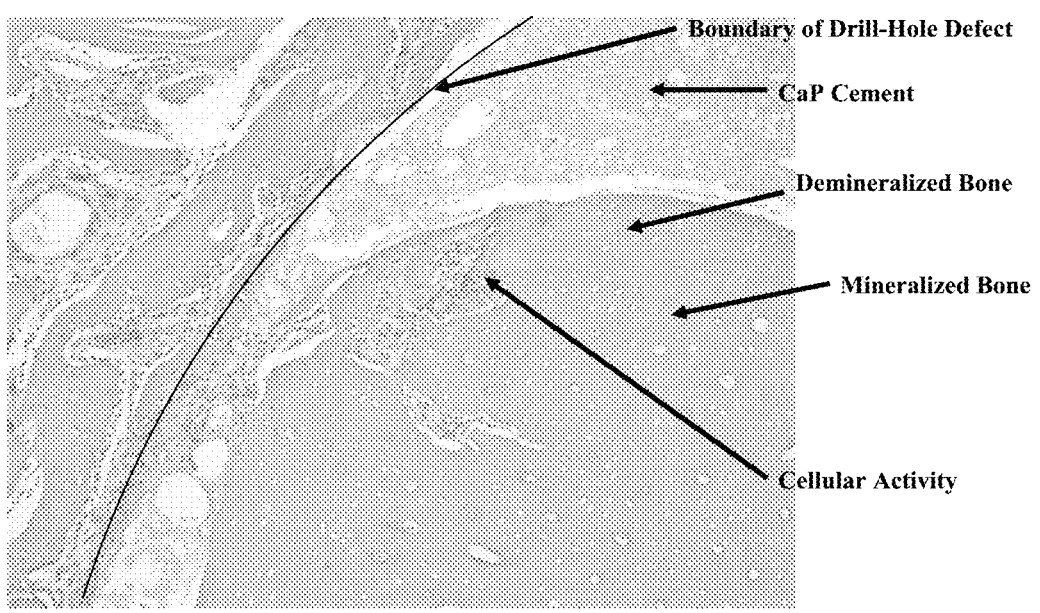
FIG. 36 is a light microscopy image showing a portion of the microscopy image shown in FIG. 35 at a higher magnification (100×), and further showing cellular activity from the defect boundary into the bone particle via the demineralized layer and a boundary between the demineralized bone layer and the mineralized bone.
Figure 37:
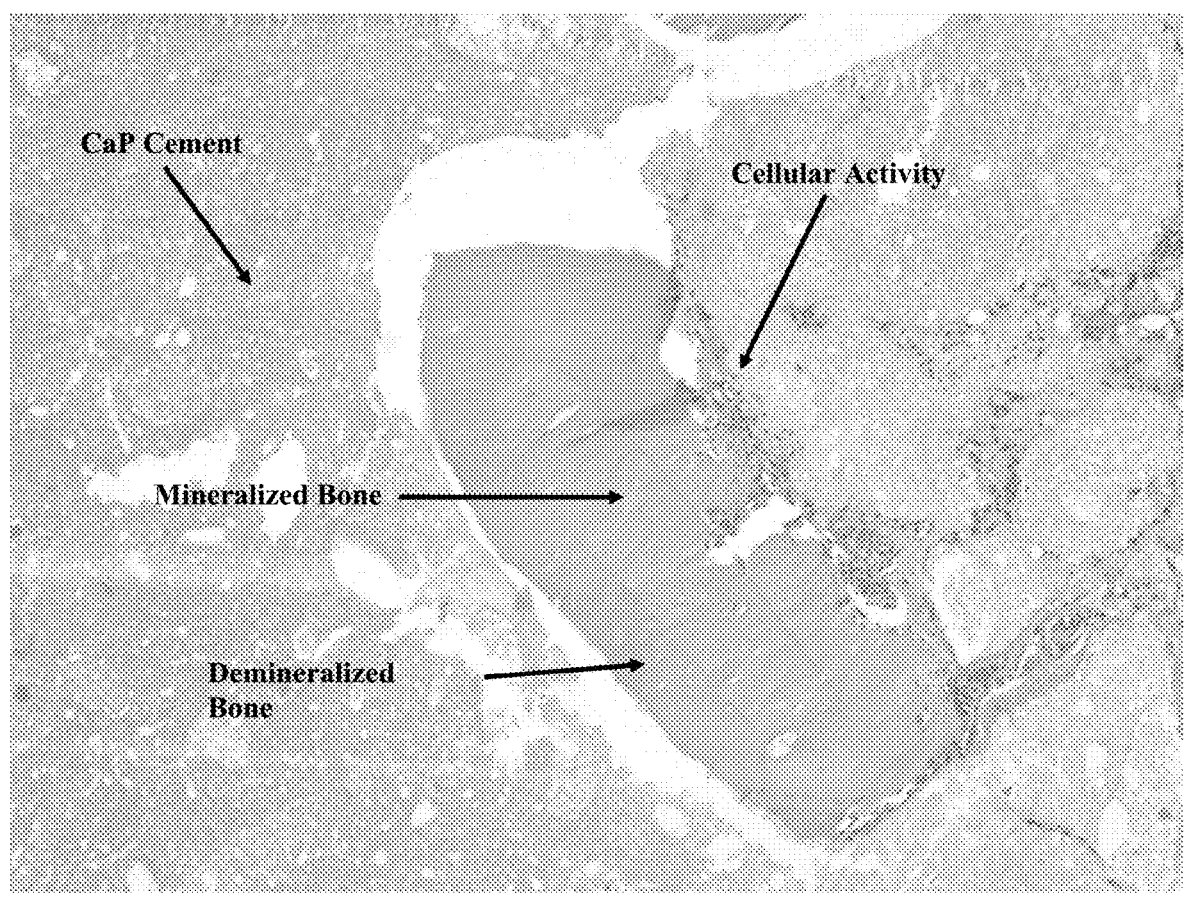
FIG. 37 is another light microscopy image showing a portion of the microscopy image shown in FIG. 35 at a higher magnification (100×), and further showing cellular activity and incorporation of an allograft particle from the defect boundary via the demineralized layer and a boundary between the demineralized bone layer and the mineralized bone.
Figure 38:
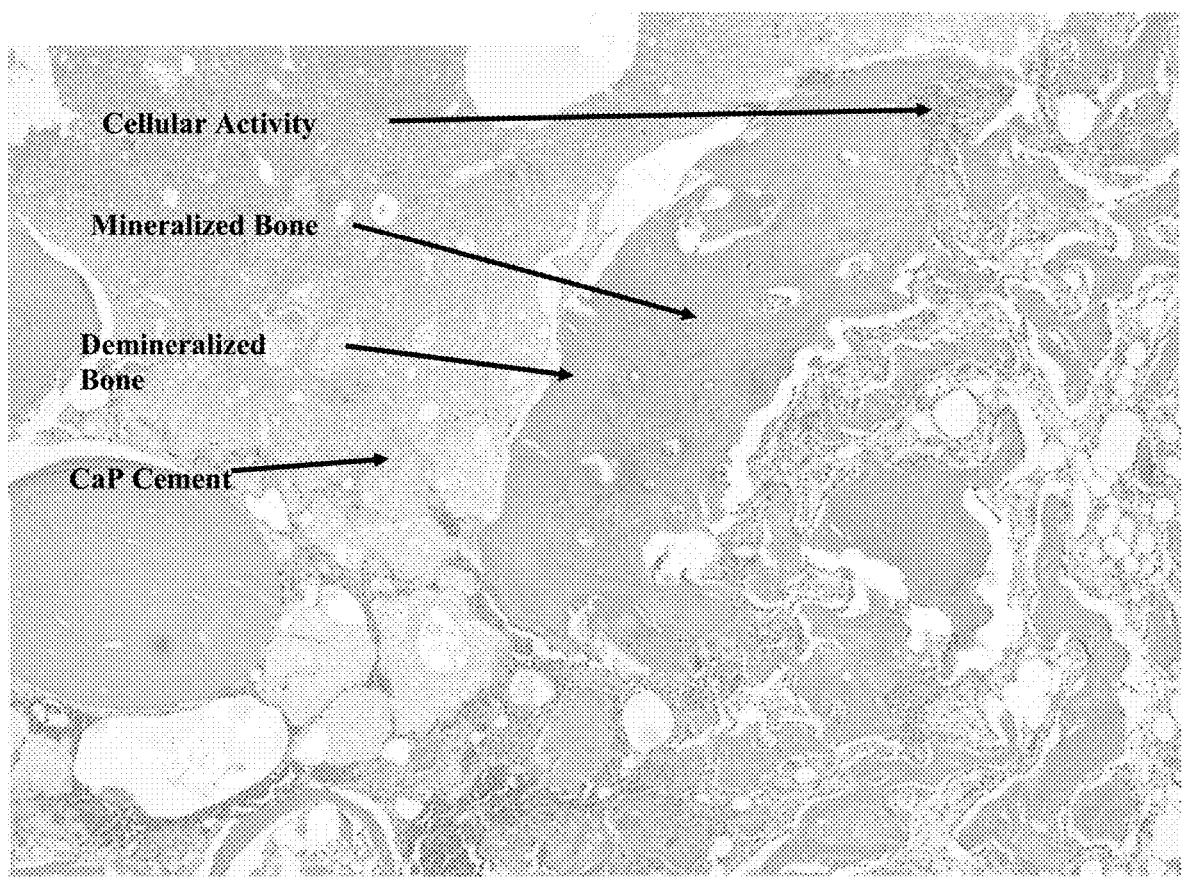
FIG. 38 is also a light microscopy image showing a portion of the microscopy image shown in FIG. 35 at a higher magnification (100×), and further showing cellular infiltration and incorporation of the allograft, dumbbell-shaped bone particles.

The histology from the above-described experiments showed the extent to which the experimental cement filled the defect (FIG. 35), and clearly showed that there was a distribution of allograft bone pieces throughout the cross-section. A single "dumbbell" was seen in a horizontal orientation and others are at various orientations outside the plane of the slice. At a higher magnification (100× magnification) of the histology sections, cellular infiltration at the boundary of the defect into the demineralized layer of the allograft bone piece was observed (FIG. 36), and the incorporation of an allograft particle from the defect boundary via the demineralized layer was also observed along with a faint mark between the demineralized bone layer and the mineralized bone (FIG. 37). Additional histological sections showed the cellular infiltration and incorporation of allograft particles with a faint mark between the demineralized bone layer and the mineralized bone (FIG. 38).

Figure 39A:
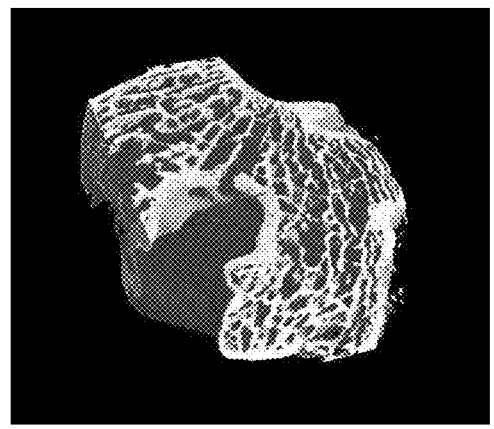
FIGS. 39A-39C are images showing a three-dimensional micro-CT reconstruction of the distal femur region of a rabbit, where a drill hole defect in that region was filled with a bone graft composition of the presently-disclosed subject matter comprising calcium phosphate cement and dumbbell-shaped bone particles, including an image of the entire distal femur region (FIG. 39A), an image showing a transverse trim of the reconstruction through the middle of the defect (FIG. 39B), and an image where the reconstruction has been trimmed from the top and front (FIG. 39C)
Figure 39B:
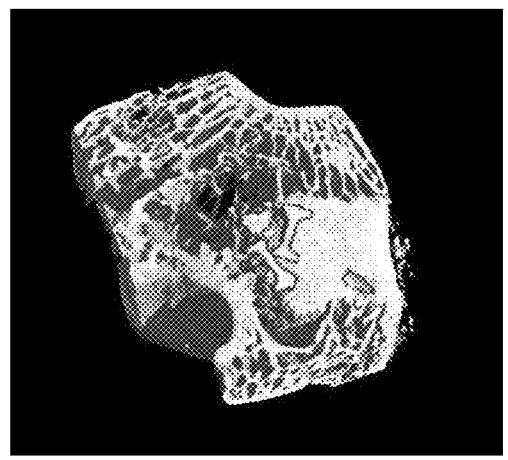
Figure 39C:
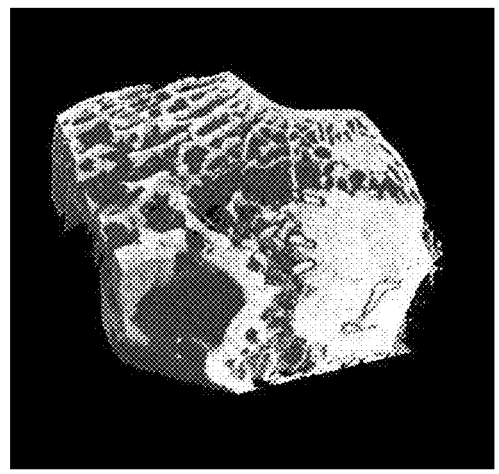

A 3-D micro-CT reconstruction (FIG. 39A) of the distal femur region containing the filled drill-hole defect was further used to examine the ability of the bone graft composition to treat the drill hole defect. In this regard, a transverse trim of the reconstruction through the middle of the defect showed the extent to which the hardened cement extended through the entire region of the defect and the presence of several partially demineralized allograft "dumbbells" within the defect itself (FIG. 39B). When the reconstruction of the defect was trimmed from the top and front, the allograft bone pieces could be seen at other levels in different regions of the defect (FIG. 39C). Also, the demineralized layer on the bone pieces was clearly visible due to its radiolucency.

Figure 40A:
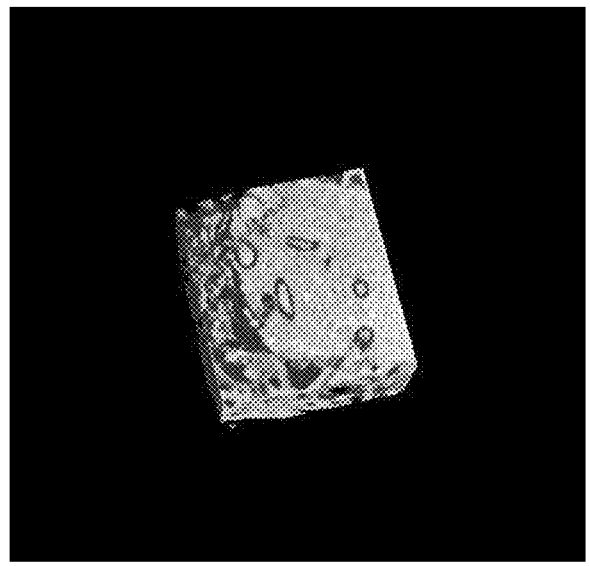
FIGS. 40A-40B are images showing an approximately 2 mm thick slab micro-CT reconstruction of the distal femur region of a rabbit, where a drill hole defect in that region was filled with a bone graft composition of the presently-disclosed subject matter comprising calcium phosphate cement and dumbbell-shaped bone particles, where FIG. 40B isolates the lower-density demineralized layer covering each specially-shaped bone particle.
Figure 40B:
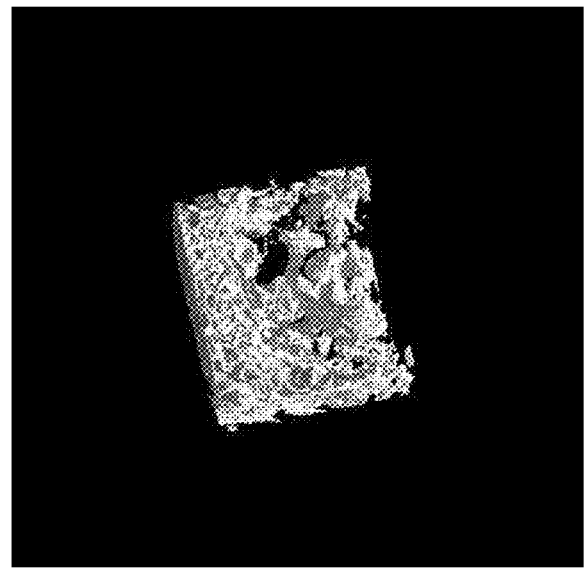

To further examine the bone graft composition, an approximately 2 mm thick slab reconstruction of the cement filled defect region was created. That reconstruction showed cross-sections of several cortical allograft "dumbbells" within the cement-filled defect region (FIG. 40A). Additionally, the same slab, viewed with a different threshold, showed the collagen (demineralized) layer on the allograft "dumbbells" (FIG. 40B). Regions outside the defect region were also highlighted because they have the same CT density as the collagen. In both reconstructions, however, the included dumbbell-shaped bone particles were interconnected and were distributed through the defect giving a trabecular-like appearance.

Figure 41A:
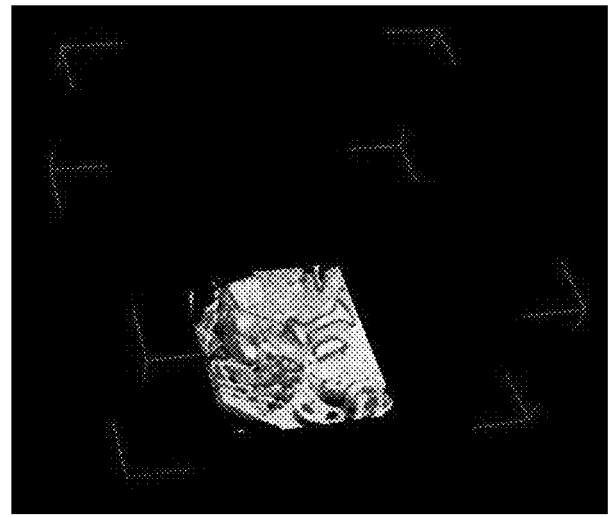
FIGS. 41A-41B are images showing an approximately 5 mm thick slab micro-CT reconstruction of the distal femur region of a rabbit, where a drill hole defect in that region was filled with a bone graft composition of the presently-disclosed subject matter comprising calcium phosphate cement and dumbbell-shaped bone particles, where FIG. 41B isolates the lower-density demineralized layer covering each specially-shaped bone particle.
Figure 41B:
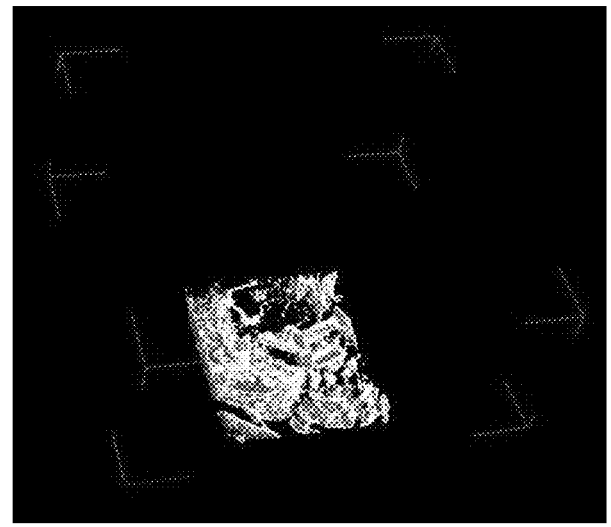

A 0.5 mm thick slab reconstruction of the cement filled defect region further showed cross-sections of at least two cortical allograft dumbbells (FIG. 41A). The same slab with a different threshold also showed the collagen (demineralized) layer on the allograft dumbbell-shaped particles (FIG. 41B). Regions outside the defect region were also highlighted because they had the same CT density as the collagen. Similar to the reconstructions discussed above, the 0.5 mm slab also revealed dumbbell-shaped particles that were interconnected and were distributed throughout the defect, giving a trabecular-like appearance.

The foregoing results demonstrated that a bone substitute cement comprised of calcium phosphate cement and dumbbell-shaped cortical bone particles could be handled and delivered similar to existing bone substitute cements. Further, the distribution of the specially processed allograft bone particles was evident from the histology sections and, where the particles interacted with the host tissue at the defect boundaries, there was a rapid infiltration of cells and evidence of resorption of the graft and calcium phosphate cement. Healing and new bone formation was also apparent in some locations after only 10 days.

The dumbbell-shaped bone particles also appeared to improve the distribution of the bone graft and to increase the likelihood of contact with the defect boundaries. Additionally, it appeared that the demineralized layer facilitated the resorption and infiltration of the bone substitute and promoted incorporation and new bone formation after ten days in vivo.

Example 21

Analysis of a Bone-Augmented Calcium Phosphate Cement as a Self-Hardening Bone Graft Substitute in a Rabbit Model To determine the effects of adding specially-shaped, partially demineralized human cortical bone on short-term cement behavior and biocompatibility, and to further assess whether the presence of those processed bone particles increases the incorporation rate of the cement without compromising its handling characteristics, an established animal model is utilized. Briefly, 36 six-month-old female New Zealand white rabbits are used to evaluate the handling characteristics and biologic incorporation of allograft-augmented calcium phosphate cement in cancellous bone defects in the lateral femoral condyles of both hind limbs. All procedures are approved by an institutional animal care and use committee. First, drill-hole defects (8.0 mm long, 5.0 mm diameter) are prepared and filled with a bone graft composition of the presently-disclosed subject matter comprising a calcium phosphate cement augmented with specially-shaped, partially demineralized allograft cortical bone. The particles are elongated dumbbell-shaped pieces of cortical bone approximately 2.5 mm long, 1.5 mm wide at the ends, and have a 0.5 mm thickness in the center portion. Prior to mixing with the cement, the cortical particles are machined, extensively washed, demineralized in dilute HCl, and rewashed, lyophilized, and sterilized. The outer layer of each processed bone particle is then demineralized to a thickness of approximately 50 to 200 µm.

At the time of surgery, and subsequent to the creation of the defect, the sterile cement powder is mixed by combining calcium phosphate cement powder and processed particles of partially demineralized bone. The partially demineralized bone is first added to the container of calcium phosphate cement powder and mixed thoroughly with a spatula to evenly disperse the bone within the powder. Next, a sodium phosphate solution is added to the dry mixture of calcium phosphate cement and partially demineralized bone. The material is then mixed for 30 sec to form a paste with a uniform consistency. Once a uniform consistency is obtained, a spatula is then used to fill the drill hole defect created in the distal femur of the rabbit. As a result of filling the defect with the paste, each void is made to contain about 10 percent to about 15 percent demineralized bone structures by volume of the defect. The wound is then closed and the process is repeated for the opposite leg.

The rabbits are subsequently allowed to recover and ambulate normally and eat a normal diet ad libitum. After three weeks (n=12), 8 weeks (n=6), 12 weeks (n=12), and 24 weeks (n=6), the rabbits are sacrificed and high resolution µCT scanning (14 µm voxels) is performed on both distal femurs before they are prepared for decalcified and/or undecalcified histology. Some samples are separately prepared for mechanical testing to measure the compressive strength of the repaired defect together with surrounding bone at various time points.

At each time point, the histology reveals that there is more new bone formation within the treated defects containing the partially demineralized bone. Analysis of the mechanical behavior of the bone and defect also reveals that the strength of the repair is maintained at or above the baseline strength of representative cancellous bone during the experimental timeframe. Together, these results demonstrate that a bone graft composition of the presently-disclosed subject matter comprising a calcium phosphate cement augmented with specially-engineered shapes of partially demineralized allograft cortical bone, can effectively be used as part of a method for treating a bone defect.

Example 22

Osteoinductivity of a Calcium Phosphate Based Composite Cement Containing Processed Cortical Bone Particles Assessment of ectopic bone formation in an athymic nude rat model after implantation in intramuscular or subcutaneous pockets is the current standard for assessing the osteoinductive properties of implantable materials. As such, an athymic nude rat model is thus utilized in an experiment to assess the osteoinductive properties of the bone graft compositions of the presently-disclosed subject matter and to compare those compositions to other materials. Briefly, test bone graft compositions are prepared by combining a calcium phosphate powder, a setting solution, and partially demineralized, specially-shaped, bone particles. The test samples are then formed into a 5 mm disc with a 0.5 mm thickness, and the discs are bilaterally implanted in four (4) animals in subcutaneous muscle pouches in the axiliary region of each the nude athymic male rats. Once anesthetized, a small incision is made and an opening is created through the skin, subcutaneous tissue, and fascia of each animal. A muscle pouch is then formed by cutting in the same direction as the muscle fibers, and the scissors are then used and spread to create a pouch in the muscle. The 0.1 ml test sample is then carefully inserted using forceps and, once the test article is verified to be properly in place and maintaining form, the muscle pocket is sutured closed. The surgery is then repeated in the bilateral implant site. If necessary an additional half dose of ketamine/xylazine is administered to maintain a level of anesthetization sufficient to complete the implantation procedure.

Implant sites are harvested en bloc after 28 days post-implantation and sent for histological preparation. The histological slides are scored for osteoinductivity and inflammatory responses are recorded in accordance with the scoring system of Edwards et al. (1998), which makes use of a 0-4 scale, where 0 indicates no evidence of bone formation, and 1, 2, 3, and 4 indicate less than 25%, 26-50%, 51-75%, and greater than 75%, respectively, of implant surface involved in new bone formation. In addition, bone maturity is scored in accordance with Katz et al. (2006). During the scoring, each of the samples are randomized and blinded to the investigators.

Upon analysis of the scoring, it is observed that, on average, the implanted test disks incorporating the processed bone reinforcing elements produces a valid osteoinductive score compared to the control samples with 100% cement, indicating that adding specially-shaped and partially demineralized bone particles to a calcium phosphate cement improve its osteoinductive properties, and further indicating that both the biologic behavior (incorporation, remodeling, new bone formation) and the mechanical behavior of bone cement compositions can be improved by the presence of the specially-shaped bone materials.

Example 23

Aqueous Buffering of the Cement Powder, Processed Bone Particles, and Setting Liquid Combination The presence of the specially-processed bone particles of the presently-disclosed subject matter allows some flexibility in the handling of the ratios of powder to liquid when preparing cement pastes. Further, the presence of the bone particles with a demineralized component or additional porosity allows for water to be absorbed or released by the bone particles in a way that positively affects the handling and/or strength characteristics of the cement. Moreover, the specially-shaped bone particles have a decalcified layer that gives the particles the ability to absorb small amounts of moisture. Each of these characteristics was considered to be important as the mass of water or other biological fluid that the specially-shaped bone particles can hold can be considered in light of the amounts of osteogenic proteins, water, blood, antibiotics, and other such materials that may be held by the particles. In this regard, it is additionally thought that the residual moisture the specially-shaped bone particles can absorb may also be used to alter the handling characteristics of calcium salt bone void fillers.

Thus, to more precisely determine the amount of moisture the individual, specially-shaped bone particles are capable of retaining, five separate batches of a known amount of specially-shaped bone particles were first dehydrated at 40-42° C. with convection for four hours and then each batch was weighed. This mass was recorded as the batch of specially-shaped bone particles dehydrated weight. The batch of particles was then super-hydrated by covering the particles with deionized water and leaving the particles under vacuum for one hour. After hydrating the particles, each particle was removed from the water bath and the residual moisture on the surface of the individual particles was removed with a lint-free cloth by briefly blotting the surface. Once the surface moisture was removed, the particles were then re-weighed, and that subsequent weight was considered the fully-hydrated weight. The difference in mass from the dehydrated to the fully-hydrated state was then used to calculate the mass of water. Additionally, to further confirm the mass of the dehydrated bone particles, the particles were then placed back in the dehydrator and left under convection at 40-42° C. until the initial mass of the batches plateaued. The batches were weighed at multiple time points. Initially the mass decreased rapidly in the first few time points, with the difference in the mass of the batches between time points then decreasing gradually as the elapsed time increased.

TABLE 18

Differential Weights of Hydrated and Dehydrated Bone Shapes

| Group | Weight of Tr | Fully Dehydrated | Hydrated | Difference | % | Redried 5 min | 15 min | 40 min |
|---|---|---|---|---|---|---|---|---|
| 1 | 1.5324 | 17.9535 | 18.5824 | 0.6289 | 41.0402 | 18.3544 | 18.1622 | 17.9999 |
| 2 | 1.532 | 18.0937 | 18.6642 | 0.5705 | 37.2389 | 18.4725 | 18.3288 | 18.1301 |
| 3 | 1.5335 | 17.9426 | 18.6457 | 0.7031 | 45.84936 | 18.496 | 18.2766 | 18.0053 |
| 4 | 1.5317 | 17.9541 | 18.6085 | 0.6544 | 42.72377 | 18.4104 | 18.2049 | 18.0077 |
| 5 | 1.5497 | 18.1871 | 18.8293 | 0.6422 | 41.44028 | 18.7086 | 18.5136 | 18.255 |
| Mean | | | | | 41.6585 | | | |
| SD | | | | | 3.108894 | | | |

Upon analysis of the results from these experiments, and as shown in Table 17 above, it was determined that the specially-shaped and processed, partially demineralized cortical bone particles (Tr) can retain approximately 40% of their mass in water. At the ratios of powder to liquid typical employed in the foregoing in vivo experiments, this amount of water represented a significant variation in the amount of liquid that could be mixed with the powder to form a workable cement paste.

Example 24

Autologous Factor Carrying Capacity of the Included Bone Particles and Mechanical Effects of Including Autologous Factors As noted, the presence of the specially-shaped bone particles allows additional flexibility in the handling of the ratios of powder to liquid when preparing cement pastes. This property, in turn, is believed to further allow blood (or other autologous factors) from a subject to be used to precondition the included bone particles for better biological behavior in vivo. Further, the presence of the bone particles with a demineralized component or additional porosity is also believed to allow for autologous factors (blood, serum, cells, bone marrow aspirate, etc.) to be absorbed or adsorbed by the bone particles for biologic benefits in a way that does not negatively affect the handling and/or strength characteristics of the cement. To assess the extent of these benefits, experiments are performed to determine whether adding a small amount of blood to dry bone particles, before mixing the particles with cement powder and setting liquid, would negatively affect the subsequent mechanical properties of the final product.

Briefly, and similar to the experiments described above, mechanical testing experiments using calcium phosphate cement with 10% by volume partially demineralized, specially-shaped cortical bone particles are undertaken to determine the mechanical behavior effects of adding blood to the specially processed cortical bone particles. In these experiments, a calcium phosphate cement consisting of tetracalcium phosphate (TTCP) powder, monocalcium phosphate (MCP) powder, calcium carbonate powder is used and, similar to the methodology described above, cortical bone particles are also created through a machining process that yields specially-shaped particles approximately 2.5 mm in length, 1.5 mm in width at each end, and 0.5 mm thickness on average with a 0.5 mm wide center portion (see FIG. 1A). These bone particles are again obtained from the diaphyseal regions of porcine femora and tibae and are partially demineralized using the methodology described above. After the particles are formed and dehydrated, they are then weighed to represent a 10% volume ratio of the total mix (as described above in previous examples). Before the dry components of cement powders and bone particles are mixed together, a small quantity (0.25 cc) of human blood is mixed with the bone particles (0.345 g), and these are allowed to soak in a shallow bowl for approximately 2 minutes. Next, the bone particles are removed from the blood and mixed with the dry cement powder in sufficient quantity to create 3 cc of cement paste.

Test samples are then created by combining the dry materials with an appropriate amount of setting liquid, mixing with a thin metal spatula, until a consistent wet paste is formed. Next, the materials are spread into cylindrical Teflon® (Du Pont de Nemours and Company Corporation, Wilmington, Del.) molds. The molds are designed to create test samples 20 mm in length with a diameter of 8 mm.

The bending test is then performed using a three-point bending fixture as described above (see, e.g., FIG. 3). Upon analysis of the results from these experiments, it is observed that adding blood to the specially-shaped and partially demineralized bone particles prior to combining them with a calcium phosphate cement does not significantly affect the mechanical properties of the resulting bone graft composition in the demanding loading mode of bending.

Example 25

Elution Properties of the Combined Cement and Bone Particles for Delivery of Therapeutic Agents, Including Antibiotics and Growth Factor Proteins To assess the ability of the bone graft compositions of the presently-disclosed subject matter to be utilized as delivery systems for various therapeutic agents, experiments were performed to assess the elution of various agents of interest from the hardened end product when it is incubated in a liquid environment. Briefly, in these experiments, to test the elution of growth factor proteins such as bone morphogenetic proteins (BMPs), an analog protein lysozyme was used, and to test antibiotic elution, vancomycin was used. A bone graft composition of the presently-disclosed subject matter that was comprised of calcium phosphate, consisting of tetracalcium phosphate (TTCP) powder and dicalcium phosphate anhydrous (DCPA) powder, was used in these experiments plus approximately 25% specially-shaped cortical bone particles (by volume). Lysozyme (Sigma, St. Louis, Mo.) was pre-adsorbed onto the bone particles before they were added to the cement to achieve 0.0168 or 0.168% loading. In this regard, lysozyme was dissolved in 0.85 mL of setting solution at a concentration of 0.44 and 4.4 mg/mL and was then added to the bone particles. The protein-bone mixtures were then rotated at room temperature for 30 min, after which the mixture was added to 2.225 g of calcium phosphate powder. Vancomycin (Sigma, St. Louis, Mo.) was dry-mixed with the calcium phosphate powder (2.225 g) and bone particles prior to addition of the setting solution (0.85 mL). Either 0.3, 3.0, or 10.0% (6.68, 66.8, or 222.5 mg) of antibiotic was added to each sample. Each batch of antibiotic- or protein-loaded cement/bone mixture was spread in a mold to form samples of 19 mm diameter and 1.5 mm thickness. For comparison, drug-free cement samples were made using 2.225 g cement, bone particles, and 0.85 mL setting solution. After allowing samples to set overnight at room temperature, release experiments were conducted.

For the release experiments, samples were immersed in 3 ml of 150 mM phosphate-buffered saline, pH 7.4, and incubated at 37° C. with gentle shaking. All of the supernatant was collected and replaced daily to maintain sink conditions and a constant volume. Vancomycin concentration was determined by measuring absorbance at 280 nm (Biotek PowerWave HT UV microplate reader, Bio Tek Instruments Inc., Winooski, Vt.) and comparing to a standard curve constructed with the antibiotic. Lysozyme concentration was measured using the MicroBCA Protein Assay (Thermo Fisher, Waltham, Mass.) according to the manufacturer's instructions, with the exception that the samples were incubated at 37° C. for two hours following addition of the working reagent to the supernatant. Absorbance was measured at 570 nm and compared to standard curves prepared with lysozyme. For both the antibiotic and protein assays, results from drug-free samples were used to correct for nonspecific biomaterial effects.

Figure 42A:
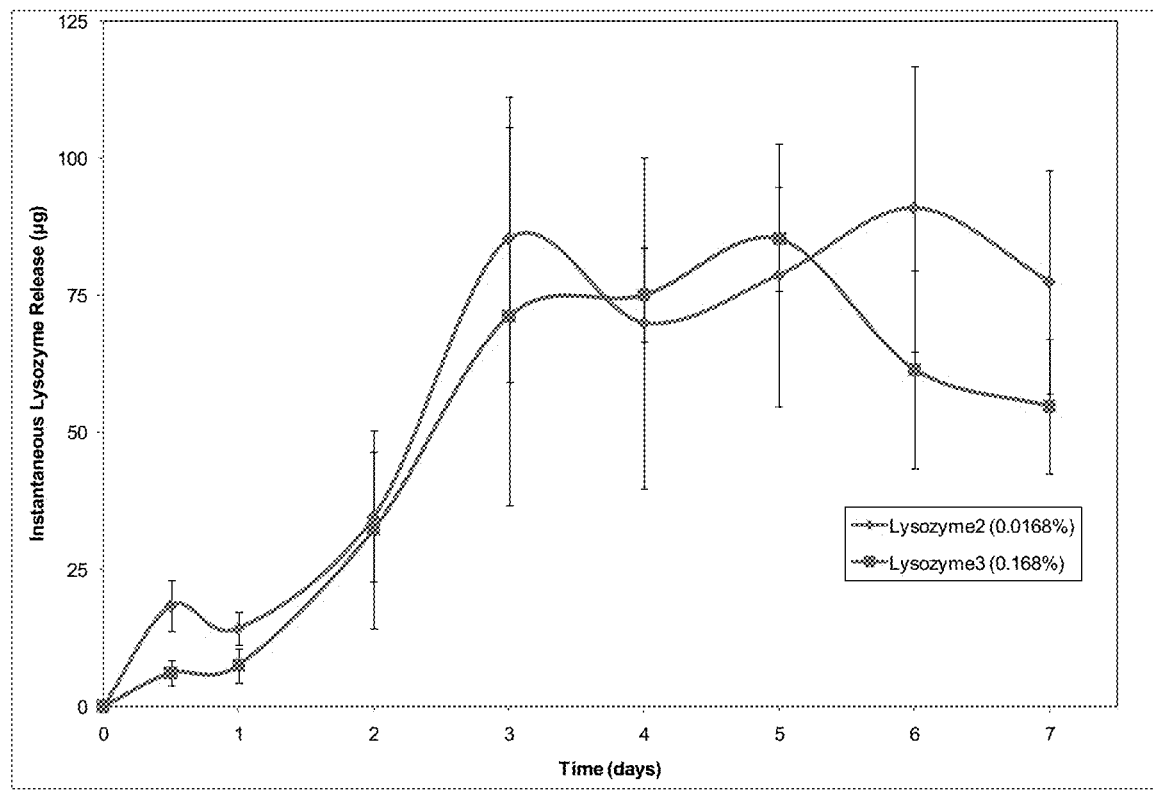
FIGS. 42A-42B are graphs showing the instantaneous (FIG. 42A) and cumulative (FIG. 42B) lysozyme release from bone graft compositions of the presently-disclosed subject matter, where the lysozyme was preadsorbed onto the bone particles prior to adding the bone particles to a calcium phosphate cement.
Figure 42B:
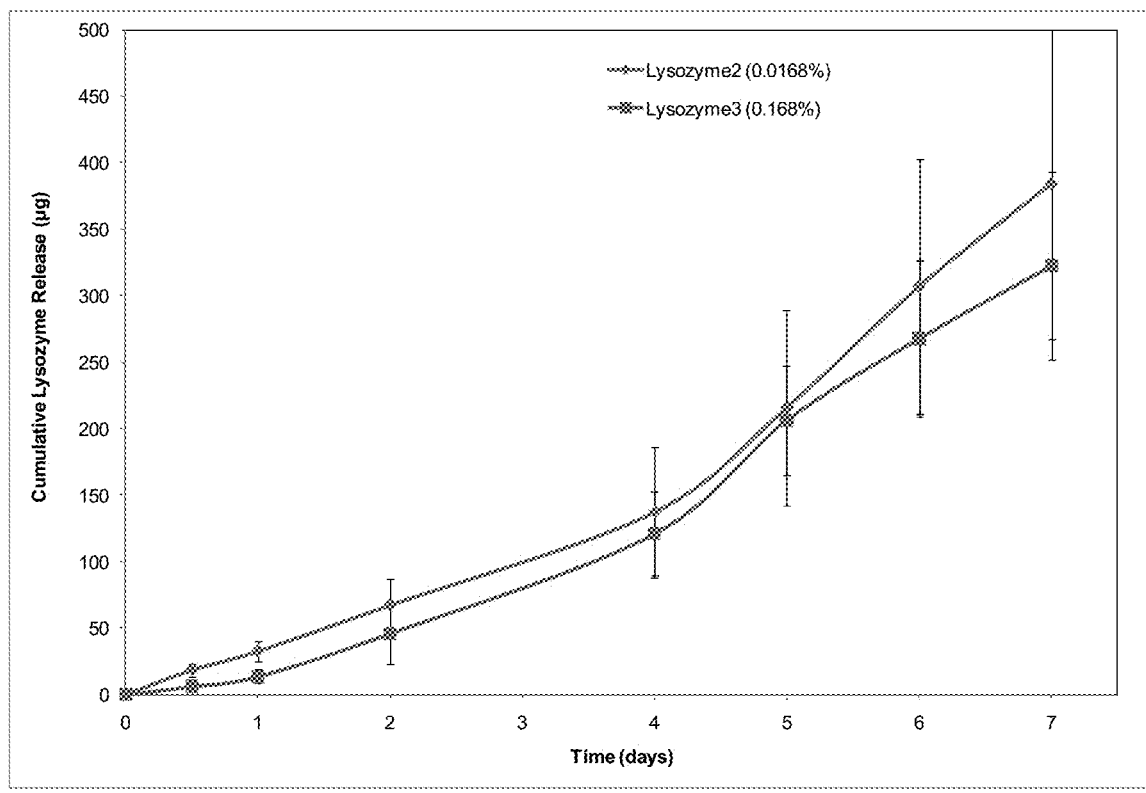
Figure 43A:
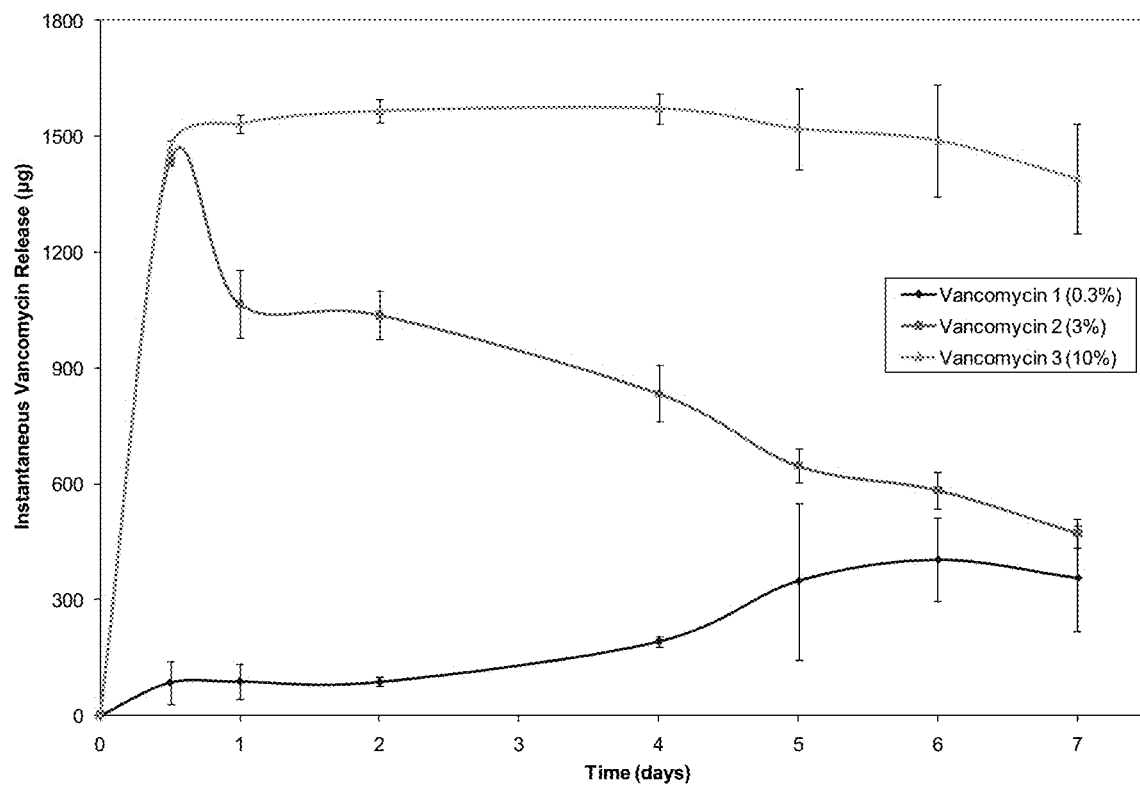
FIGS. 43A-43B are graphs showing the instantaneous (FIG. 43A) and cumulative (FIG. 43B) vancomycin release from bone graft compositions of the presently-disclosed subject matter, where the vancomycin was dry-mixed with the calcium phosphate cement and bone particles prior to the addition of an aqueous vehicle to set the mixture.
Figure 43B:
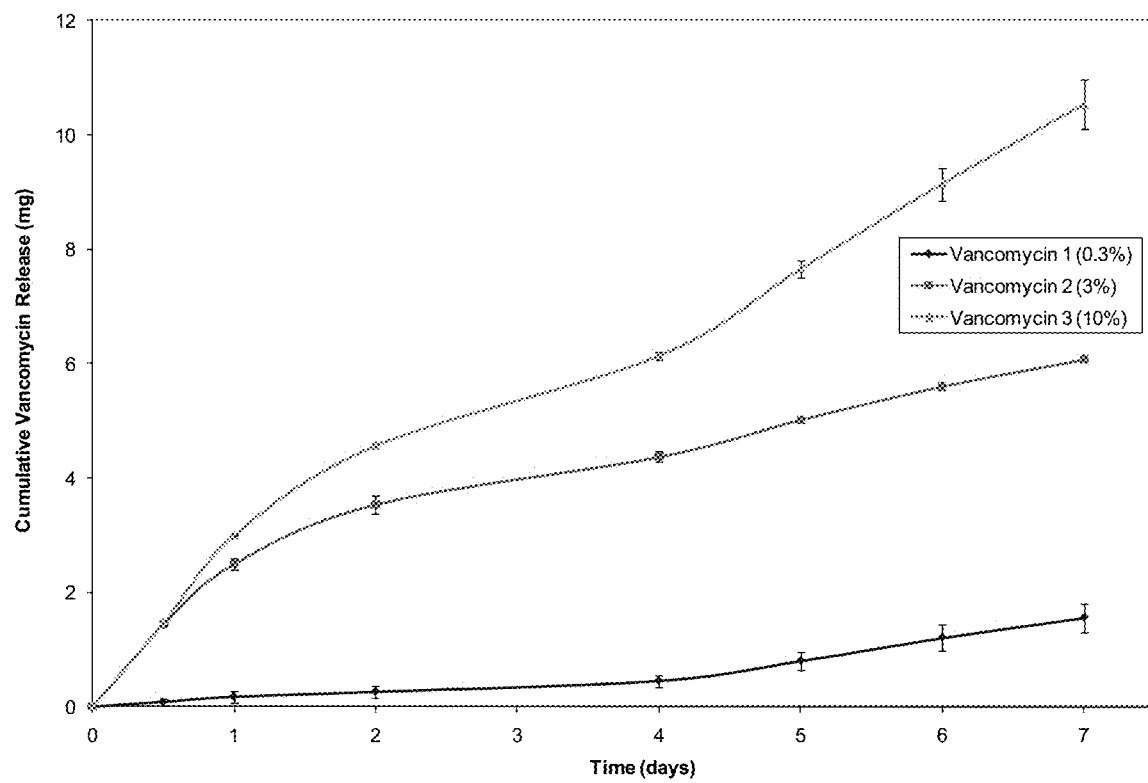
Figure 44A:
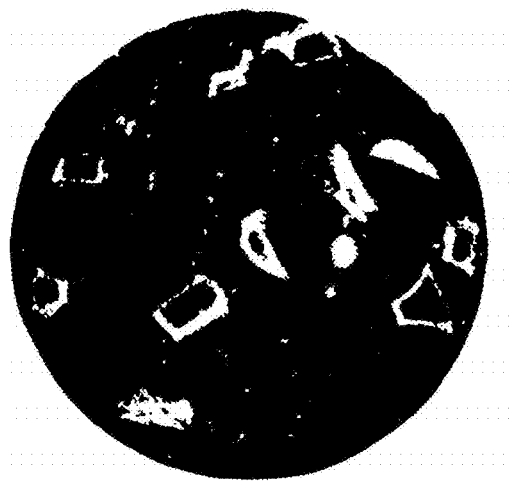
FIGS. 44A-44DD are images of serial sections of a bone graft composition of the presently-disclosed subject matter showing the distribution and interconnectedness of the plurality of processed bone particles that are included in the composition, where each of the processed bone particles has a shape as shown in FIG. 1A.
Figure 44B:
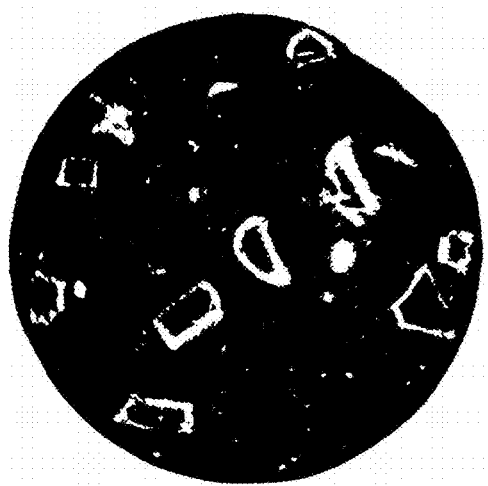
Figure 44C:
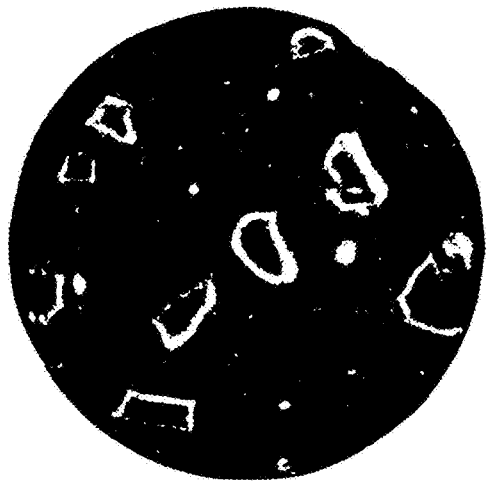
Figure 44D:
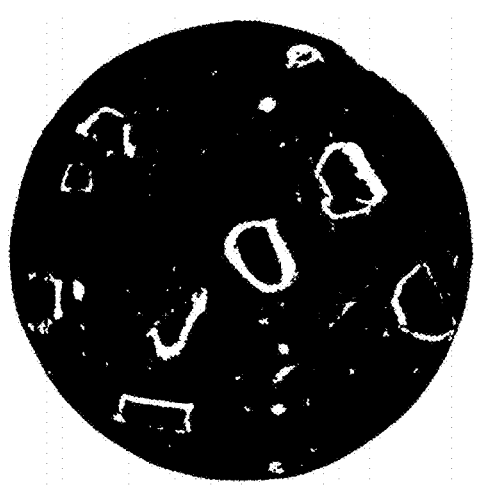
Figure 44E:
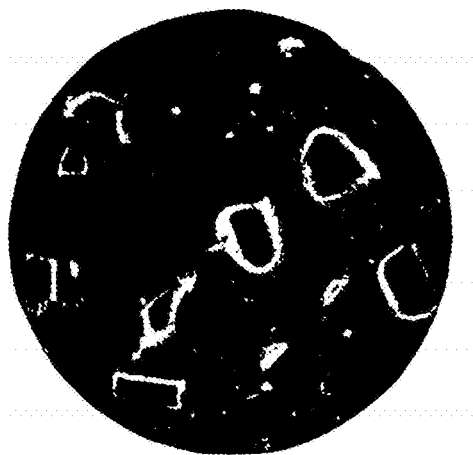
Figure 44F:
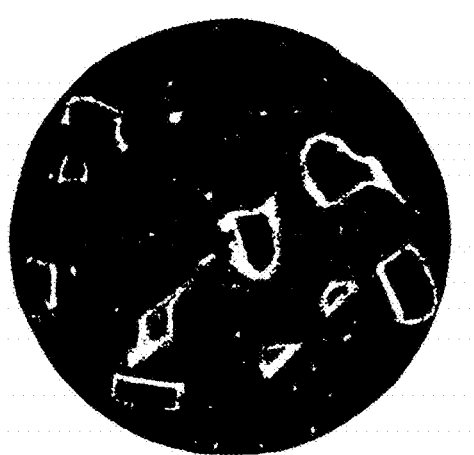
Figure 44G:
Figure 44H:
Figure 44I:
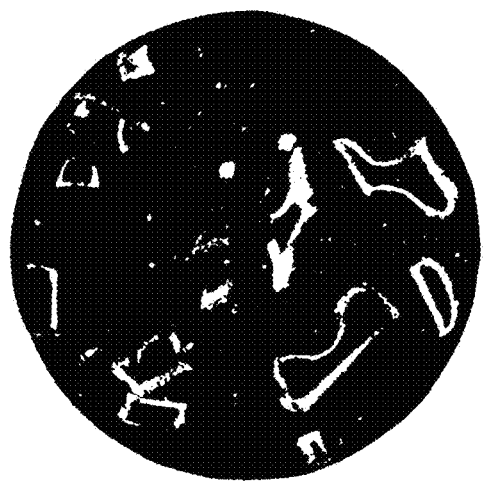
Figure 44J:
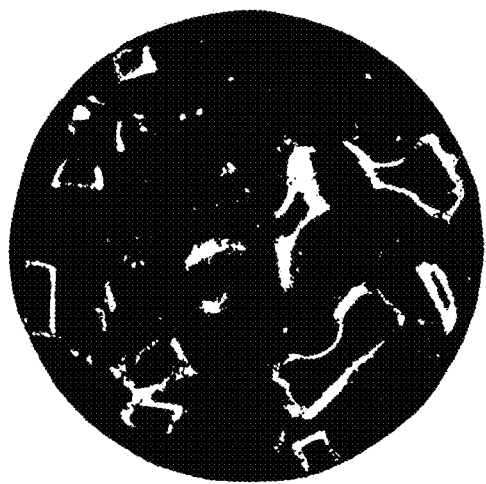
Figure 44K:
Figure 44L:
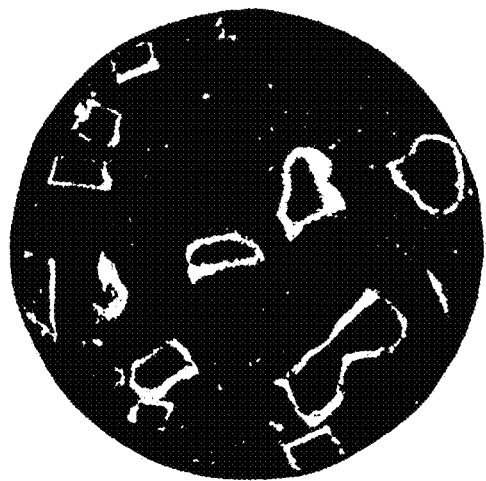
Figure 44M:
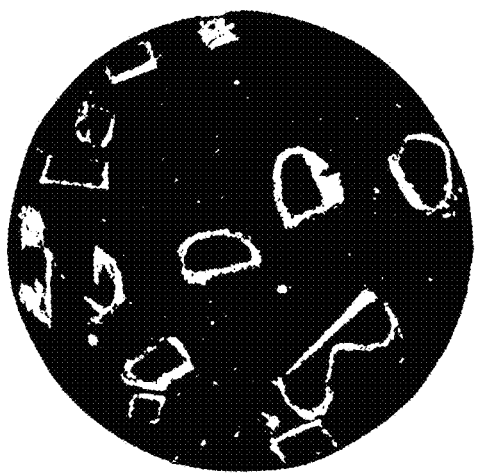
Figure 44N:
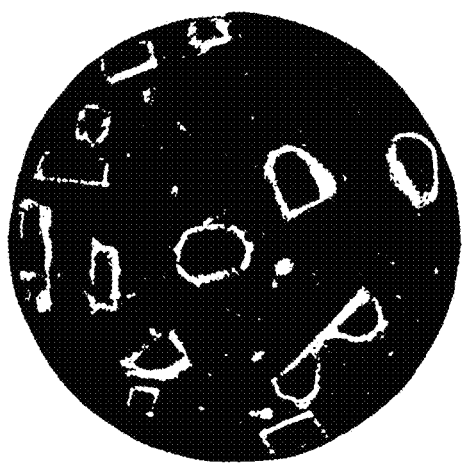
Figure 44O:
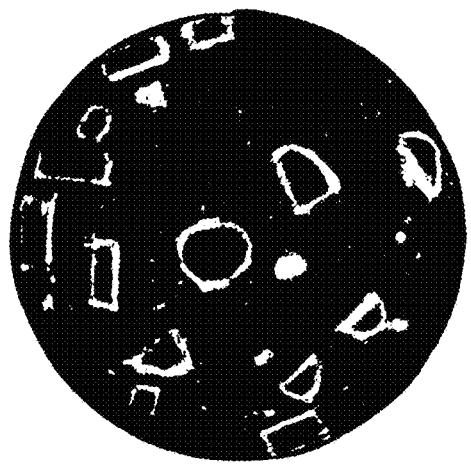
Figure 44P:
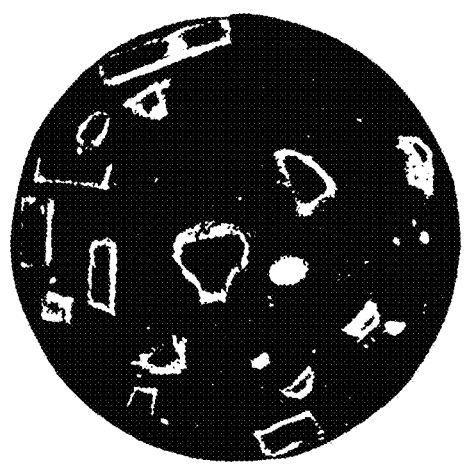
Figure 44Q:
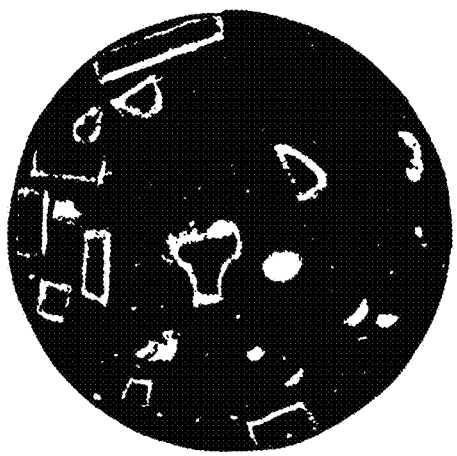
Figure 44R:
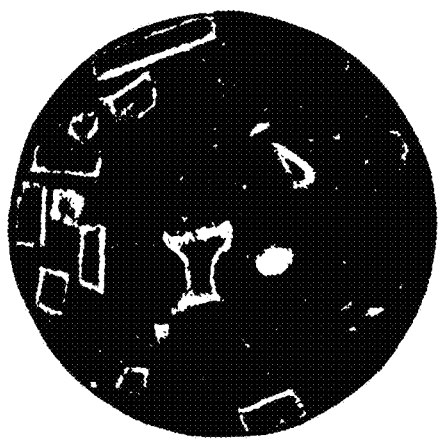
Figure 44S:
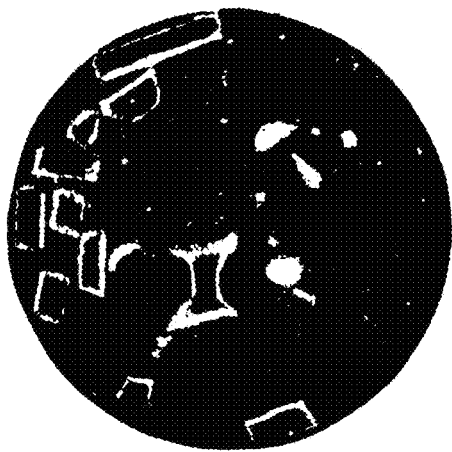
Figure 44T:
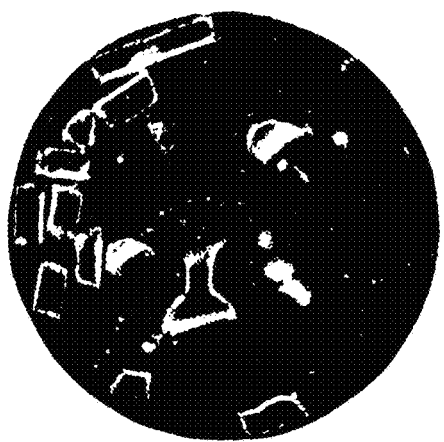
Figure 44U:
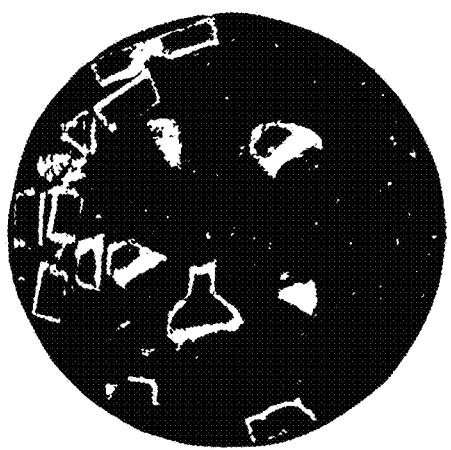
Figure 44V:
Figure 44W:
Figure 44X:
Figure 44Y:
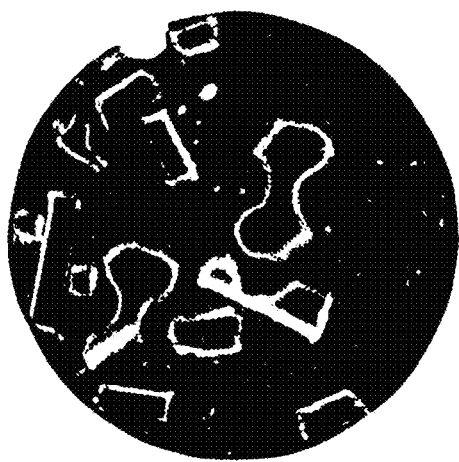
Figure 44Z:
Figure 44A:
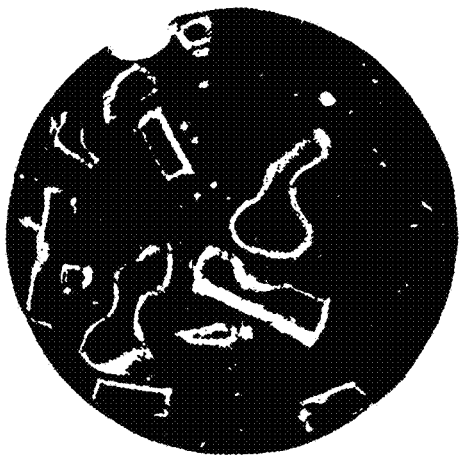
Figure 44B:
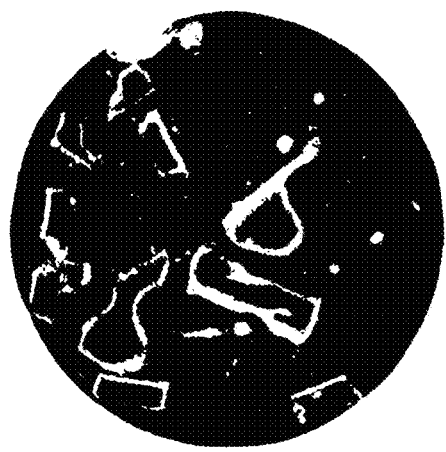
Figure 44C:
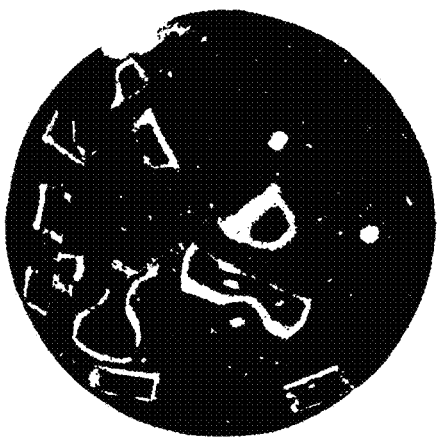
Figure 44D:
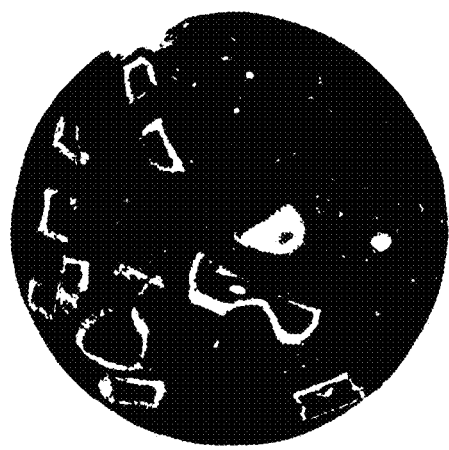

Upon analysis of the results from these experiments, it was found that the bone graft compositions of the present invention were capable of releasing both the growth factor analog protein, lysozyme (FIGS. 42A and 42B), and the antibiotic, vancomycin (FIGS. 43A and 43B). The lysozyme was released in similar amount regardless of the amount used because the available collagen layers of the bone particles controlled the protein. The vancomycin was released in a dose-dependent manner when placed in a liquid environment because it was mixed throughout the cement.

FIGS. 42A and 43A show the measured amount (μg) of lysozyme or vancomycin present in the supernatant at each point when it was replaced. The sum total (μg) of the lysozyme or vancomycin released is shown in FIGS. 42B and 43B. Due to the in vitro nature of the experiments, there were no dissolution of the hardened cements. Thus, only the antibiotic powder at the sample surface was available for release into the surrounding fluid. The rising cumulative release of lysozyme or vancomycin illustrates that the addition of specially-shaped and partially demineralized bone particles to a calcium phosphate cement can be utilized as an effective delivery systems for various therapeutic agents.

Throughout this document, various references are mentioned. All such references are incorporated herein by reference, including the references set forth in the following list:

REFERENCES

1. Almirall A, et al. 2004. "Fabrication of Low Temperature Macroporous Hydroxyapatite Scaffolds by Foaming and Hydrolysis of an α-TCP Paste. *Biomaterials*. 25:3671-80. [PubMed: 15020142]
2. Ambard, et al. 2006. "Calcium Phosphate Cement: Review of Mechanical and Biological Properties." *J Prosthodont*. 15(5):321-8.
3. Animal Cell Culture, Masters, ed., Oxford University Press, 2000.
4. ASTM D 790-03. Standard test methods for flexural properties of unreinforced and reinforced plastic and electrical insulating materials. West Conshohocken, Pa.: ASTM International; 2004.
5. Bohner M, et al. 2005. "Technological Issues for the Development of More Efficient Calcium Phosphate Bone Cements: a Critical Assessment." *Biomaterials* 26:6423-9. [PubMed: 15964620]
6. Bohner M, et al. 2005. "Injectability of Calcium Phosphate Pastes." *Biomaterials*. 26:1553-63. [PubMed: 15522757]
7. Bohner M. 2001. "Calcium phosphate emulsions: possible applications." *Key Eng Mater.* 192-195:765
8. Brown, W E et al. 1986. "A new Calcium Phosphate Water Setting Cement. In: Brown, P W., editor. Cements research progress. Westerville, Ohio: American Ceramic Society; 1986. p. 352-79.
9. Burguera E F, et al. 2008. "Injectable Calcium Phosphate Cement: "Effects of Powder-to-Liquid Ratio and Needle Size." *J Biomed Mater Res B Appl Biomater*. February; 84(2):493-502.
10. Burguera E F, et al. 2006. "Injectable and Rapid-setting Calcium Phosphate Bone Cement with Dicalcium Phosphate Dihydrate". *J Biomed Mater Res* 77B:126-34.
11. Burguera E F, et al. 2005. "High Early Strength Calcium Phosphate Bone Cement: Effects of Dicalcium Phosphate Dihydrate and Absorbable Fibers." *J Biomed Mater Res A*. December 15; 75(4):966-75.
12. Chow L C. 2000. "Calcium Phosphate Cements: Chemistry, Properties, and Applications." *Mater Res Symp Proc*. 599:27-37.
13. Costantino P D, et al. 1992. "Experimental Hydroxyapatite Cement Cranioplasty." *Plast Reconstr Surg*. 90:174-91. [PubMed: 1321453]
14. Damien C J, et al. 1991. "Bone Graft and Bone Graft Substitutes: a Review of Current Technology and Applications." *J Appl Biomater* 2:187-208. [PubMed: 10149083]

15. Ducheyne P, et al. 1999. "Bioactive Ceramics: the Effect of Surface Reactivity on Bone Formation and Bone Cell Function." *Biomaterials* 20:2287-303. [PubMed: 10614935]
16. Durucan C, et al. 2000. "Low Temperature Formation of Calcium-Deficient Hydroxyapatite-PLA/PLGA Composites." *J Biomed Mater Res* 51A:717-25. [PubMed: 10880121]
17. Embryonic Stem Cells, Methods and Protocols, Turksen, ed., Humana Press, 2002.
18. Fernández E, et al. 2005. "Modulation of Porosity in Apatitic Cements by the use of α-Tricalcium Phosphate-Calcium Sulphate Dehydrate Mixtures." *Biomaterials.* 26:3395-404. [PubMed: 15621228]
19. Fernández E, et al. 2005. "High-strength Apatitic Cement by Modification with Superplasticizers." *Biomaterials.* 26:2289-96. [PubMed: 15585231]
20. Friedman C D, et al. (1998) "BoneSource™ Hydroxyapatite Cement: a Novel Biomaterial for Craniofacial Skeletal Tissue Engineering and Reconstruction." *J Biomed Mater Res (Appl Biomater)* 43B:428-32.
21. Fukase Y, et al. 1990. "Setting Reactions and Compressive Strengths of Calcium Phosphate Cements." *J Dent Res December;* 69(12):1852-1856.
22. Gan L, et al. 2004. "Calcium Phosphate sol-gel-Derived Thin Films on Porous-surfaced Implants for Enhanced Osteoconductivity. Part I: Synthesis and Characterization. *Biomaterials* 25:5303-12. [PubMed: 15110481]
23. Genin D. "Percolation: Theory and Applications." NIST, 2007.
24. Ginebra M P, et al. 1997. "Setting Reaction and Hardening of an Apatite Calcium Phosphate Cement. *J Dent Res* 76:905-12. [PubMed: 9126187
25. Gbureck U, et al. 2005. "Factors Influencing Calcium Phosphate Cement Shelflife. *Biomaterials* 26:3691-7. [PubMed: 15621259]
26. Gbureck U, et al. 2004. "Ionic Modification of Calcium Phosphate Cement Viscosity: Part I: Hypodermic Injection and Strength Improvement of Apatite Cement. *Biomaterials* 25:2187-95. [PubMed: 14741634]
27. Guo H, et al. 2003. "Laminated and Functionally Graded Hydroxyapatite/yttria Stabilized Tetragonal Zirconia Composites Fabricated by Spark Plasma Sintering. *Biomaterials* 24:667-75. [PubMed: 12437961]
28. Grover L M, et al. 2003 "In vitro ageing of Brushite Calcium Phosphate Cement. *Biomaterials* 24:4133-41. [PubMed: 12853243]
29. Hench L L. 1998. "Bioceramics." *J Am Ceram Soc* 81:1705-28.
30. Hing K A, et al. 1999. "Characterization of Porous Hydroxyapatite." *J Mater Sci: Mater Med* 10:135-45. [PubMed: 15348161]
31. Ishikawa K, et al. 1997. "Non-decay type fast-setting calcium phosphate cement: Hydroxyapatite Putty Containing an Increased Amount of Sodium Alginate." *J Biomed Mater Res* 36A:393-9. [PubMed: 9260110]
32. Jackson et al., 1999. "Hematopoietic Potential of Stem Cells Isolated from Murine Skeletal Muscle." *PNAS* 96(25):14482-86.
33. Julien M, et al. 2007. "Physico-chemical-mechanical and in vitro Biological Properties of Calcium Phosphate Cements with Doped Amorphous Calcium Phosphates. *Biomaterials* 28:956-65. [PubMed: 17123598]
34. Laurencin C T, et al. 1999. "Tissue Engineering: Orthopedic Applications. *Ann Rev Biomed Eng* 1:19-46. [PubMed: 11701481]
35. LeGeros, R Z et al. 1993. "Dense Hydroxyapatite. In: Hench, L L.; Wilson, J., editors. An Introduction to Bioceramics. New Jersey: World Scientific; p. 139-80.
36. Lee, Singh R. et al. 2010. "Hierarchically Structured Titanium Foams for Tissue Scaffold Applications." *Acta Biomater*. December 6(12):4596-604.
37. Link D P, et al. 2006. "Mechanical Evaluation of Implanted Calcium Phosphate Cement Incorporated with PLGA Microparticles." *Biomaterials* 27:4941-7. [PubMed: 16759694]
38. Livingston T, et al. 2002. "In vivo Evaluation of a Bioactive Scaffold for Bone Tissue Engineering. *J Biomed Mater Res* 62A:1-13. [PubMed: 12124781]
39. Martin R B, et al. 1989. "Effects of Bone Ingrowth on the Strength and Non-invasive Assessment of a Coralline Hydroxyapatite Material." *Biomaterials* 10:481-8. [PubMed: 2804236]
40. Pilliar R M, et al. 2001. "Porous Calcium Polyphosphate Scaffolds for Bone Substitute Applications—in vitro Characterization." *Biomaterials* 22:963-72. [PubMed: 11311015]
41. Pittinger et al. 1999. "Multilineage potential of adult human mesenchymal stem cells." *Science*, April 2; 284 (5411):143-7.
42. Rabin B H, et al. 1995. "Functionally gradient materials". *Mater Res Soc Bull* 20:14-8.
43. Ryu H S, et al. 2004. "Fabrication of 1-Dimensional Porous Hydroxyapatite and Evaluation of its Osteoconductivity." *J Mater Sci Mater Med*. March; 15(3):267-7.
44. Saadeh P B, et al. 2001. "Repair of a Critical Size Defect in the Rat Mandible Using Allogenic Type I Collagen." *J Craniofac Surg*. November; 12(6):573-9.
45. Shors, E C.; et al. 1993. "Porous hydroxyapatite. In: Hench, L L.; Wilson, J., editors. An Introduction to Bioceramics. New Jersey: World Scientific; 1993. p. 181-98.
46. Simske S J, et al. 1997. "Porous materials for bone engineering." *Mater Sci Forum* 250:151-82.
47. Suchanek W, et al. 1998. "Processing and Properties of Hydroxyapatite-based Biomaterials for use as hard tissue Replacement Implants. *J Mater Res* 13:94-117.
48. Tamai N, et al. 2002. "Novel Hydroxyapatite Ceramics with an Interconnective Porous Structure Exhibit Superior Osteoconduction in vivo. *J Biomed Mater Res* 59A:110-7. [PubMed: 11745543]
49. Thomson R C, et al. 1998. "Hydroxyapatite Fiber Reinforced poly(α-hydroxyester) foams for Bone Regeneration. *Biomaterials* 19:1935-43. [PubMed: 9863527]
50. Ueyama Y, et al. 2001. "Initial Tissue Response to anti-washout Apatite Cement in the rat Palatal Region: Comparison with Conventional Apatite Cement. *J Biomed Mater Res* 55A:652-60. [PubMed: 11288095]
51. Verron, et al. 2010. "Calcium Phosphate Biomaterials as Bone Drug Delivery Systems: A Review." Drug Discovery Today. 15(13-14):547-52.
52. Wise D L, Encyclopedic Handbook of Biomaterials and Bioengineering. Part B, Volume 2.
53. Weissman I L, et al., 2001. "Stem and Progenitor Cells: Origins, Phenotypes, Lineage Commitments, and Trans-differentiations." *Annu Rev Cell Dev Biol*. 17:387-403.
54. Xu H H K, et al. 2006. "Development of a Nonrigid, Durable Calcium Phosphate Cement for use in Periodontal Bone Repair." *JADA*, August 137:1131-38.
55. Xu H H K, et al. 2002. "Processing and Properties of Strong and Non-rigid Calcium Phosphate Cement." *J Dent Res*. 81(3):219-24. [PubMed: 11881631]

56. Xu H H K, et al. 2002. "Calcium Phosphate Cement Containing Resorbable Fibers for Short-term Reinforcement and Macroporosity. *Biomaterials* 23:193-202. [PubMed: 11763861]
57. Xu H H K, et al. 2005. "Fast Setting Calcium Phosphate-chitosan Scaffold: Mechanical Properties and Biocompatibility. *Biomaterials* 26:1337-48. [PubMed: 15482821]
58. Xu H H K, et al. 2004. "Self-hardening Calcium Phosphate Composite Scaffold for bone Tissue Engineering. *J Orthop Res* 22:535-43. [PubMed: 15099632]
59. Xu H H K, et al. 2004. "Fast-setting and anti-washout Calcium Phosphate Scaffolds with High Strength and Controlled Macropore Formation Rates. *J Biomed Mater Res* 68A:725-34
60. Xu H H K, et al. 2006. "Injectable and Macroporous Calcium Phosphate Cement Scaffold. *Biomaterials* 27:4279-87. [PubMed: 16650891]
61. Xu, et al. *Biomaterials*. 23(1): 193-202 (2002).
62. Xu H H K, et al. 2001. "Strong and Macroporous Calcium Phosphate Cement: effects of porosity and fiber reinforcement. *J Biomed Mater Res* 57A:457-66. [PubMed: 11523041]
63. Xu et al., 2001. *J Biomed Mater Res*. December 5; 57(3):457-66.
64. Yokoyama A, et al. 2002. "Development of calcium phosphatecement using chitosan and citric acid for bone substitute materials." *Biomaterials* 23:1091-101. [PubMed: 11791912
65. Zhang Y, et al. 2006. "In-situ hardening hydroxyapatite-based scaffold for bone repair." *J Mater Sci: Mater Med* 17:437-45. [PubMed: 16688584]
66. Zhang Y, et al. 2005. "Effects of synergistic reinforcement and absorbable fiber strength on hydroxyapatite bone cement." *J Biomed Mater Res* 2005; 75A:832-40.
67. Zuk et al., *Tissue Engineering*, 7:211-228, 2001.
68. U.S. Pat. No. 7,628,851, issued to Armitage, et al., Dec. 8, 2009, and entitled "Bone Cement Compositions Having Fiber-Reinforcement and/or Increased Flowability."
69. U.S. Pat. No. 7,494,950, issued to Armitage et al., Feb. 24, 2009, and entitled "Bone Cement Compositions Having Fiber-Reinforcement and/or Increased Flowability."
70. U.S. Pat. No. 7,291,345, issued to Winterbottom et al., Nov. 6, 2007, and entitled "Bone Cement Compositions Having Fiber-Reinforcement and/or Increased Flowability."
71. U.S. Pat. No. 7,270,813, issued to Shimp, et al., Sep. 18, 2007, and entitled "Coupling Agents for Orthopedic Biomaterials."
72. U.S. Pat. No. 7,163,691, issued to Knaack, et al., Jan. 16, 2007, and entitled "Bone Graft."
73. U.S. Pat. No. 6,911,212, issued to Gertzman, et al., Jun. 28, 2005, and entitled "Malleable Putty and Flowable Paste with Allograft Bone Having Residual Calcium for Filling Bone Defects."
74. U.S. Pat. No. 6,599,516, issued to Knaack, Jul. 29, 2003, and entitled "Malleable Implant Containing Solid Element that Resorbs or Fractures to Provide Access Channels."
75. U.S. Pat. No. 6,548,080, issued to Gertzman et al., Apr. 15, 2003, and entitled "Method for Partially Demineralized Cortical Bone Constructs."
76. U.S. Pat. No. 6,432,436, issued to Gertzman et al., Aug. 13, 2002, and entitled "Partially Demineralized Cortical Bone Constructs."
77. U.S. Pat. No. 5,827,735, issued to Young et al., Oct. 27, 1998, and entitled "Pluripotent Mesenchymal Stem Cells and Methods of Use Thereof"
78. U.S. Pat. No. 5,672,346, issued to Srour et al., Sep. 30, 1997, and entitled "Human Stem Cell Compositions and Methods."
79. U.S. Pat. No. 5,559,022, issued to Naughton et al., Sep. 24, 1996, and entitled "Liver Reserve Cells."
80. U.S. Pat. No. 5,507,813, issued to Dowd, et al., Apr. 16, 1996, and entitled "Shaped Materials Derived from Elongate Bone Particles."
81. U.S. Pat. RE39,587, reissued to Gertzman et al., Apr. 24, 2007 and entitled "Malleable Paste for Filling Bone Defects."
82. U.S. Patent Pub. No. 2008/0145392 "Bone Graft," Knaack, et al. Jun. 29, 2008.
83. U.S. Patent Pub. No. 2007/0191963 "Injectable and Moldable Bone Substitute Materials," Winterbottom, et al., Aug. 16, 2007.
84. U.S. Patent Pub. No. 2004/0146543 "Synthesis of a Bone-Polymer Composite Material," Shimp, et al. Jul. 29, 2004.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A bone graft composition, comprising:
a biologically-resorbable cement; and
a plurality of processed interconnecting bone particles, each of the interconnecting bone particles being cut from an intact whole bone or portion thereof, each of the interconnecting bone particles having larger dimensions at its ends compared to its center, and each of the interconnecting bone particles having a shape configured to interconnect with adjacent interconnecting bone particles,
wherein the bone graft composition is configured to form a network of interconnected pathways or channels due to interconnected adjacent interconnecting bone particles, wherein the network of interconnected pathways or channels are configured to allow for cells and fluids to infiltrate the bone graft composition.

2. The bone graft composition of claim 1, wherein each of the interconnecting bone particles is further configured to interdigitate with the biologically-resorbable cement.

3. The bone graft composition of claim 1, wherein the biologically-resorbable cement is a calcium-based cement.

4. The bone graft composition of claim 3, wherein the calcium-based cement is a calcium phosphate cement.

5. The bone graft composition of claim 3, wherein the calcium-based cement is a calcium sulfate cement.

6. The bone graft composition of claim 1, wherein each of the interconnecting bone particles includes a plurality of enlarged portions and a plurality of center portions aligned along a common longitudinal axis, each of the enlarged portions extending laterally away from a common longitudinal axis of each center portion, and each of the center portions interposed between respective enlarged portions.

7. The bone graft composition of claim 1, wherein a cross-section of the interconnecting bone particles is substantially round, elliptical, square, rectangular, or triangular in shape.

8. The bone graft composition of claim 1, wherein the interconnecting bone particles are about 5% to about 90% demineralized.

9. The bone graft composition of claim 1, wherein the interconnecting bone particles comprise cortical bone, cancellous bone, or both cortical and cancellous bone.

10. The bone graft composition of claim 1, wherein the interconnecting bone particles are selected from the group consisting of autograft bone particles, allograft bone particles, xenograft bone particles, and combinations thereof.

11. The bone graft composition of claim 1, wherein the interconnecting bone particles comprise about 1 percent to about 50 percent by volume of the bone graft composition.

12. The bone graft composition of claim 1, wherein the composition further comprises an osteoinductive material, an osteogenic material, or both.

13. The bone graft composition of claim 1, wherein the composition further comprises an antibiotic.

14. A kit, comprising:
a biologically-resorbable cement powder; and
a plurality of processed interconnecting bone particles, each of the interconnecting bone particles being cut from an intact whole bone or portion thereof, each of the interconnecting bone particles having lamer dimensions at its ends compared to its center, and each of the interconnecting bone particles having a shape configured to interconnect with adjacent interconnecting bone particles,
wherein the plurality of processed interconnecting bone particles, when combined with the biologically-resorbable cement powder, are configured to form a network of interconnected pathways or channels due to interconnected adjacent interconnecting bone particles.

15. The kit of claim 14, wherein the interconnecting bone particles are lyophilized.

16. The kit of claim 14, further comprising an aqueous vehicle for adding to the biologically-resorbable cement powder, the interconnecting bone particles, or both the biologically-resorbable cement powder and the interconnecting bone particles.

17. The kit of claim 14, wherein the biologically-resorbable cement powder is contained in a first vessel, and wherein the processed interconnecting bone particles are contained in a second vessel.

18. The kit of claim 14, wherein the biologically-resorbable cement powder and the processed bone particles are packaged together in a single vessel.

19. The bone graft composition of claim 1, wherein the interconnecting bone particles comprise cancellous bone, wherein the cancellous bone comprises collagenous trabeculae with tunnel-like spaces configured to allow cells and fluids to infiltrate the bone graft.

* * * * *